(12) United States Patent
Nolan et al.

(10) Patent No.: US 7,179,267 B2
(45) Date of Patent: Feb. 20, 2007

(54) APPARATUS AND METHOD FOR PERFORMING A BYPASS PROCEDURE IN A DIGESTIVE SYSTEM

(75) Inventors: Tim Nolan, South Salem, NY (US); Ernie Aranyi, Easton, CT (US); John Klinger, Wallingford, CT (US); Keith Ratcliff, Newtown, CT (US); John Charles Robertson, Cheshire, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 680 days.

(21) Appl. No.: 10/234,086

(22) Filed: Aug. 30, 2002

(65) Prior Publication Data

US 2004/0087977 A1    May 6, 2004

Related U.S. Application Data

(63) Continuation of application No. PCT/US01/07105, filed on Mar. 5, 2001, now abandoned.

(60) Provisional application No. 60/187,121, filed on Mar. 6, 2000.

(51) Int. Cl.
*A61B 17/08* (2006.01)
*A61B 17/068* (2006.01)

(52) U.S. Cl. .................................. 606/153; 227/175.1

(58) Field of Classification Search ................. 606/153, 606/190, 191; 227/175.1, 179.1, 181.1
See application file for complete search history.

(56) References Cited

U.S. PATENT DOCUMENTS

| | | | |
|---|---|---|---|
| 4,157,709 A | 6/1979 | Schuster et al. | |
| 4,207,898 A | * 6/1980 | Becht | ........................ 227/179.1 |
| 4,304,236 A | 12/1981 | Conta et al. | |
| 4,328,805 A | 5/1982 | Akopov et al. | |
| 4,458,681 A | 7/1984 | Hopkins | |

(Continued)

FOREIGN PATENT DOCUMENTS

DE    1 057 729    3/1955

(Continued)

OTHER PUBLICATIONS

US 5,826,777, Oct. 1998, Green et al. (withdrawn).

(Continued)

*Primary Examiner*—Julian W. Woo

(57) ABSTRACT

Surgical instrumentation and methods for performing a bypass procedure in a digestive system incorporate laparoscopic techniques to minimize surgical trauma to the patient. The instrumentation includes an outer guide member dimensioned for insertion and passage through an esophagus of a patient and defining an opening therein extending at least along a portion of the length of the outer guide member, an elongate anvil delivery member at least partially disposed within the opening of the outer guide member and being adapted for longitudinal movement within the outer guide member between an initial position and an actuated position and an anvil operatively engageable with the delivery member. The anvil includes an anvil rod defining a longitudinal axis and an anvil head connected to the anvil rod. The anvil head is at least partially disposed within the opening of the outer guide member when in the initial position of the delivery member and is fully exposed from the distal end of the outer guide member upon movement of the delivery member to the actuated position.

45 Claims, 39 Drawing Sheets

U.S. PATENT DOCUMENTS

| | | |
|---|---|---|
| 4,473,077 A | 9/1984 | Noiles et al. |
| 4,592,339 A | 6/1986 | Kuzmak et al. |
| 4,646,745 A | 3/1987 | Noiles |
| 4,667,673 A | 5/1987 | Li |
| 4,696,288 A | 9/1987 | Kuzmak et al. |
| 4,760,837 A | 8/1988 | Petit |
| 4,803,985 A | 2/1989 | Hill |
| 4,817,847 A | 4/1989 | Redtenbacher et al. |
| 4,848,367 A | 7/1989 | Avant et al. |
| 4,873,977 A | 10/1989 | Avant et al. |
| 4,964,863 A | 10/1990 | Kanshin et al. |
| 5,033,481 A | 7/1991 | Heyler, III |
| 5,065,772 A | 11/1991 | Cox, Jr. |
| 5,074,868 A | 12/1991 | Kuzmak |
| 5,083,576 A | 1/1992 | Ruiz-Razura et al. |
| 5,104,025 A | 4/1992 | Main et al. |
| 5,122,156 A | 6/1992 | Granger et al. |
| D331,971 S * | 12/1992 | Main .................. D24/145 |
| 5,197,648 A | 3/1993 | Gingold |
| 5,226,429 A | 7/1993 | Kuzmak |
| 5,297,536 A | 3/1994 | Wilk |
| 5,314,435 A | 5/1994 | Green et al. |
| 5,314,436 A | 5/1994 | Wilk |
| 5,327,914 A | 7/1994 | Shlain |
| 5,330,486 A | 7/1994 | Wilk |
| 5,344,059 A | 9/1994 | Green et al. |
| 5,345,949 A | 9/1994 | Shlain |
| 5,355,897 A | 10/1994 | Pietrafitta et al. |
| 5,382,231 A | 1/1995 | Shlain |
| 5,395,030 A | 3/1995 | Kuramoto et al. |
| 5,401,241 A | 3/1995 | Delany |
| 5,445,644 A | 8/1995 | Pietrafitta et al. |
| 5,449,368 A | 9/1995 | Kuzmak |
| 5,458,131 A | 10/1995 | Wilk |
| 5,549,621 A | 8/1996 | Bessler et al. |
| 5,601,604 A | 2/1997 | Vincent |
| 5,626,591 A | 5/1997 | Köckerling et al. |
| 5,639,008 A | 6/1997 | Gallagher et al. |
| 5,658,298 A | 8/1997 | Vincent et al. |
| 5,665,093 A | 9/1997 | Atkins et al. |
| 5,718,666 A | 2/1998 | Alarcon |
| 5,741,268 A | 4/1998 | Schüntz |
| 5,771,903 A | 6/1998 | Jakobsson |
| RE36,176 E | 3/1999 | Kuzmak |
| 5,902,247 A | 5/1999 | Coe et al. |
| 5,919,136 A | 7/1999 | Rao et al. |
| 5,938,669 A | 8/1999 | Klaiber et al. |
| 5,976,078 A | 11/1999 | Bridges |
| 6,063,025 A | 5/2000 | Bridges et al. |
| 6,067,990 A | 5/2000 | Kieturakis |
| 6,117,148 A * | 9/2000 | Ravo et al. .................. 606/153 |
| 6,338,737 B1 * | 1/2002 | Toledano .................. 227/175.1 |

FOREIGN PATENT DOCUMENTS

| | | |
|---|---|---|
| EP | 0 419 660 A1 | 4/1989 |
| EP | 0 449 394 B1 | 10/1991 |
| EP | 0 282 157 B1 | 1/1993 |
| FR | 2689749 | 10/1993 |
| WO | WO 87/06448 | 11/1987 |
| WO | WO 90/06085 | 6/1990 |

OTHER PUBLICATIONS

Search Report for WO 01/66020 A3.

* cited by examiner

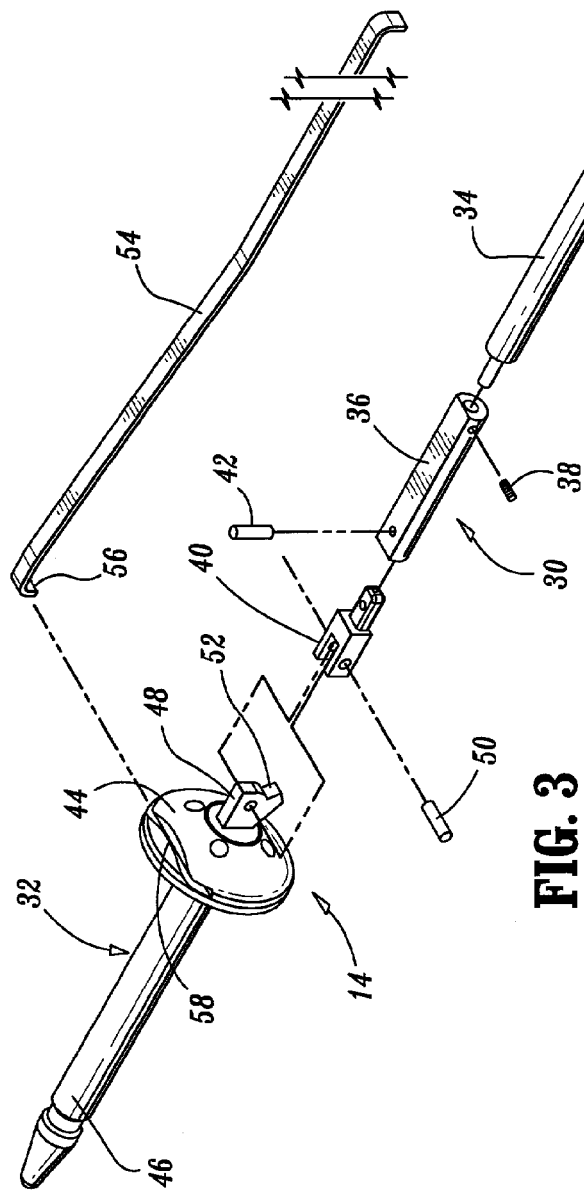
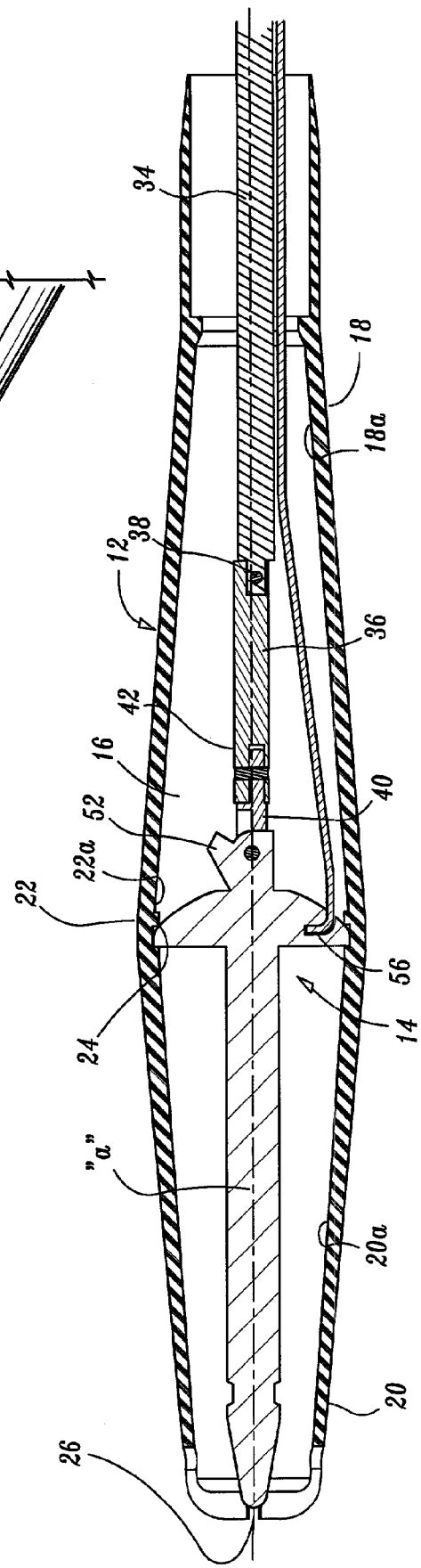
FIG. 3
FIG. 4

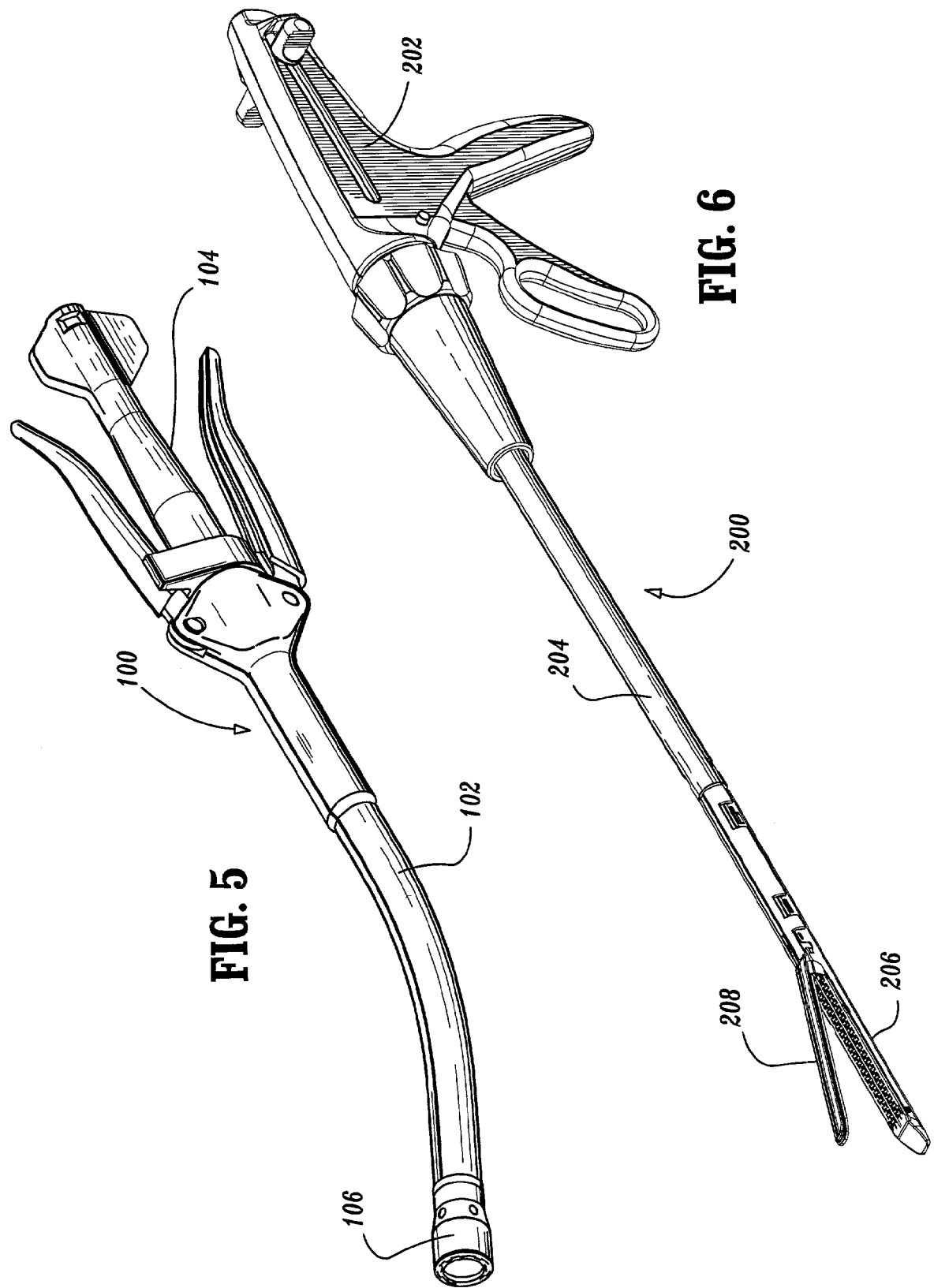

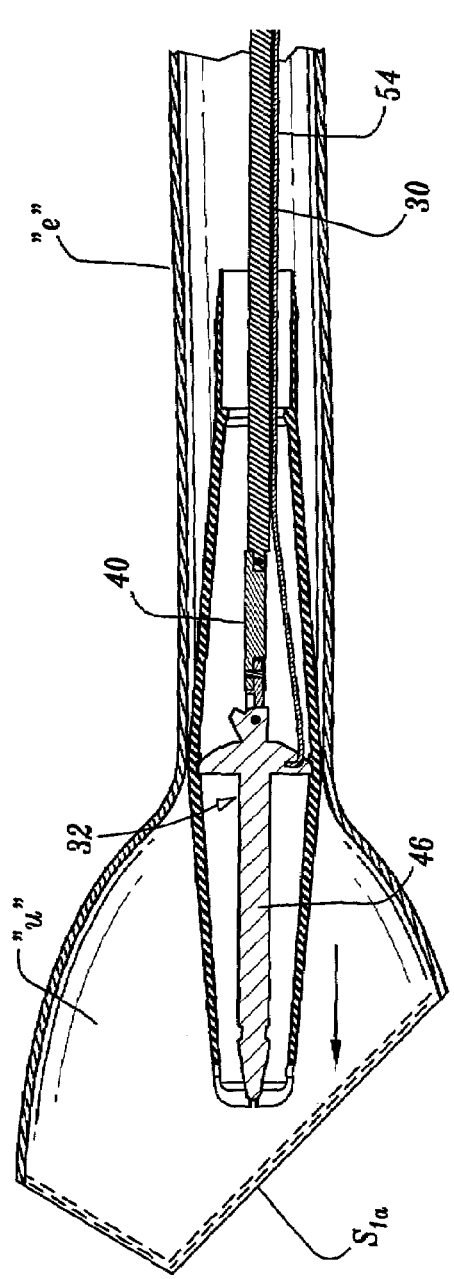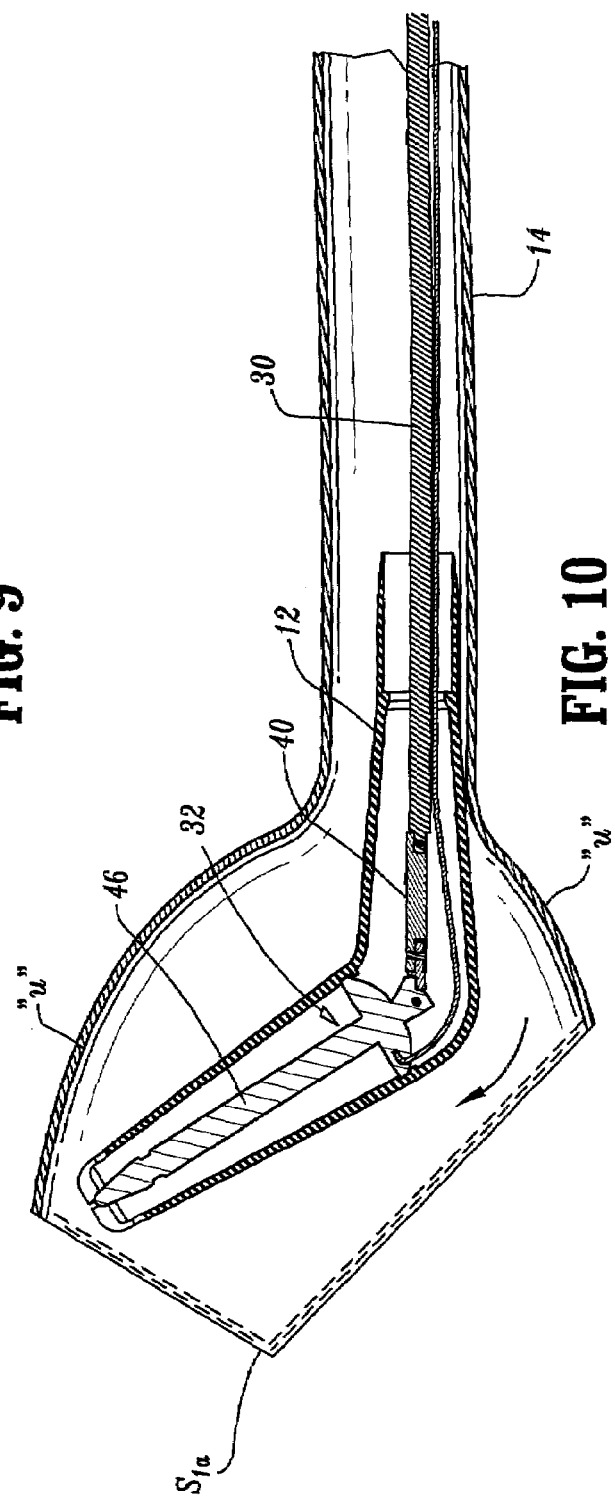
FIG. 9
FIG. 10

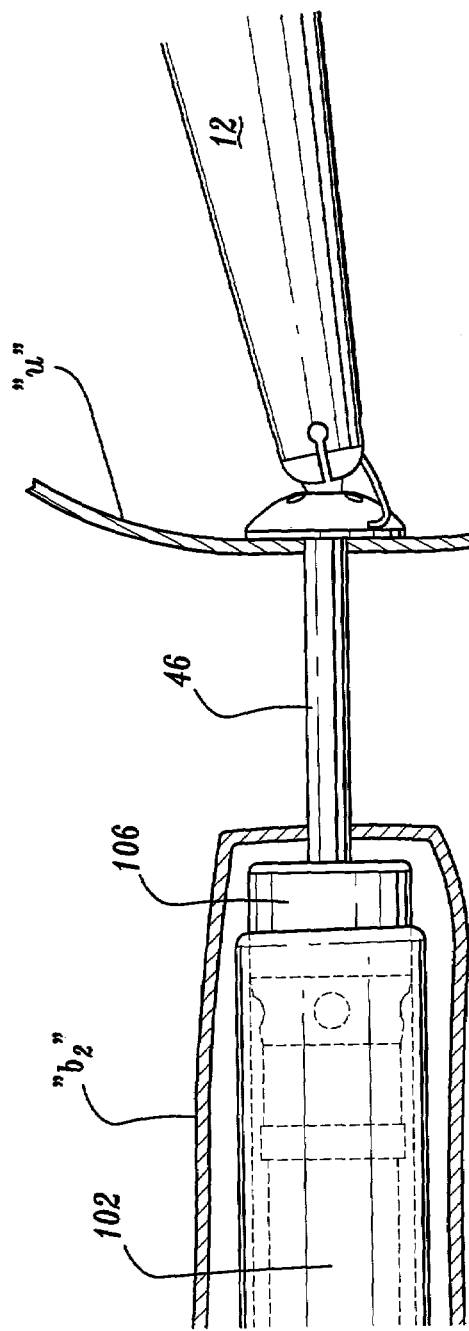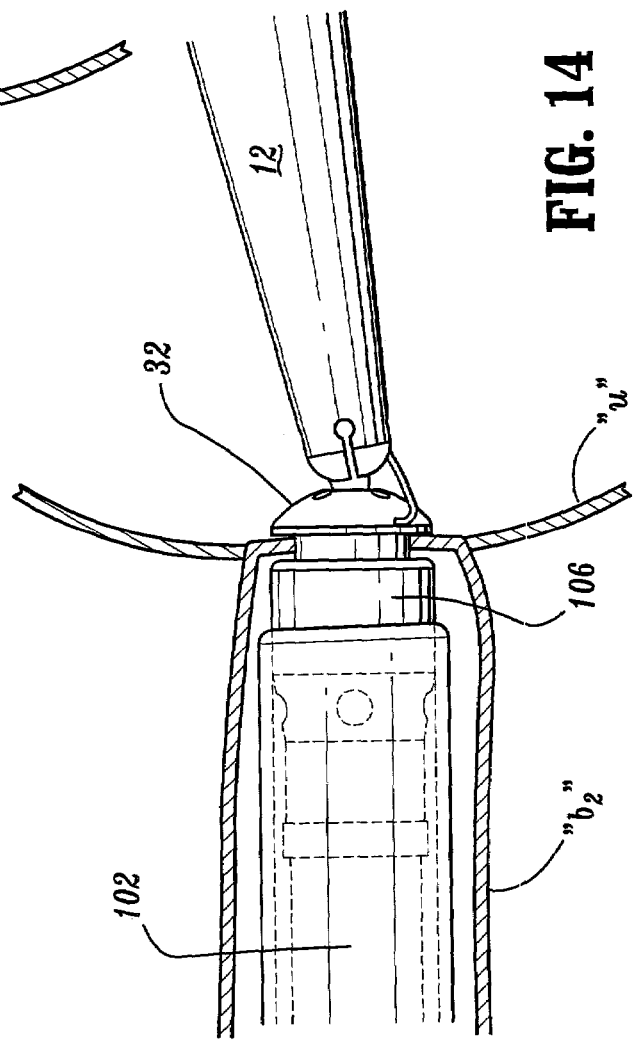

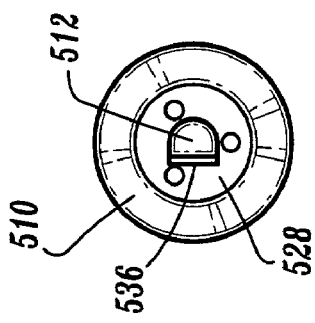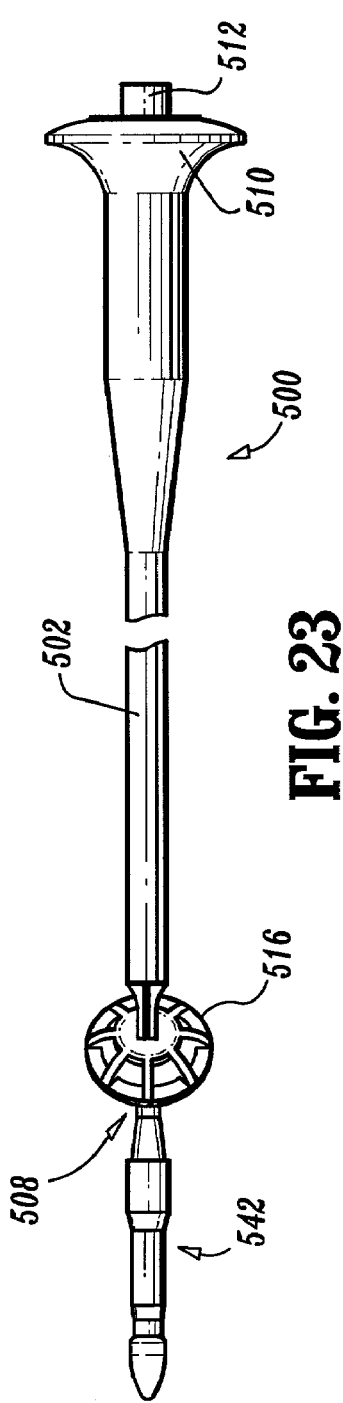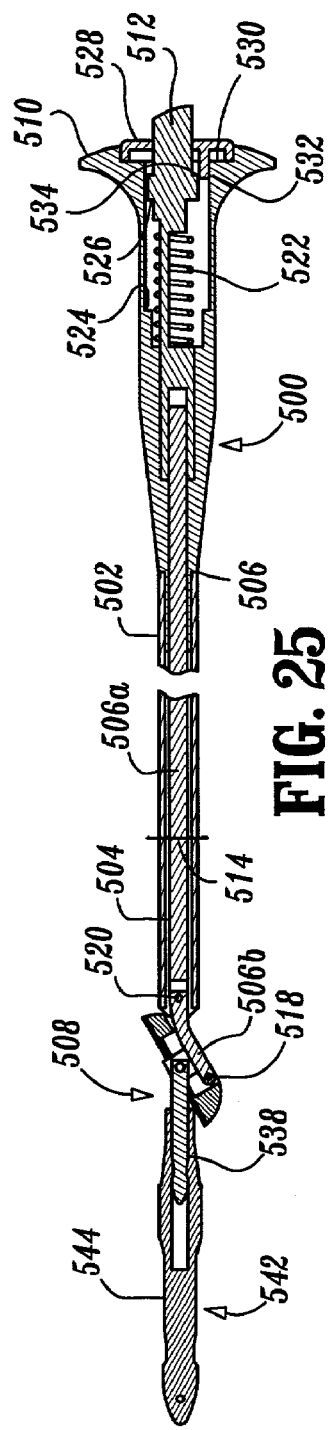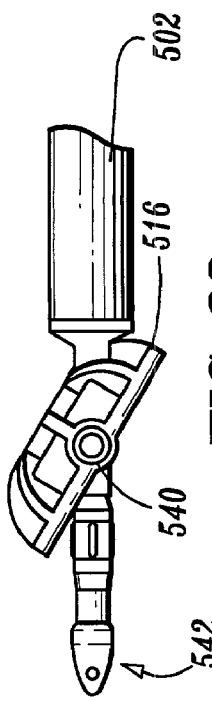

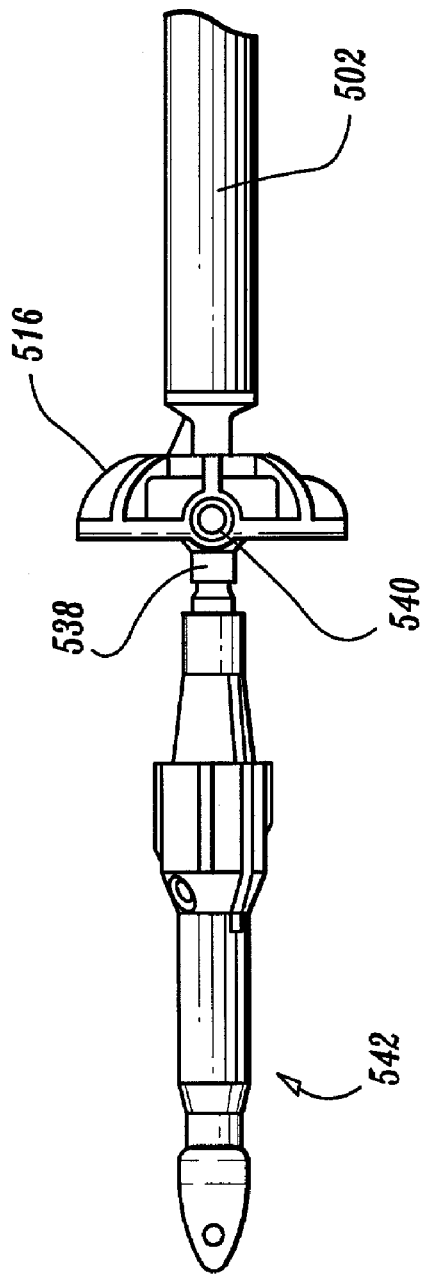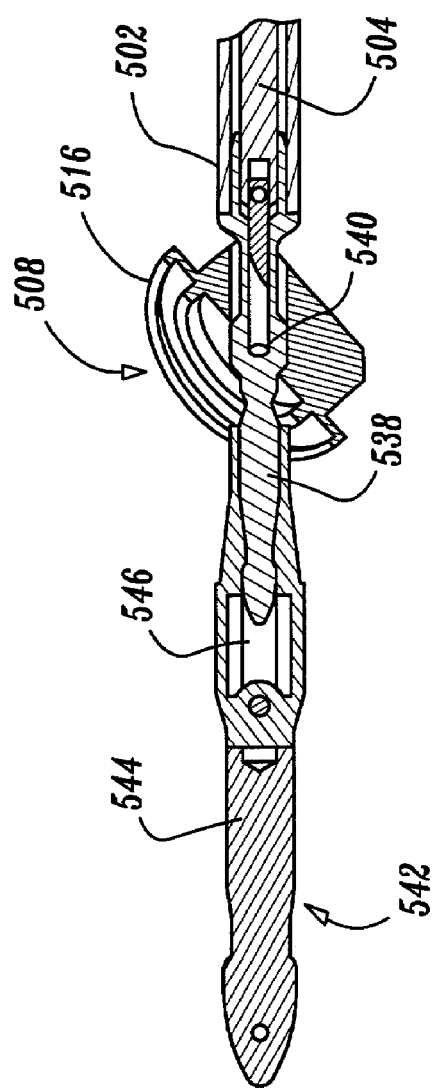
FIG. 27
FIG. 28

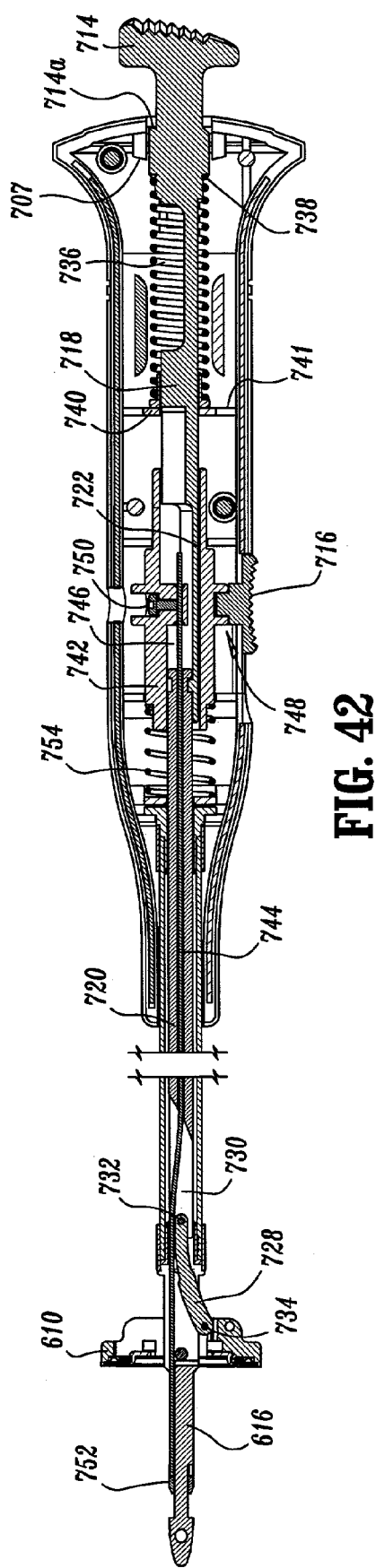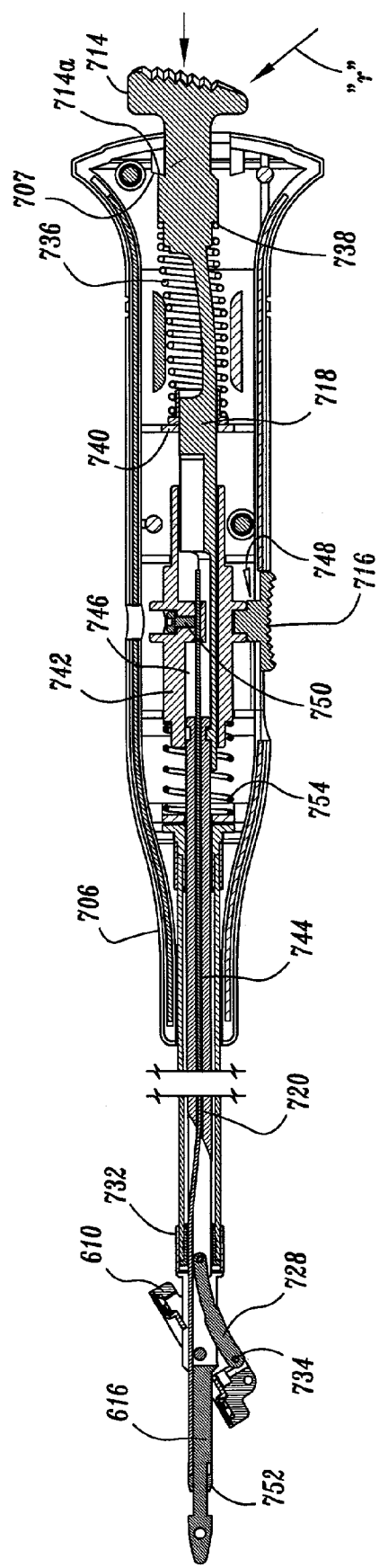
FIG. 42
FIG. 43

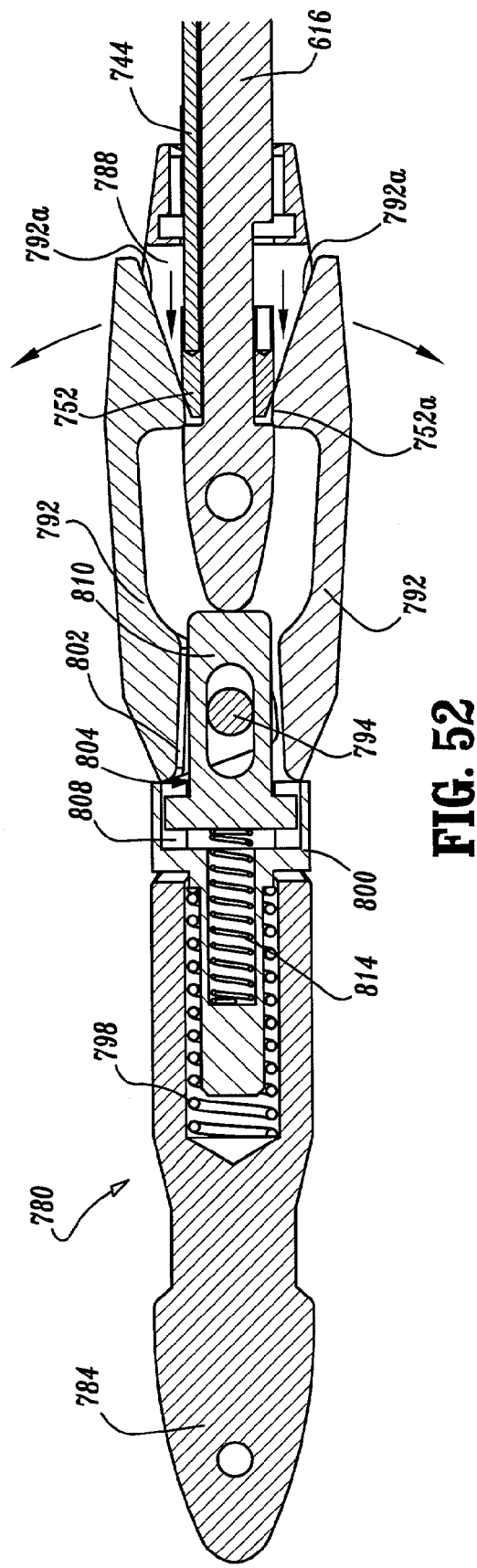
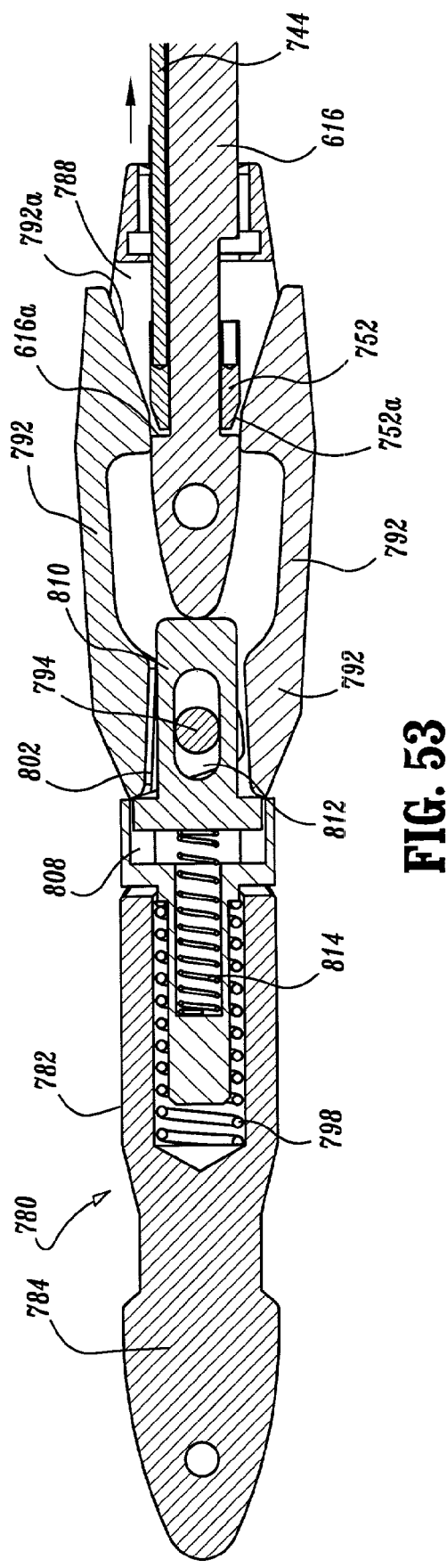
FIG. 52
FIG. 53

APPARATUS AND METHOD FOR PERFORMING A BYPASS PROCEDURE IN A DIGESTIVE SYSTEM

CROSS REFERENCE TO RELATED APPLICATIONS

This application is a continuation of International Application PCT/US01/07105, with an international filing date of Mar. 5, 2001, now abandoned, which claims the benefit of U.S. Provisional Application No. 60/187,121, filed Mar. 6, 2000.

BACKGROUND

1. Field of the Disclosure

The present disclosure relates generally to an apparatus and method for treating obesity, and, in particular, to an apparatus and method for performing a laparoscopic bypass procedure in a digestive system.

2. Description of the Related Art

Morbid obesity affects from about 3% to 5% of the population. The severely obese are at significantly greater risk of premature death, heart disease, stroke, diabetes mellitus, cancer, pulmonary diseases, orthopaedic complications and accidents. The obese are also subject to discrimination in society, the workplace, etc.

Several methods for treatment of morbid obesity include diets, pills, and other weight-reducing plans. Mechanical devices for insertion into the stomach, e.g., gastric balloons, to at least partially occupy the stomach have also been utilized. These approaches, however, are generally effective for a limited period of time. In addition, over 95% of those participating in such approaches regain their original weight, and, in many instances, gain additional weight.

Methods for treating obesity proven effective over the long term include surgery to restrict the amount of food consumed at one sitting and to change the digestive process such that less of the food consumed will be absorbed into the body. These procedures are collectively known as Bariatric Surgery and include Gastroplasty, Gastric Banding and Gastric Bypass.

Gastroplasty incorporates separating the stomach into two pouch areas, e.g., an upper pouch and a lower pouch, through stapling. A small opening or stoma is then formed through the row of staples. Thus, the consumed food collects within the upper pouch and passes through the stoma and into the lower pouch at a reduced rate thereby giving a sensation of fullness to the individual to limit the amount of food intake. Disadvantages of this procedure include expansion of the upper pouch and the stoma which thereby minimizes long term effectiveness of this procedure.

In Vertical Banded Gastroplasty (VBG), an upper gastric pouch is formed within the stomach by applying a vertical row of staples. A band (e.g., a Marley mesh) is applied about the stomach adjacent the staple line to prevent dilation of the outlet port extending from the upper pouch into the remaining portion of the stomach. The Vertical Banded Gastroplasty (VBG) method, however, is subject to certain disadvantages including problematic post-operative healing, high rate of complications such as wound infection, pulmonary emboli, gastric perforation, gall bladder stones, etc.

Gastric Bypass combines the elements of intestinal rearrangement with a smaller stomach pouch. More particularly, with this procedure, the stomach is divided into an upper pouch and a lower pouch. The upper pouch, which receives the consumed food, is greatly reduced in capacity and is directly connected to the small intestine. However, conventional gastric bypass techniques involve invasive surgical approaches which have a deleterious effect on patient recovery and down time.

In recent years, minimally invasive surgical techniques have been developed to reduce trauma to the patient and minimize recover time. Such minimally invasive procedures include endoscopy, laparoscopy, colonoscopy, etc. and typically require elongated narrow instruments to perform surgery on organs, tissues and vessels far removed from the incision. Laparoscopic procedures are performed in the interior of the abdomen through a small incision, e.g., through a tube or cannula inserted through a small entrance incision in the abdominal cavity. To date, however, satisfactory laparoscopic approaches and instrumentation for a bypass procedure in a digestive system have not been developed.

SUMMARY

Accordingly, the present disclosure is directed to surgical instrumentation and methods for performing a bypass procedure in a digestive system, which incorporates laparoscopic techniques to minimize surgical trauma to the patient. In one preferred embodiment, an apparatus for facilitating performance of a gastroplasty procedure, includes an outer guide member dimensioned for insertion and passage through an esophagus of a patient and defining an opening therein extending at least along a portion of the length of the outer guide member, an elongate anvil delivery member at least partially disposed within the opening of the outer guide member and being adapted for longitudinal movement within the outer guide member between an initial position and an actuated position and an anvil operatively engageable with the delivery member. The anvil includes an anvil rod defining a longitudinal axis and an anvil head connected to the anvil rod. The anvil head is at least partially disposed within the opening of the outer guide member when in the initial position of the delivery member and is fully exposed from the distal end of the outer guide member upon movement of the delivery member to the actuated position.

The anvil head may be pivotally mounted to the anvil rod and movable between a non-operative position and an operative position. A pivot member at least partially disposed within the outer guide member and operatively connected to the anvil head moves between first and second positions thereof to cause corresponding movement of the anvil head between the respective non-operative and operative positions. The pivot member is normally biased to the second position thereof. Means for releasably locking the pivot member in the first position may be provided. Preferably, the pivot member includes a locking surface engageable with a corresponding locking surface of one of the delivery member and outer guide member to releasably lock the pivot member in the first operative position. Preferably, the pivot member includes a manually operable handle which defines the locking surface of the pivot element. The pivot member is preferably dimensioned to extend proximally beyond the insertion member to be grasped by the surgeon.

Alternatively, the anvil may be pivotally mounted to the delivery member. An elongate pivot member at least partially disposed within the outer guide member is operatively connected to the anvil and is movable to cause corresponding pivotal movement of the anvil through a pivotal range of motion.

A method for performing a bypass procedure in a digestive system is also disclosed. The method includes the steps of introducing an anvil through an esophagus of a patient and into a first digestive tissue portion, inserting an anastomosis instrument into a second digestive tissue portion displaced from the first digestive tissue portion, manipulating the anvil from a proximal location to position the anvil at a desired orientation with respect to the anastomosis instrument, connecting the anvil to the anastomosis instrument and firing the anastomosis instrument to connect the first and second digestive tissue portions.

In the alternative, a method for performing a bypass procedure in a digestive system includes the steps of isolating an upper stomach portion of the stomach of a patient, resecting the bowel to define a bowel portion disconnected from the stomach, and connecting the bowel portion and the upper stomach portion. The step of connecting is preferably performed with an end to end anastomosis instrument. The method may further include the step of introducing an anvil adapted for use with the anastomosis instrument through an esophagus and into the upper stomach portion and introducing an end to end anastomosis instrument into the bowel portion. The anvil and the end to end anastomosis instrument are connected, and the end to end anastomosis instrument is fired to connect the bowel portion and the upper stomach portion.

The step of isolating may include positioning a linear stapler instrument about the stomach and firing the linear stapler to isolate the upper stomach portion with resect to the remainder of the stomach. Similarly, the step of resecting includes positioning a linear stapler about the small bowel and firing the linear stapler. The linear stapler may have a knife blade associated therewith and wherein upon firing the knife blade is actuated to resect the bowel to define the bowel portion.

In an alternative, the method for performing a bypass procedure in a digestive system includes the steps of accessing digestive tissue portions of a digestive system, advancing an anvil through the esophagus and into the first digestive tissue portion, inserting an anastomosis instrument into the second digestive tissue portion, connecting the anvil with the anastomosis instrument and firing the anastomosis instrument to connect the first and second digestive tissue portions, disconnecting the anvil from the anastomosis instrument, and withdrawing the anvil through the esophagus.

The method may further include the step of manipulating the anvil from a proximal location outside the body to facilitate connecting of the anvil with the anastomosis instrument.

BRIEF DESCRIPTION OF THE DRAWINGS

Preferred embodiments of the disclosure are described herein with reference to the drawings wherein:

FIG. 3 is a perspective view with parts separated of the anvil delivery member;

FIG. 4 is a side cross-sectional view of the apparatus;

FIG. 5 is a perspective view of an end to end anastomosis utilized to perform the gastric bypass procedure;

FIG. 6 is a perspective view of a endoscopic stapling instrument utilized to perform the gastric bypass procedure;

FIGS. 7–16 are views illustrating the sequence of steps in performing a laparoscopic gastric bypass procedure in accordance with one preferred method of the present disclosure;

FIG. 23 is a side plan view of an alternate embodiment of the apparatus of FIG. 1;

FIG. 24 is an axial view of the apparatus of FIG. 23;

FIG. 25 is a side cross-sectional view of the apparatus;

FIG. 26 is a side plan view of the distal end of the apparatus illustrating the anvil in an inoperative position;

FIG. 27 is a view similar to the view of FIG. 26 illustrating the anvil in an operative position;

FIG. 28 is a side cross-sectional view of the distal end of the apparatus;

FIG. 42 is a side cross-sectional view of the apparatus in an initial position;

FIG. 43 is a view similar to the view of FIG. 42 illustrating the pivot mechanism actuated corresponding to the pivoted position of the anvil head;

FIGS. 52–53 are cross-sectional views of the anvil adapter illustrating activation of the release mechanism to release the anvil adapter from the anvil assembly.

DETAILED DESCRIPTION OF PREFERRED EMBODIMENTS

Figure 1:
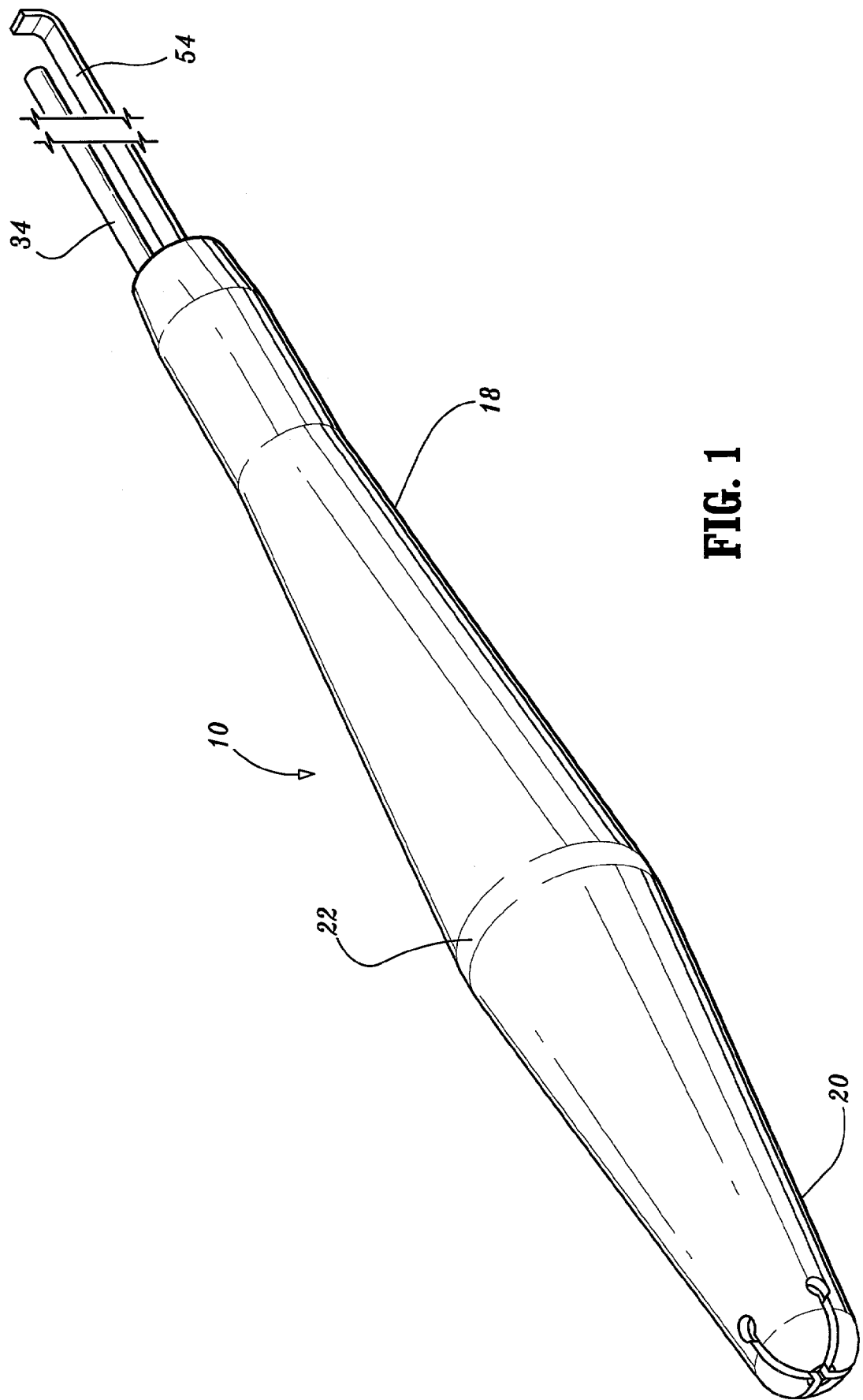
FIG. 1 is a perspective view of the apparatus for facilitating performance of a gastric bypass procedure in accordance with the principles of the present disclosure.

The preferred embodiments of the method and instrumentation disclosed herein are discussed in terms of bypass procedures in the digestive system, and instrumentation utilized to carry-out the procedures. Although described specifically in connection with a laparoscopic approach, it is envisioned that the disclosure is applicable to a conventional open approach as well.

The following discussion will include a description of each instrument utilized in performing a digestive system bypass procedure followed by a description of preferred methods for bypass utilizing the instrumentation in accordance with the present disclosure.

In the discussion which follows, the term "proximal", as is traditional, will refer to the portion of the structure which is closest to the operator, while the term "distal" will refer to the portion which is furthest from the operator.

Referring now to FIGS. 1–4, there is illustrated one preferred embodiment of the apparatus for performing a laparoscopic digestive bypass procedure in accordance with the principles of the present disclosure. Apparatus 10 includes generally two components, namely, outer guide member 12 and anvil delivery member 14 which is at least partially disposed within the outer guide member 12. Guide member 12 is fabricated from a flexible material such that the guide member 12 may bend or flex as required during deployment of the anvil delivery member 14. In a preferred embodiment, guide member 12 comprises an elastomeric material. As best depicted in FIG. 4, guide member 12 includes an internal opening or cavity 16 which accommodates at least a portion of delivery member 14. Guide member 12 defines longitudinal axis "a" and has proximal end portion 18, distal end portion 20 and intermediate portion 22 disposed between the proximal and distal end portions 18, 20. Intermediate portion 22 defines an internal dimension 22a which is larger than both the respective internal dimensions 18a, 20a of the proximal end portion 18 and the distal end portion 20. Intermediate portion 22 also includes an internal groove 24 defined therein (FIG. 4). Preferably, each of the proximal and distal end portions 18, 20 of guide member 12 gradually taper in linear relation to intermediate portion 22 as shown. Distal end portion 20 of guide member 12 further defines an axial opening 26. Slits 28 permit the guide member 12 to flare outwardly to enlarge the effective size of opening 26.

Figure 2:
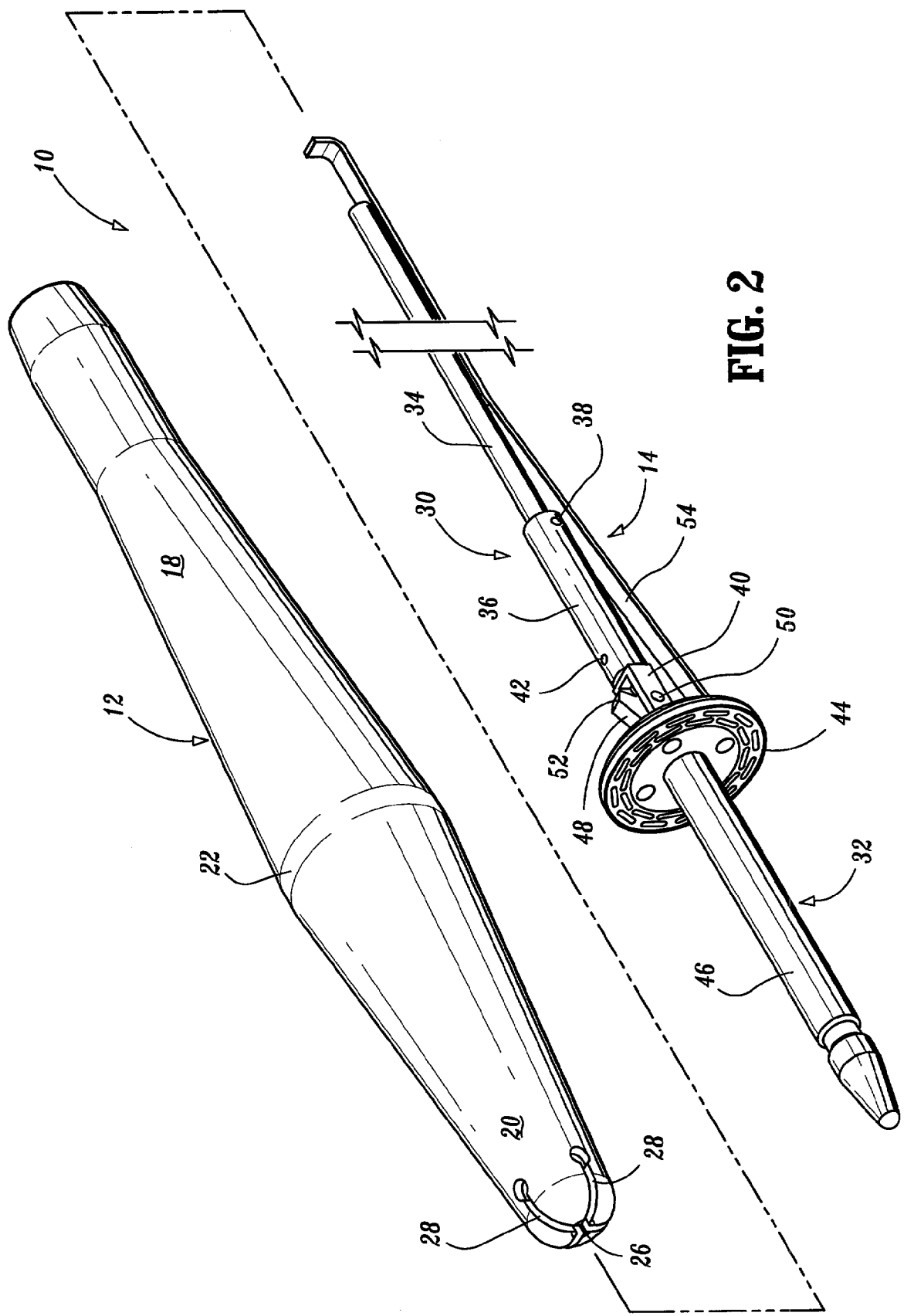
FIG. 2 is a perspective view with parts separated of the apparatus of FIG. 1, illustrating the insertion member and the anvil delivery member of the apparatus.

With particular reference to FIGS. 2–4, anvil delivery member 14 includes elongated support member 30 and anvil 32 which is supported at the distal end portion of the support member 30. Support member 30 includes elongate member 34, pivot block support 36 mounted to the elongate member 34 by pin 38 and pivot block 40 which is connected to the pivot block support 36 by pin 42. Although shown as several components, it is appreciated that support member 30 can be manufactured as a monolithic unit as well. Elongate member 34 is preferably sufficient in length and relatively flexible to extend from the stomach through the esophagus of the patient and out the oral cavity to be grasped by the surgeon.

Anvil 32 is intended for use with a circular or end-to-end anastomosis instrument as will be discussed. Anvil 32 includes anvil head 44 and anvil rod 46 extending from the anvil head 44. Generally, anvil head 44 includes a plurality of recesses which are adapted to form and close staples ejected from the circular anastomosis instrument. Anvil rod 46 engages corresponding mounting structure of the circular anastomosis instrument to mount anvil 32 to the instrument. Anvil 32 further includes pivot head 48 which pivotally connects to pivot block 40 through pin 50 to permit the anvil 32 to pivot through at least a predetermined range of pivotal motion. In a preferred embodiment, anvil 32 is pivotable through a 90° range of motion in one direction relative to the longitudinal axis with the range of motion being restricted by engagement of shelf 52 of pivot head 48 and pivot block 40 (see FIG. 4). One anvil suitable for the purposes of the present disclosure is disclosed in commonly assigned U.S. Pat. No. 5,718,360 to Green et al., the contents of which are incorporated herein by reference.

As best depicted in FIGS. 3–4, anvil delivery member 14 further includes pivot rod 54 which extends through guide member 12 and engages anvil head 44 of anvil 32 as shown. In a preferred arrangement, pivot rod 54 includes a hooked portion 56 which engages a corresponding dimensioned receiving groove 58 disposed within anvil head 44. Other means for connecting anvil head 44 and pivot rod 54 are envisioned as well. Pivot rod 54 is sufficient in length to extend from the stomach through the esophagus to be manipulated by the surgeon. Pivot rod 54 is longitudinally moveable between a retracted position and an extended position to selectively pivot anvil 32 at desired orientations.

In the assembled condition of anvil delivery member 14 within guide member 12, the outer margin of anvil head 44 is received within internal groove 24 of the guide member 12 to retain anvil 32 at the desired position mounted within the guide member 32. It is appreciated that groove 24 may be eliminated whereby anvil 32 may be fixed within guide member 12 by frictional engagement of anvil head 44 with the inner wall surface of the guide member 12.

Referring now to FIGS. 5–6, there is illustrated additional instrumentation utilized to perform the method in accordance with the principles of the present disclosure.

FIG. 5 illustrates a circular or end to end anastomosis instrument. This instrument 100 is marketed under the name PREMIUM CEEA™ manufactured by U.S. Surgical Corporation, of Norwalk, Conn. and is the subject of commonly assigned U.S. Pat. No. 5,119,983, the contents of which are incorporated herein by reference. This instrument 100 includes an elongated shaft 102 having a handle portion 104 at a proximal end to actuate the instrument and a staple holding component 106 disposed at a distal end. An anvil component such as anvil 32 described above is mountable to the distal end. Opposed end portions of the organs to be stapled are clamped between the anvil head 44 and the staple holding component 106. The clamped tissue is stapled by driving one or more staples from the staple holding component 106 so that the ends of the staples pass through the tissue and are clinched by the anvil head 44. In some applications of the circular anastomosis procedure, the anvil rod 46 with attached anvil head 44 is mounted to the distal end of the shaft 102 prior to insertion of the instrument into the tissue to be anastomised. However, in other applications and in accordance with the preferred method of the present disclosure, it is preferable to utilize a detachable anvil 32 which may be mounted to the instrument subsequent to positioning of the instrument and the anvil component within their respective tissue sections. In such instances, the stapling instrument and the anvil 32 are separately applied to the operative site. Each tissue section is then secured to their respective anvil 32 or staple holding component 106 by a purse string. The anvil 32 is mounted to the surgical instrument by inserting anvil rod 46 of the anvil 32 within the distal end of the instrument so that a mounting mechanism within the instrument securely engages the rod 46.

FIG. 6 illustrates an endoscopic linear surgical stapling apparatus marketed under the name ENDO GIA™ manufactured by U.S. Surgical Corporation of Norwalk, Conn. and is the subject of commonly assigned U.S. Pat. No. 5,894,979, the contents of which are incorporated herein by reference. This instrument 200 is adapted to place a plurality of longitudinal or linear rows of staples and may further include a knife for making an incision in body tissue between the rows of staples. The instrument 200 includes a frame 202 and an elongated tubular member 204 mounted to the frame 202. Mounted to the distal end portion of the tubular member is a cartridge assembly 206 which houses a plurality of rows of staples. An anvil 208 is pivotally movable relative to the cartridge assembly 206 to position tissue therebetween. Upon activation, the staples are fired to be clinched by the anvil 208 while the knife severs the tissue between the adjacent rows of staples.

In FIGS. 7–16, the disclosure describes methods for performing a bypass procedure in a digestive system that is representative of accessing, preferably, laparoscopically, and connecting a first and a second digestive system tissue portion. The digestive system or tract as defined herein includes the mouth, pharynx, esophagus, stomach, duodenum and colon.

Figure 7:
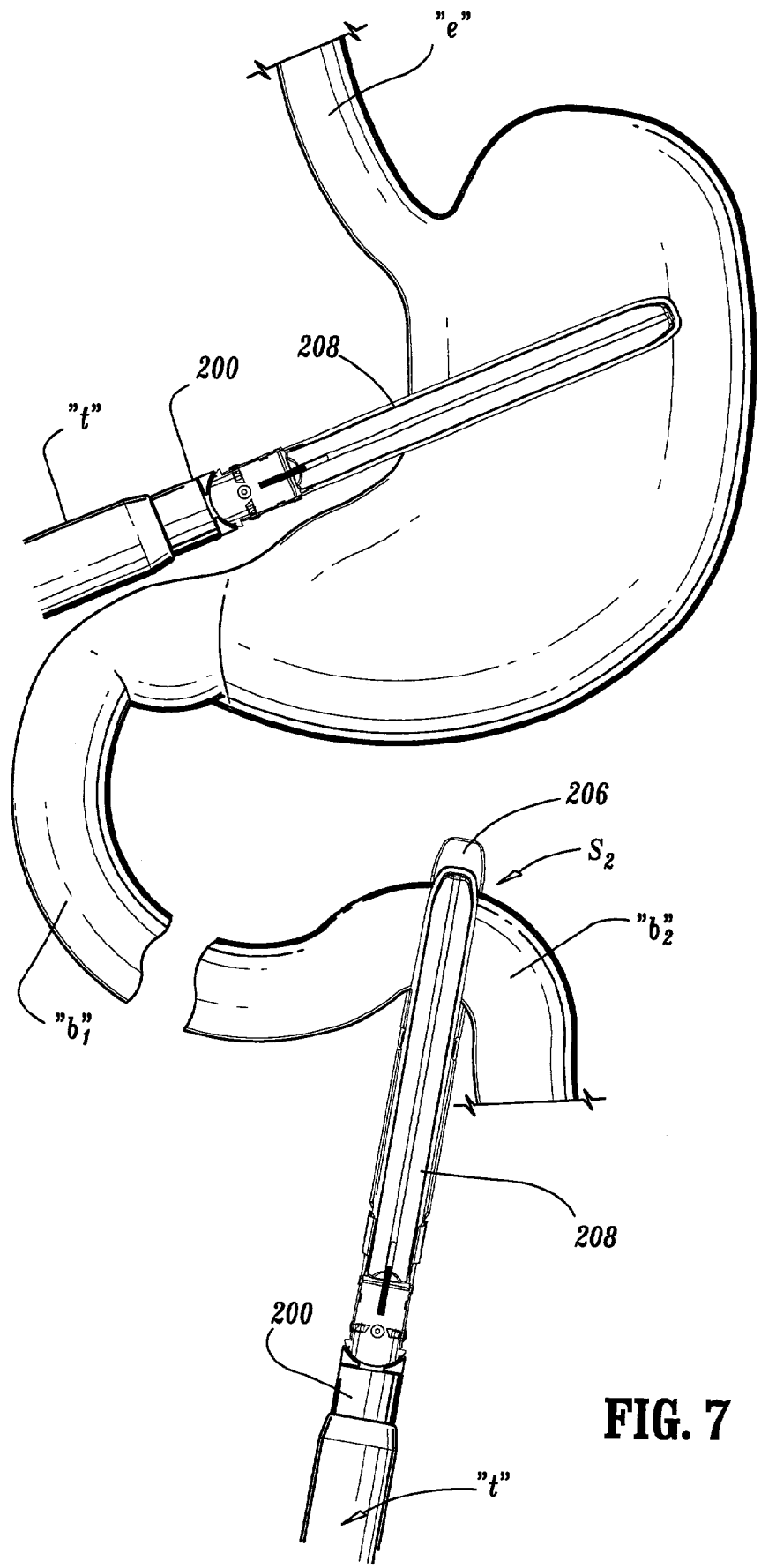
Figure 8:
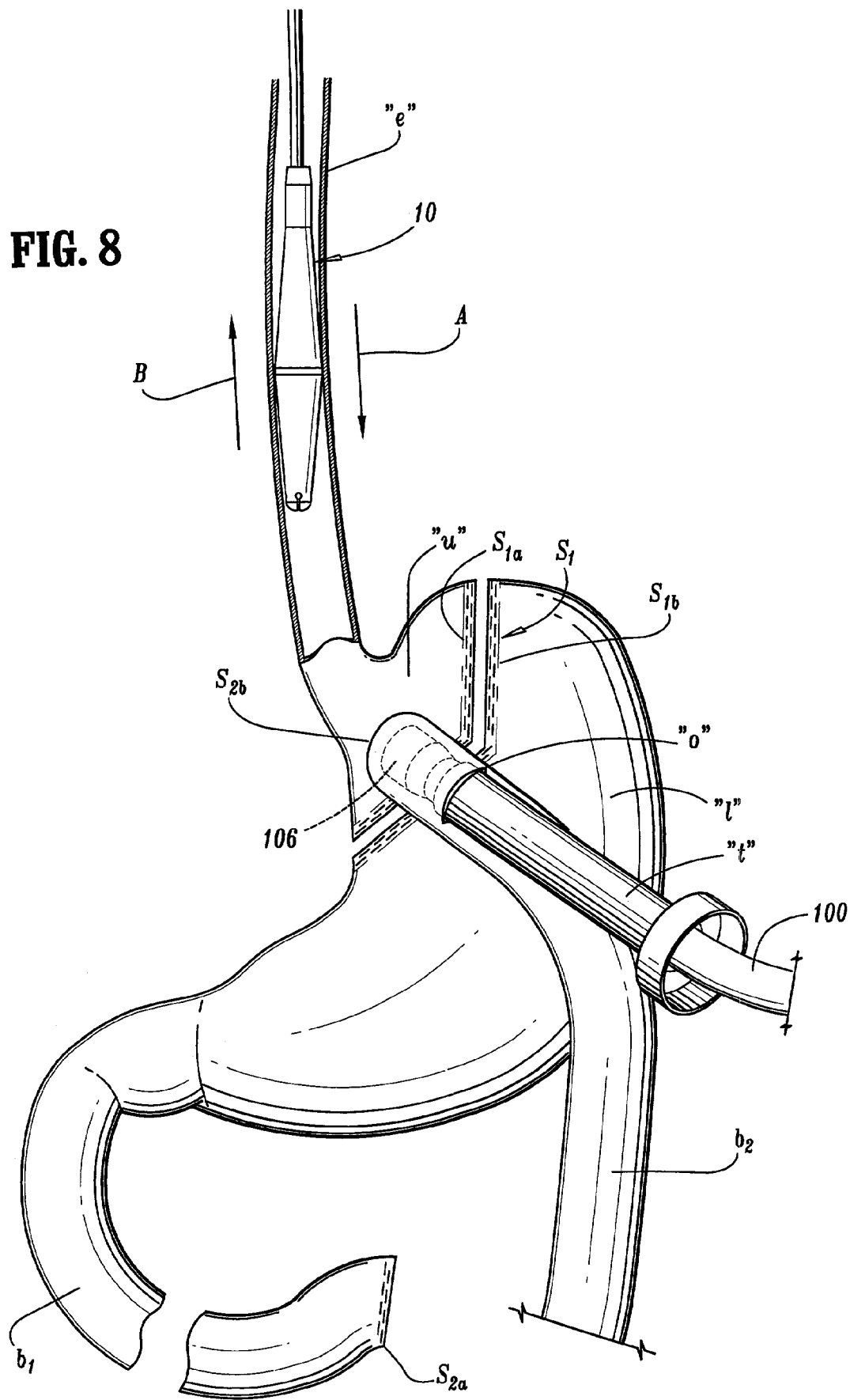

Referring now to FIGS. 7–16, by way of example, there is illustrated the preferred method for performing the laparoscopic gastric bypass procedure utilizing the aforedescribed instrumentation in accordance with the principles of the present disclosure. Initially, the peritoneal cavity is insufflated with insufflation gases which are introduced through a peritoneum needle of an insufflation apparatus, thus, distending the peritoneal lining and providing enhanced access therein. With reference now to FIG. 7, endoscopic linear stapling instrument 200 of FIG. 6 is introduced through a trocar "t" accessing the abdominal cavity. The instrument 200 is manipulated to position an upper portion of the stomach between the anvil 208 and the cartridge assembly 206. The instrument 200 is fired a first time whereby a first plurality of linear rows of staples are applied to the stomach portion at one angular orientation and then fired a second time at a second angular orientation to apply a second row of staples. As depicted in FIGS. 7–8, stapling instrument 200 preferably is arranged with respect to the esophageal tract to form a staple line $S_1$ which extends generally upwardly from the right side of the stomach to the left side (left to right with respect to the drawing). A knife blade incorporated within the instrument 200 removes or severs the tissue between adjacent rows of the staple line $S_1$. Thus, instrument 200 applied in the above-described manner forms an isolated upper stomach section "u" detached from the remaining lower section "l" of the stomach with both the upper and lower stomach sections "u, l" being closed by respective stapled rows $S_{1a}$ and $S_{1b}$ (FIG. 8). Alternatively, it is envisioned that the upper stomach section "u" may remain attached to the remaining stomach portion by use of stapling instrument 200 which is devoid of a knife blade.

With reference again to FIG. 7, the linear stapling instrument 200 is then positioned adjacent the small bowel through a trocar "t" in the lower part of the abdomen. Preferably, the instrument 200 is positioned adjacent an intermediate portion of the small bowel approximately 5–15 inches from the duodenum "d". The instrument 200 is fired to apply staples to form a staple line $S_2$ and preferably incise the bowel portion to thereby form a first bowel portion "$b_1$" connected to the stomach and a second bowel portion "$b_2$" which is connected to the remainder of the intestinal tract. The ends of the first and second bowel portions "$b_1$", "$b_2$" are closed with respective linear rows of staples $S_{2a}$ and $S_{2b}$ (FIG. 8).

Referring particularly to FIG. 8, apparatus 10 is inserted within the esophagus "e" of the patient and advanced in the direction "A" within the now formed upper stomach portion "u". The small bowel portion "$b_2$" is manipulated towards the upper stomach section "u". Preferably, a conventional grasping instrument introduced through trocar sleeve "t" accessing the stomach is utilized to manipulate the bowel portion "$b_2$" to the desired position. The circular anastomosis instrument 100 (FIG. 5) is inserted through the trocar "t" positioned adjacent the upper stomach portion "u" and positioned within a previously formed opening "o" in the bowel portion "$b_2$" made preferably with a conventional laparoscopic resecting instrument inserted within the trocar. The distal end of the circular anastomosis instrument 100 is thereafter advanced within the opening "o" such that the staple holding component 106 is disposed within the lumen of the bowel portion "$b_2$".

With reference now to FIGS. 9–10, anvil 32 is manipulated and then pivoted by advancing pivot rod 54 from the position shown in FIG. 9 to the position shown in FIG. 10, as desired, to position anvil rod 46 at a desired orientation for connection to instrument 100. As indicated above, anvil 32 is pivotal through an approximately 90° range of motion while guide member 12 is sufficiently flexible to permit such pivotal movement. As appreciated, guide member 12 protects the interior of the stomach from the anvil during pivotal movement of anvil 32 relative to the support member 30.

Figure 11:
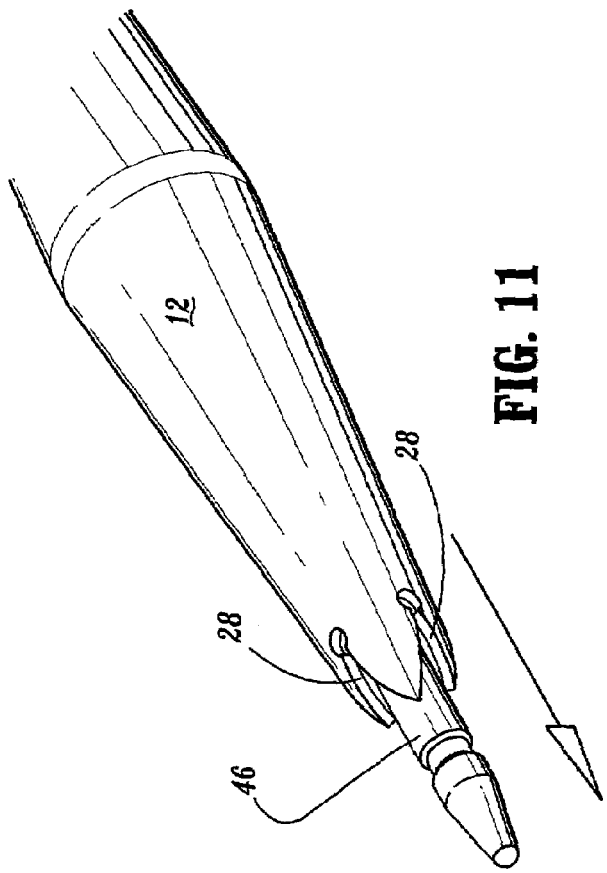
Figure 12:
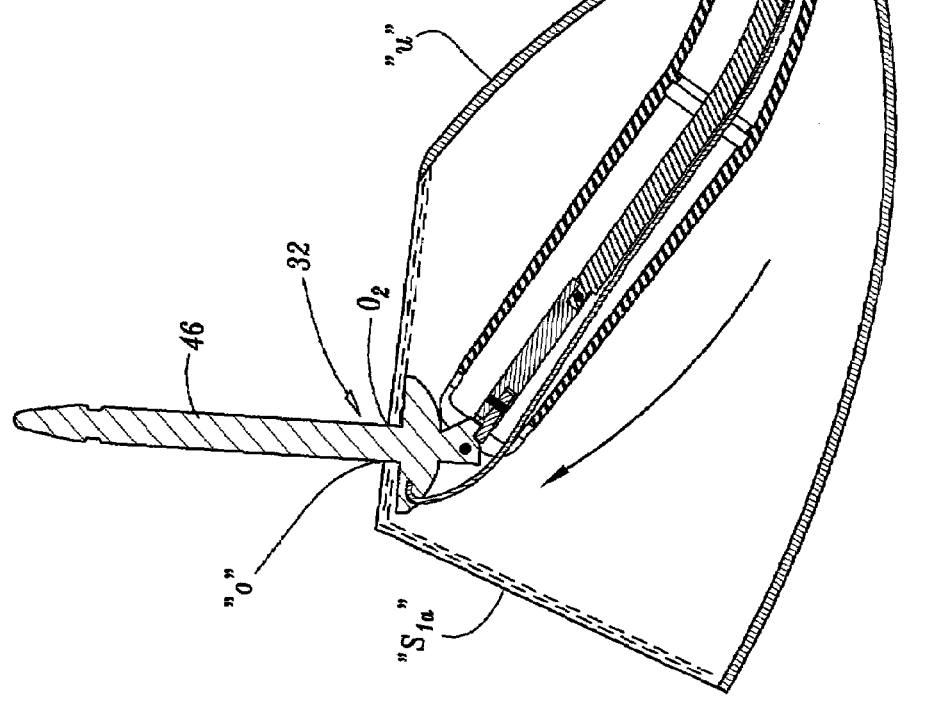

With reference now to FIGS. 11–12, support member 30 of instrument 10 is longitudinally advanced to advance anvil 32 within guide member 12 to expose the end portion of anvil rod 46 of anvil 32 from the guide member 12. During such movement, slits 28 in the outer wall of guide member 12 (FIG. 2) permit the outer wall to deflect outwardly to enable anvil rod 46 to pass through opening 26. Thereafter, anvil rod 46 can be grasped with conventional forceps inserted through a trocar accessing the cavity and advanced through an opening "$o_2$" formed by conventional means in the upper stomach portion "u" to the position shown in FIG. 12. The forceps may be introduced through the opening "o" (FIG. 8) created in the bowel portion "$b_1$" and maneuvered to grasp anvil rod 46 and pull the anvil rod 46 through the opening. In accordance with this procedure, the staple holding component 106 of the instrument 100 is introduced within the opening "o" after accessing anvil rod 46 of anvil rod 32. It is also envisioned that anvil rod 46 may include a sharpened tip which is manipulated to pierce the stomach tissue to connect to the circular anastomosis instrument 100. Alternatively, the sharpened anvil rod 46 may be passed through the staple lines $S_{1a}$, $S_{2b}$.

With reference now to FIGS. 13–14, anvil rod 46 is grasped with conventional forceps inserted through a trocar (not shown) and positioned such that anvil rod 46 is adjacent the circular anastomosis instrument 100. Thereafter, anvil rod 46 is inserted within the circular anastomosis instrument 100 to be mechanically coupled therewith. Anvil rod 46 is thereafter approximated as is conventional and the instrument is fired. As a result of the firing of the instrument 100, a circular array of staples are advanced through the bowel section "b$_2$" and upper stomach tissue to join the marginal tissue portions of the upper portion "u" and the small bowel portion "b$_2$". In addition, a circular knife of the anastomosis instrument 100 defines an annular opening between the tissue sections to fluidly connect the interior of the upper stomach portion "u" and the lumen of the bowel portion "b$_2$". Thereafter, the anvil 34 is detached from the circular anastomosis instrument 100 and the delivery instrument with attached anvil 32 is removed through the esophagus "e", i.e., in the direction "B" opposite to the insertion direction "A" shown in FIG. 8.

Figure 15:
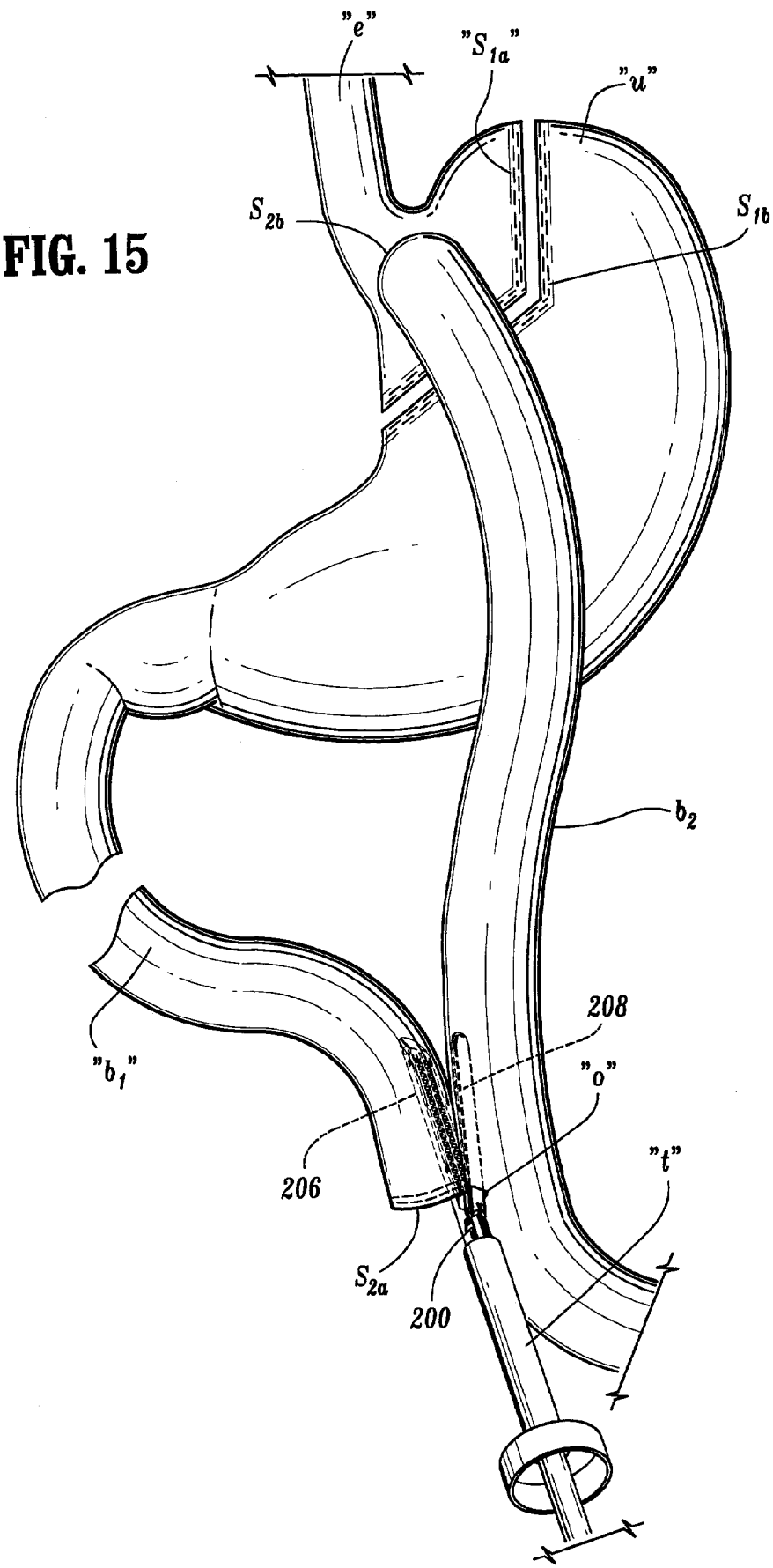

With reference now to FIG. 15, attention is now directed to rejoining the bowel sections "b$_1$", "b$_2$". In one preferred method, bowel sections "b$_1$", "b$_2$" are positioned in juxtaposed side by side relation and joined with the use of the linear stapler instrument 200 of FIG. 6. Specifically, the instrument 200 is introduced within a trocar "t" accessing the abdominal area. Thereafter, cartridge assembly 206 is introduced within the end of bowel section "b$_1$" through the staple line S$_{2a}$. An opening "o" is made in the wall of bowel section "b$_2$" followed by insertion of anvil 208 within the opening "o" and into the lumen of bowel section "b$_2$". The instrument 200 is approximated and fired to connect the bowel sections "b$_1$", "b$_2$" with rows of staples whereby the knife blade severs tissue between adjacent staple rows to connect the lumens of the bowel sections "b$_1$", "b$_2$". The instrument 200 is removed and the opening in the wall of the bowel section "b$_2$" is closed.

Figure 16:
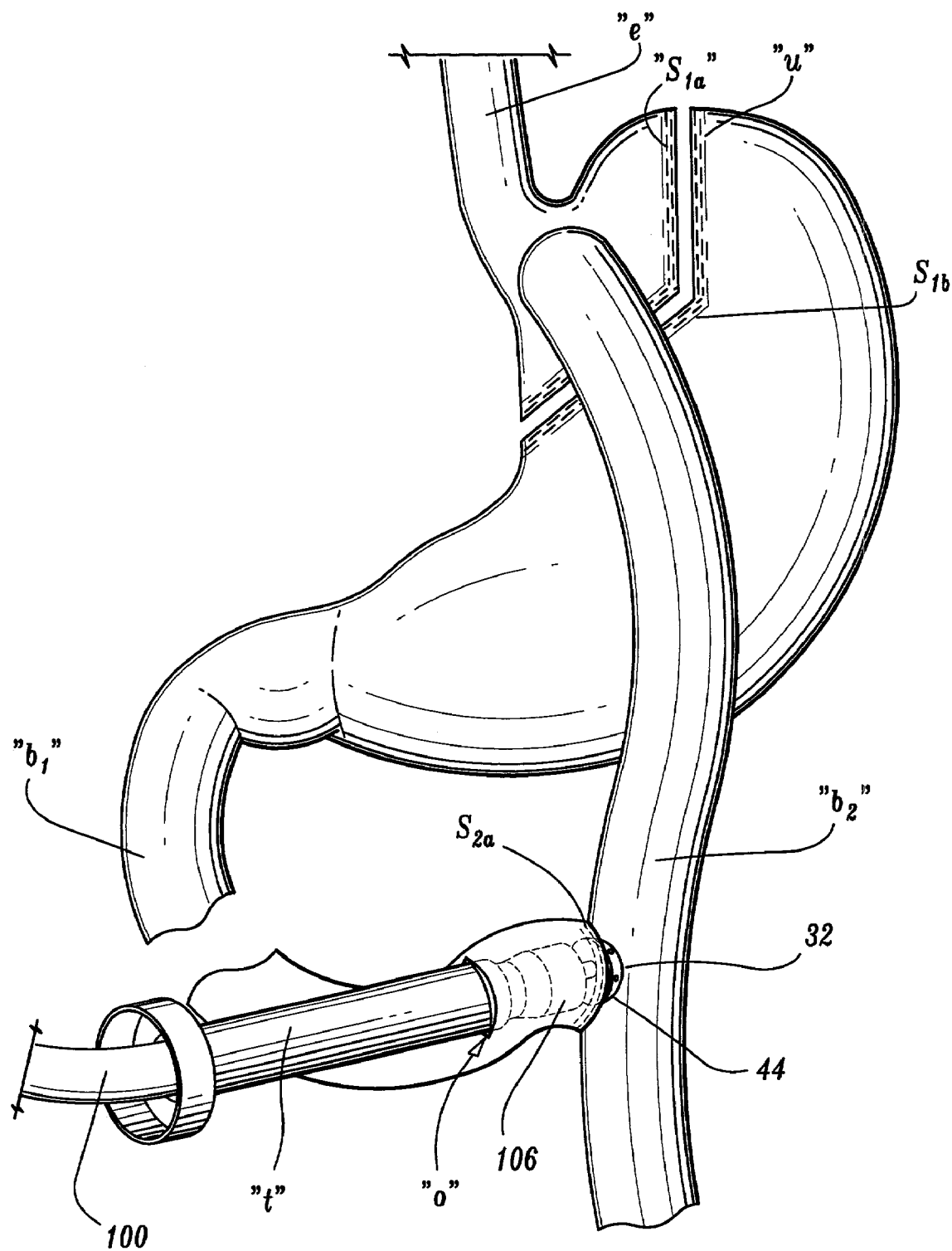

In an alternate procedure depicted in FIG. 16, the circular anastomosis instrument 100 of FIG. 5 is positioned through a trocar "t" accessing the abdominal cavity. The closed stapled end "S$_{2a}$" of bowel section "b$_1$" is positioned against the wall of bowel section "b$_2$". Thereafter, an access opening "o" is formed in one of the bowel sections, e.g., bowel section "b$_1$", and the staple holding component 106 with mounted anvil 32 is introduced within the opening "o". The instrument 100 is advanced to pass the anvil head 44 through an opening formed (by conventional techniques) in the bowel section "b$_2$" to position the anvil head 44 within the lumen of the bowel section "b$_2$". Anvil head 44 is thereafter approximated and the instrument 100 is fired to join the marginal tissue portions of bowel sections "b$_1$", "b$_2$" while the circular knife of the instrument 100 resects the tissue to connect the respective lumens of the sections "b$_1$", "b$_2$".

Thus, in accordance with the apparatus and method of the present disclosure, the stomach is reduced significantly in size while the normal digestive path of the intestinal tract is maintained thereby providing an effective treatment for obesity. The preferred surgical approach is minimally invasive which significantly reduces patient trauma and recovery time.

Figure 17:
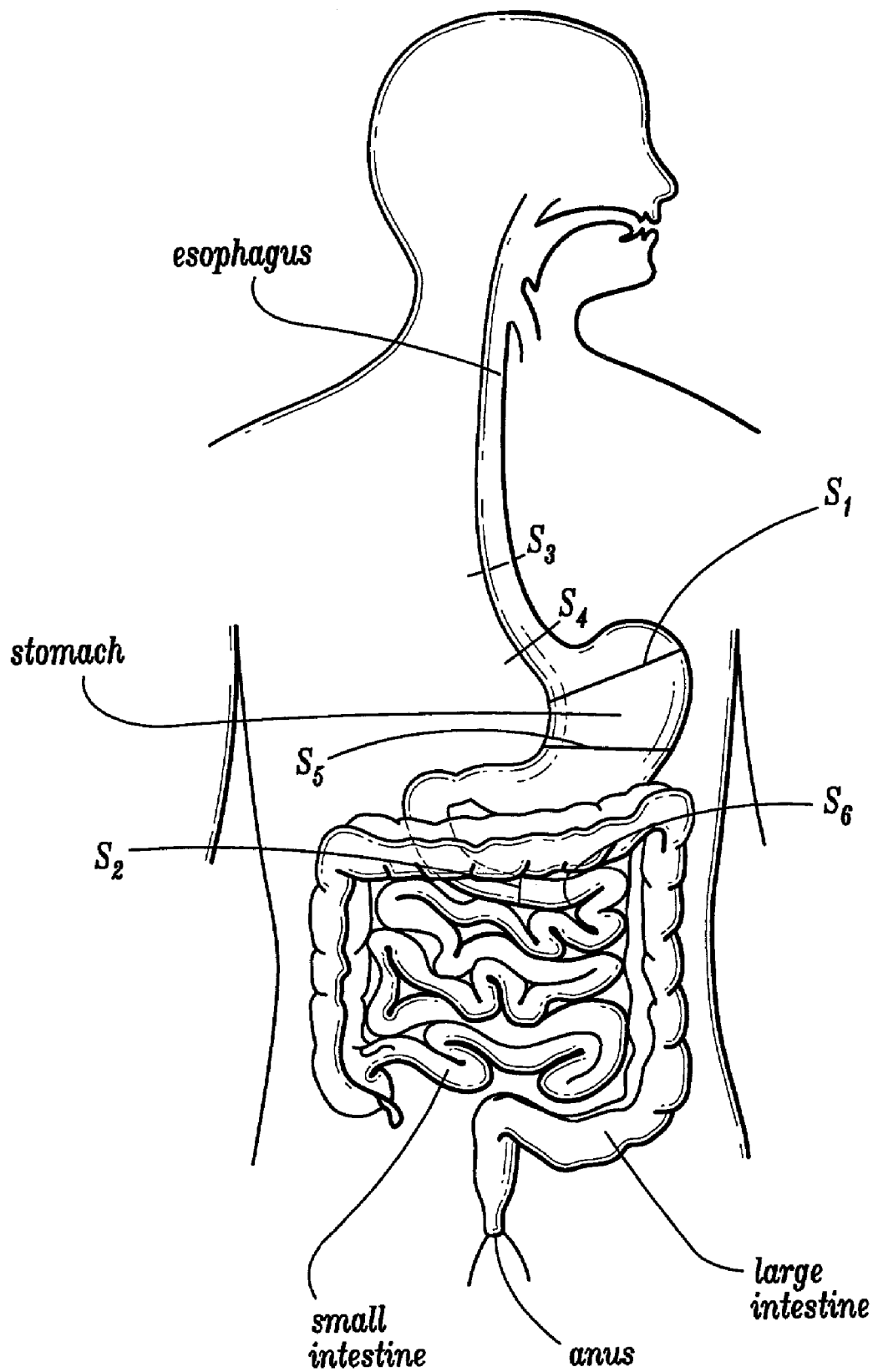
FIG. 17 is a view of a portion of a-digestive system with staple and resection lines in connection with alternate bypass procedures to be conducted in accordance with the present disclosure.

Referring now to FIG. 17, alternative bypass procedures to be performed in the digestive system in accordance with the instrumentation and method of the present invention are illustrated. In addition to the aforementioned gastric bypass procedure connecting the upper stomach section "u" adjacent staple line S$_1$ with the small bowel adjacent staple line S$_2$, described in connection with FIGS. 7–16, other preferred bypass procedures are envisioned. For example, it is envisioned that a portion of the esophagus and stomach may be resected adjacent staple lines S$_4$, S$_5$, respectively and subsequently rejoined adjacent the staple lines S$_4$,S$_5$ in a bypass procedure. More specifically, a staple line S$_5$ is formed within the intermediate stomach section in the manner as discussed above in connection with FIGS. 7–15. Another staple line S$_4$ is formed at the lower end of the esophagus. This staple line S$_4$ may be created through a trocar and with the stapling instrument 200 of FIG. 6 in a manner similar to that described above. The resected esophageal and stomach tissue (i.e., between the staple lines S$_4$, S$_5$) is removed. Apparatus 10 is introduced into the esophagus and the anvil 32 is deployed and manipulated through an opening (not shown) adjacent staple line S$_5$. The circular anastomosis instrument 100 is then introduced into the stomach portion below staple line S$_5$ followed by connection of the anastomosis instrument 100 and the anvil 32 as discussed above. The tissue is approximated and the instrument is fired to connect the esophageal section adjacent staple line S$_4$ with the stomach section adjacent staple line S$_5$. Anvil 32 is then disconnected from anastomosis instrument 100 and removed, thereby completing the procedure.

One skilled in the art may readily adapt the preferred method of performing additional bypass procedures in the digestive system which includes, but is not limited to connecting a stomach section defined by staple lines S$_1$ or S$_5$ to an intestinal section defined by staples lines S$_2$ or S$_6$; connecting an esophageal section defined by staple lines S$_3$ or S$_4$ to a stomach section defined along staple lines S$_1$ or S$_5$; connecting an esophageal section along staple lines S$_3$ or S$_4$ to an intestinal section defined along staple lines S$_2$ or S$_6$.; or connecting stomach sections along staple lines S$_1$,S$_5$. While staple lines S$_1$–S$_6$ are shown as precise lines, it understand that their positions in FIG. 16 are representative, for the purposes of illustrating the bypass procedure in a digestive system, and are capable of being modified within that procedure for each individual application by one skilled in the art. Similarly, the anastomosis instrument 100, endoscopic linear stapling instrument 200, and anvil 32 are representative instruments that can be substituted for by one or more similar devices that perform similar functions.

Figure 18:
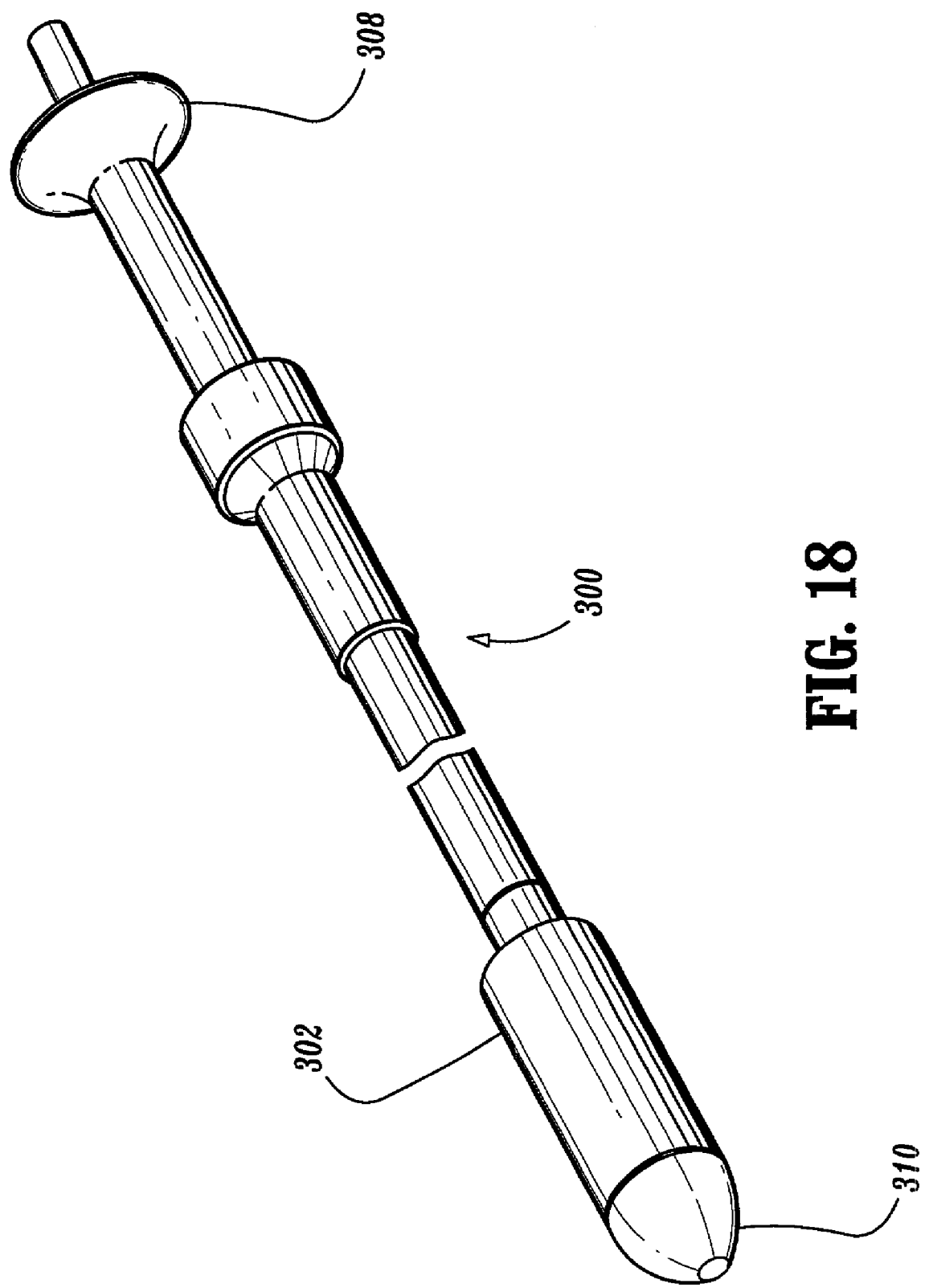
FIG. 18 is a perspective view of an alternate embodiment of the apparatus of FIG. 1.
Figure 19:
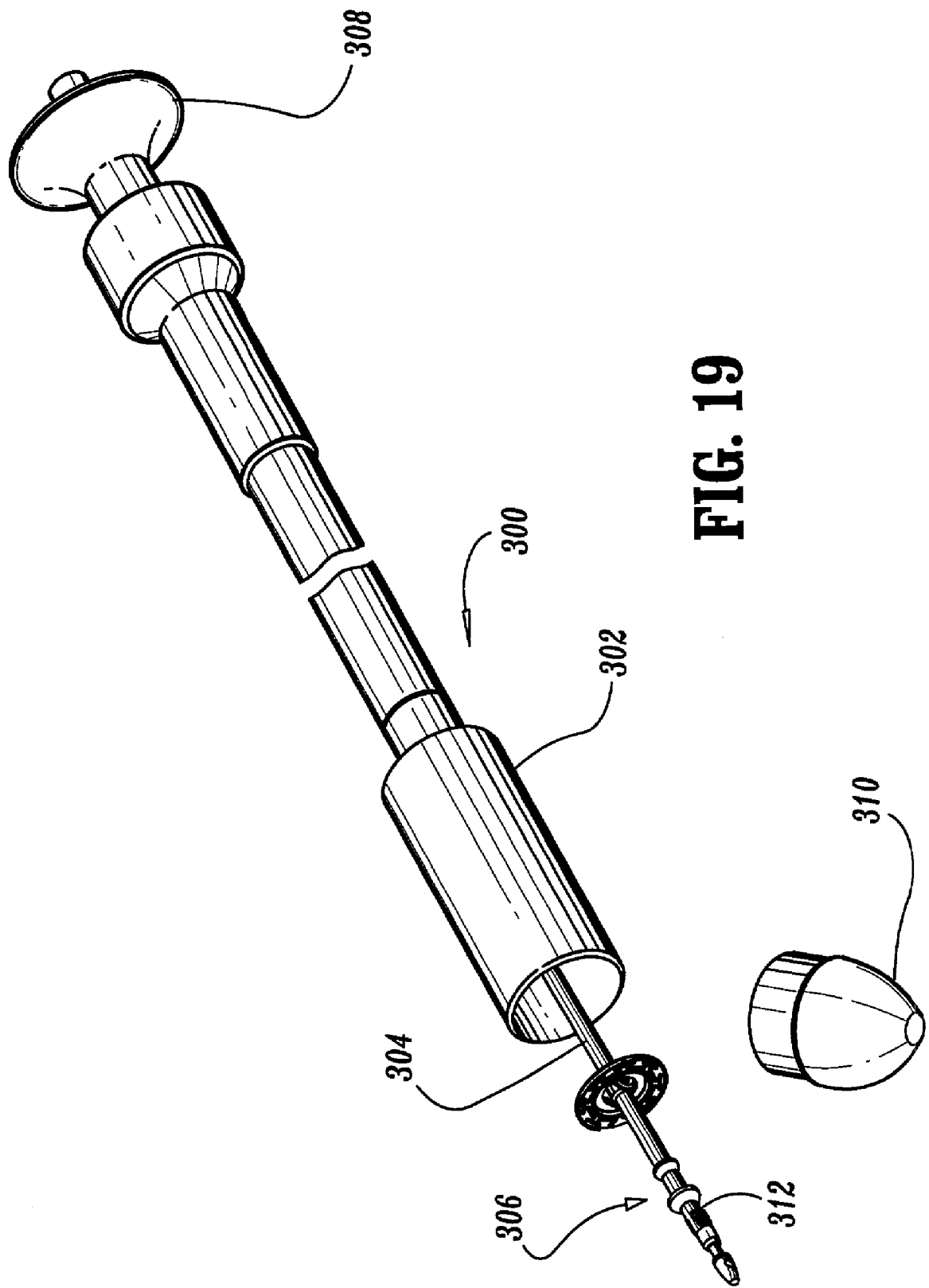
FIG. 19 is a perspective view of the apparatus of FIG. 18 in an actuated position.

Referring now to FIGS. 18–19, there is illustrated an alternate embodiment of the apparatus 10 of FIGS. 1–4, for delivering an anvil in conjunction with the laparoscopic digestive bypass procedure of the present disclosure. Apparatus 300 includes an outer sheath 302, anvil delivery member 304 disposed within the outer sheath 302 and an anvil component 306 mounted within the outer sheath 302. Delivery member 304 includes proximal disc-shaped handle 308 which is advanced to move anvil component 306 between an initial position (FIG. 18) disposed within outer sheath 302, and an advanced position (FIG. 19) where the anvil 306 is fully ejected from the outer sheath 302.

Apparatus 300 further includes a bull-nosed shaped cap 310 which is mounted to the proximal end of anvil rod 312 to cover the anvil rod 312 during passage through the esophagus. Cap 310 is preferably fabricated from a bioabsorbable polymer such that subsequent to deployment of anvil component 306 from outer sheath 302, the cap 310 may be removed from anvil rod 312 to be left for absorption into the body.

Figure 20:
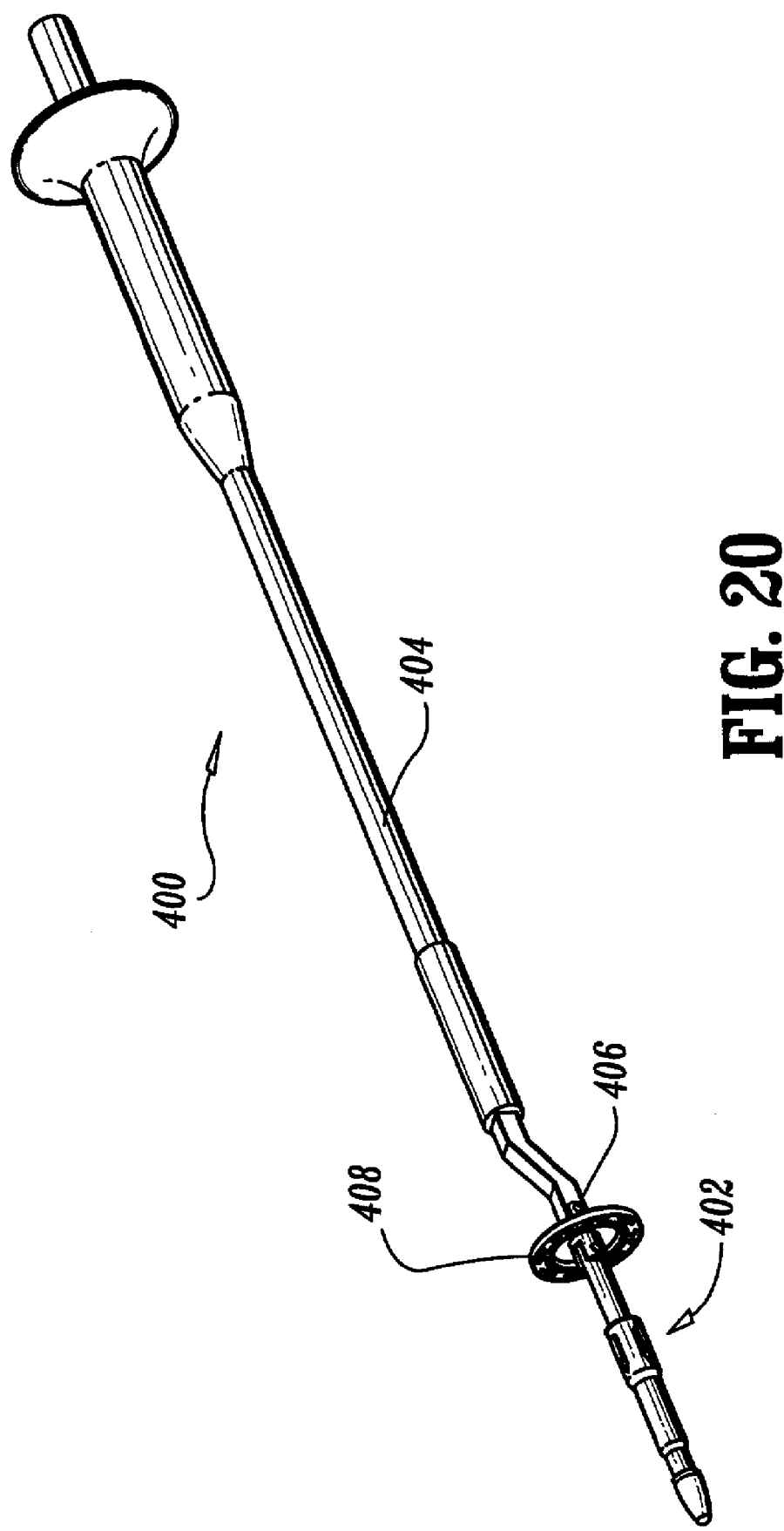
FIG. 20 is a perspective view of another alternate embodiment of the apparatus of FIG. 1.
Figure 21:
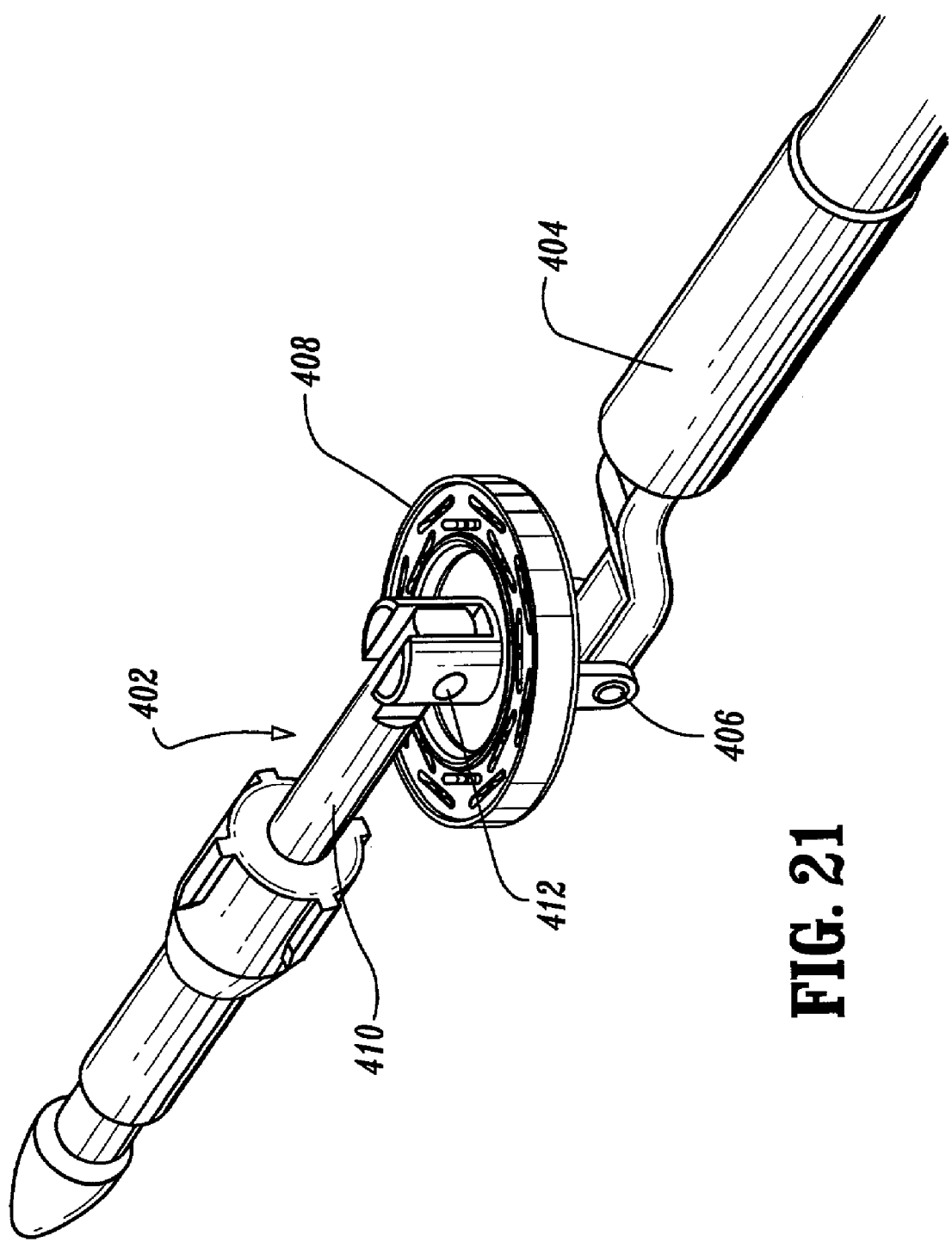
FIG. 21 is a perspective view of the distal end of the apparatus of FIG. 20 illustrating the anvil in an inoperative position.
Figure 22:
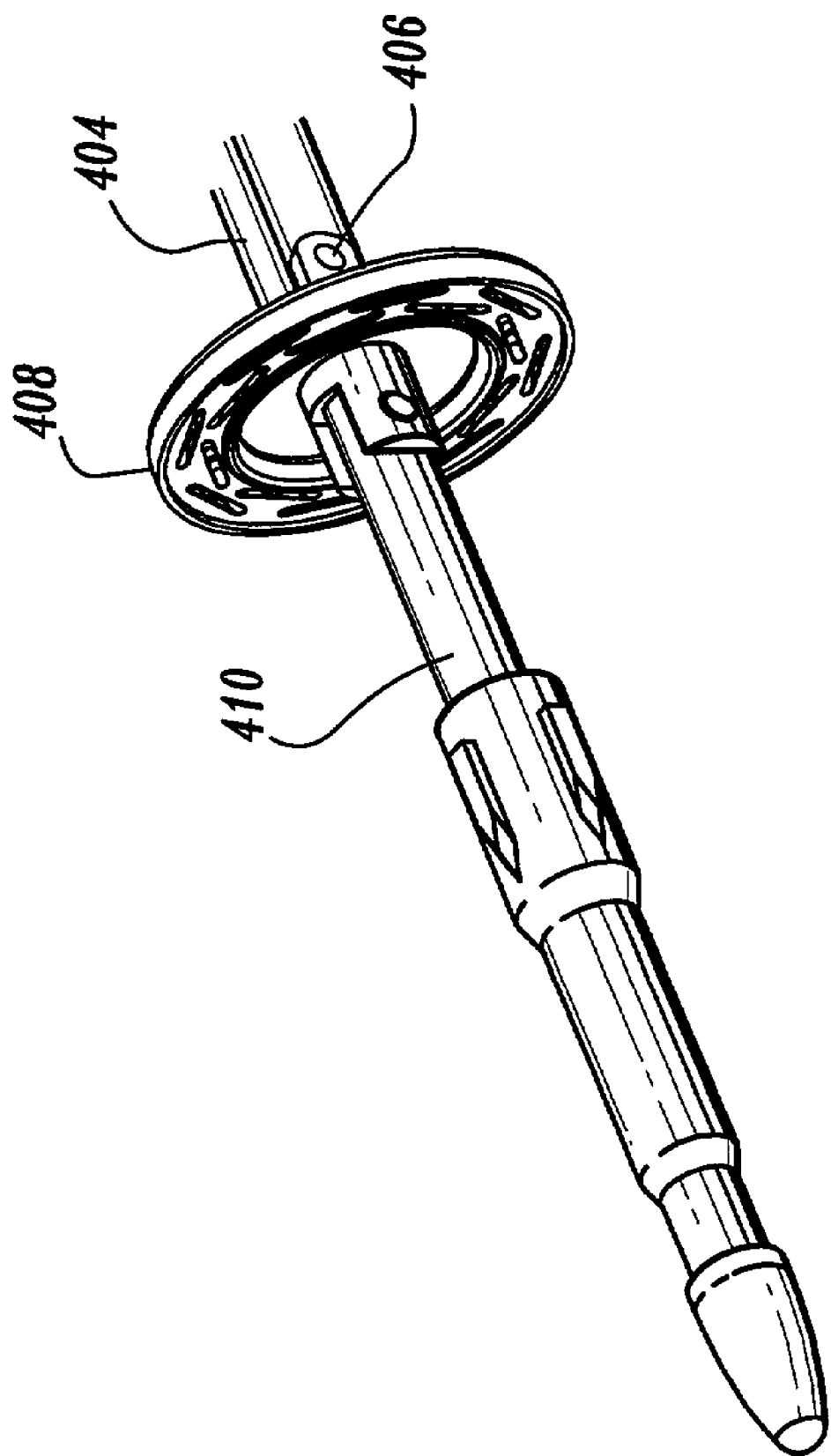
FIG. 22 is a perspective view of the distal end of the apparatus of FIG. 20 illustrating the anvil in an operative position.

Referring now to FIGS. 20–22, there is illustrated another alternate embodiment of the apparatus 10 of FIG. 1. In accordance with this embodiment, apparatus 400 includes an anvil component 402 which is pivotally mounted to delivery member 404 through pivot connection 406 thereby providing a pivotal range of motion of approximately 180°. In addition, anvil head 408 of anvil component 402 is pivotally mounted to anvil rod 410 through pivot pin 412 and thus pivots relative to anvil rod 410 through a 180° range of motion. This facilitates positioning of anvil component 402 relative to the end to end anastomosis instrument 100. In addition, this arrangement significantly reduces the overall profile of anvil component 402 thereby enhancing ejection of the anvil component 402 from the outer sheath (not shown) and passage through the esophageal tract. In particular, when positioned in the outer sheath (not shown), anvil head 408 is in the arrangement of FIG. 21 pivoted in a non-operative position, i.e., ninety degrees (90°), with respect to the axis of anvil rod 410. Subject to deployment in the desired digestive tissue, e.g., the upper stomach section "u", anvil component 402 is mounted to the anastomosis instrument 100 of FIG. 5 in the aforedescribed manner. Thereafter, anvil head 408 is pivoted to the proper operative orientation (FIG. 22) with respect to the staple holding component 106 of the circular anastomosis instrument 100 by pulling delivery member 404 in the proximal direction.

Referring now to FIGS. 23–28, there is illustrated another alternate embodiment of the apparatus for performing a laparoscopic gastric bypass procedure in accordance with the principles of the present disclosure. Apparatus 500 may include outer sheath or guide member (not shown) which may be similar to the configuration of the outer guide 12 of the apparatus 10 of FIG. 1 or the configuration of the outer sheath 302 of the apparatus of FIG. 18. Alternatively, and in the preferred embodiment, no outer sheath is incorporated in apparatus 500. Apparatus 500 further includes delivery member 502 defining longitudinal opening 504, pivot element 506 at least partially disposed within the longitudinal opening 504 and anvil component 508 connected to the delivery member 502. Delivery member 502 defines disc-shaped handle 510 at its proximal end which is advantageously dimensioned for engagement by the user. Delivery member 502 and pivot element 506 are preferably sufficient in length to extend from the upper stomach section through the esophageal tract and out the mouth or oral cavity.

Pivot element 506 includes manually engageable portion or button 512 at its proximal end and pivot link 514 which is connected to the button 512 and extends distally therefrom. Pivot link 514 is connected to the anvil head 516 of anvil component 508 through pin 518. In the preferred embodiment, 506 pivot element includes proximal and distal link portions 506a, 506b connected to each other through pin 520, however, it is envisioned that pivot element 506 may be a single component.

Pivot element 506 is adapted for reciprocal longitudinal movement within delivery member 502 between an initial position (FIG. 25) and an actuated (or retracted) position to cause corresponding pivotal movement of the anvil head 516 of the anvil component 508. Pivot element 506 is normally biased to the actuated position by coil spring 522. Coil spring 522 is mounted within the interior of disc-shaped handle 510 and engages at one end, interior wall surface 524 of the handle 510 and, at its other end, abutment surface 526 of button 512. Pivot element 506 is releasably locked in its initial position against the bias of coil spring 522 by a locking mechanism. In the preferred embodiment, a locking ring 528 is mounted within a circumferential recess 530 at the proximal end of handle 510 of delivery member 502. Locking ring 528 defines an internal locking shelf 532. Similarly, button 512 of pivot element 506 includes a corresponding locking shelf 534 which engages the shelf 532 of locking ring 528 to releasably lock the pivot element 506 in the initial position. To release button 512, the button 512 is moved away from locking shelf in a radial direction, i.e., toward the left with respect to FIG. 24. It is noted that a sufficient clearance exists between the outer surface 536 of button 512 and the interior surface of locking ring 528 to permit such radial movement of the button 512. Once released, pivot element 506 moves rearwardly under the influence of coil spring 522 to cause the pivotal anvil head 516 of anvil component 508 to pivot to the operative position of FIG. 27.

With reference to FIG. 28, in conjunction with FIGS. 23–27, further details of anvil component 508 will be discussed. Anvil component 508 includes anvil rod 538 and the anvil head 516 pivotally mounted to the anvil rod 538 through pivot pin 540. Anvil head 516 is arranged in oblique relation relative to the axis of the delivery member 502 when in the initial position of the pivot element 506. Such arrangement significantly reduces the overall profile of anvil component 508, thereby reducing the overall diameter requirement of the outer sheath. This significantly facilitates passage of the apparatus through the restricted lumen of the esophageal tract.

Anvil component 508 has an adapter assembly 542 mounted to the end of the anvil rod 538 opposite anvil head 516. Adapter assembly 542 includes an adapter rod 544 defining a longitudinal opening 546 at one end to receive anvil rod 538 of anvil component 508. Preferably, the longitudinal opening 546 of adapter assembly 542 is correspondingly dimensioned such that the assembly 542 forms a snap-fit about the entrance end of anvil rod 538 to mount the anvil rod 538 to the adapter assembly 542. Adapter assembly 542 is preferably connected to the anastomosis instrument 100 (FIG. 5) and then is subsequently connected to anvil component 508 after the instruments have been introduced into the surgical site, i.e., adapter assembly 542 is not connected to anvil component 508 prior to introduction of the instrument 500 into the esophagus. It is noted that in FIGS. 23–28 adapter 542 is shown mounted to anvil rod 538 for illustrative purposes. Alternatively, the anvil adapter 542 may be first attached to anvil rod 538 after introduction into the surgical site and then connected to the anastomosis instrument 100. The use of adapter assembly 542 permits anvil rod 538 to be significantly reduced in size and diameter, thereby facilitating passage of the instrument 500 and anvil component 508 through the esophagus, and manipulation about the surgical site. Further details of the adapter assembly will be discussed in connection with the embodiment of FIG. 29.

In use, in connection with the method of FIGS. 7–16, apparatus 500 with mounted anvil component 508 is introduced through the esophageal tract and advanced within the upper stomach section "u" (FIG. 8). Circular anastomosis instrument 100 with mounted adapter assembly 542 is introduced within bowel section "$b_2$" (FIG. 8). Anvil rod 538 is then connected to anvil adapter 542 in the aforedescribed manner. Alternatively, anvil adapter 542 is first connected to anvil rod 538 followed by connection of the anvil adapter 542 to the circular anastomosis instrument 100. Button 512 of instrument 500 is then released to permit pivoting element 506 to move proximally under the bias of coil spring 522. Upon proximal movement of pivot element 506, anvil head 516 pivots to its operative position (FIG. 27) whereby the anvil surface is transverse to anvil rod 538. Anvil component 508 and staple holding component 106 of instrument 100 are approximated and the instrument is fired to connect the tissue sections "$b_1$", "$b_2$". Upon completion, anvil rod 538 is disconnected from adapter assembly 542 and apparatus 100 with mounted anvil component 508 is removed through the esophageal tract. Prior to removal, anvil head 516 is preferably pivoted and locked in its non-operative position by depressing button 512.

Figure 29:
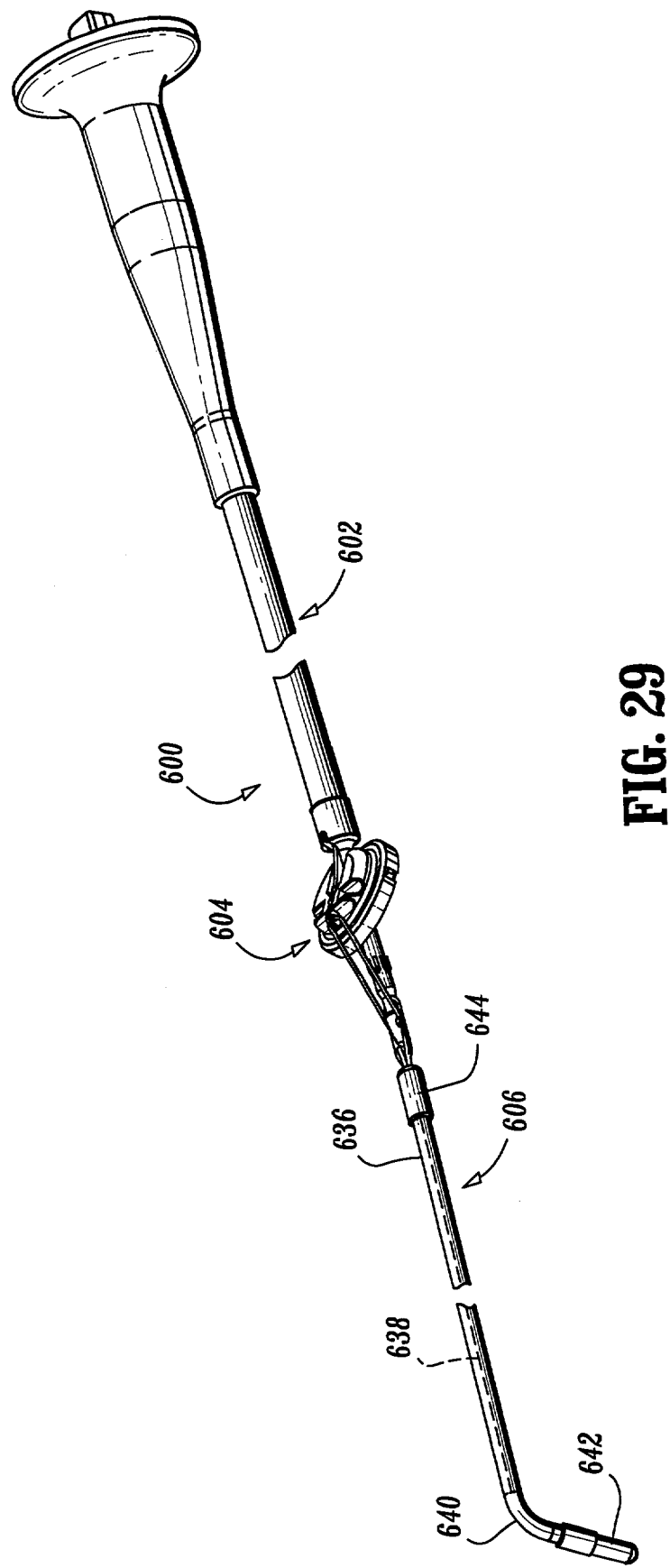
FIG. 29 is a perspective view of an alternate embodiment of the apparatus of the present disclosure illustrating the catheter guide, delivery apparatus, and mounted anvil assembly.
Figure 30:
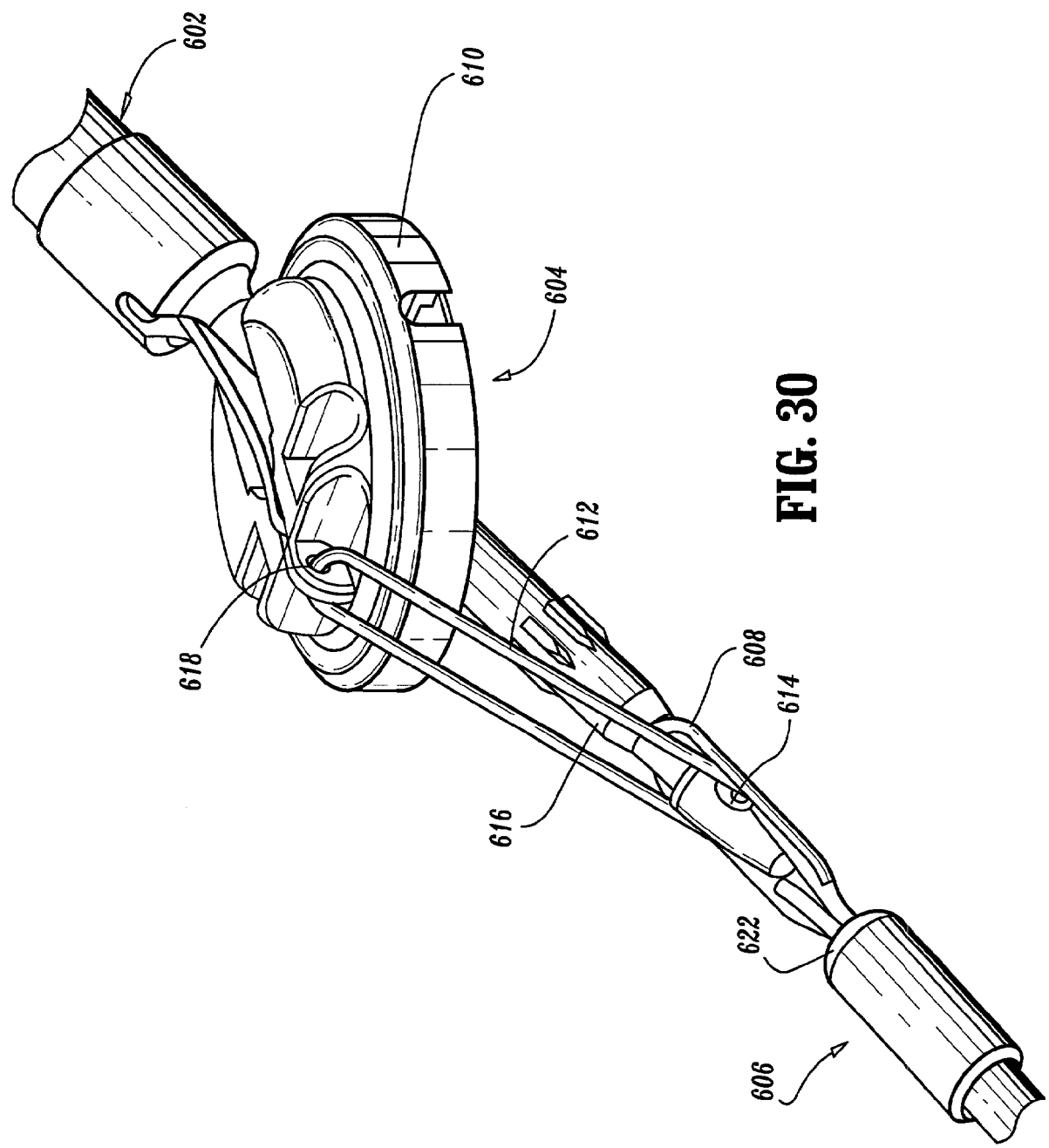
FIG. 30 is an enlarged perspective view of the anvil assembly mounted to the catheter guide and delivery apparatus.
Figure 31:
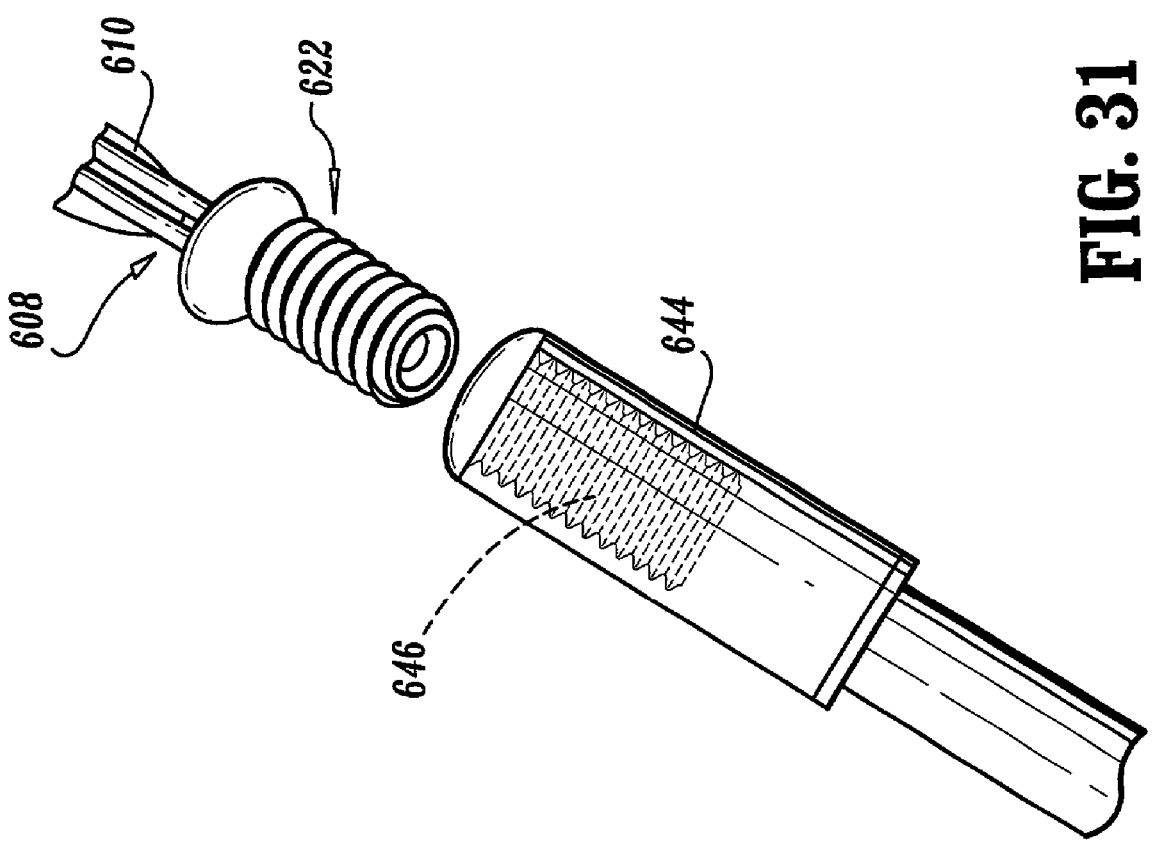
FIG. 31 is a perspective view illustrating connection of a suture unit of the anvil assembly to the catheter guide.

Referring now to FIG. 29, there is illustrated another alternate embodiment of the present disclosure. System 600 includes delivery instrument 602, anvil component 604 and catheter guide 606 which is releasably connected to the anvil component 604. Delivery apparatus 602 is substantially similar to the apparatus 500 described in connection with FIGS. 23–28, and reference is made thereto for the particulars of its operating mechanisms. Anvil component 604 is also similar to the anvil component 508 of FIGS. 23–28. However, in accordance with this embodiment and as best depicted in FIG. 30, anvil component 604 further includes suture unit 608. Suture unit 608 functions in connecting delivery instrument 102 with catheter guide 606. A suture 612 is passed through aperture 614 of anvil rod 616, through opening 618 in a depending surface of anvil head 610, and back through the aperture 614 of the anvil rod 616 in a race track arrangement. As depicted in FIGS. 30–31, the free ends of the suture 610 are connected by conventional means to an externally threaded collar 622 which is subsequently connected to catheter guide 606 as will be discussed. The suture 610 is sufficiently taut upon assembly so as to facilitate retention of the anvil head 610 in the pivoted non-operative position.

Figure 32A:
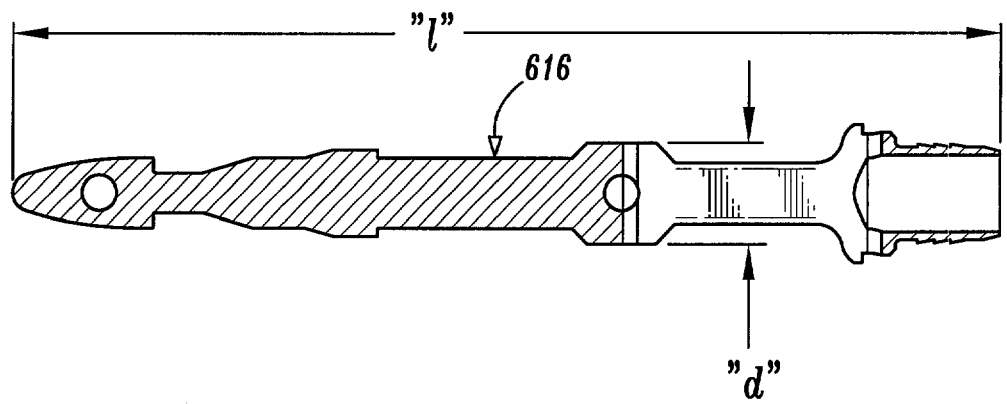
FIGS. 32A–32B are side plan and cross-sectional views of the anvil rod of the anvil assembly.
Figure 32B:
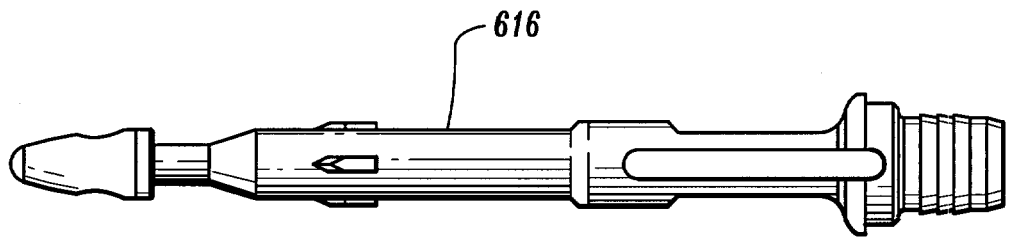

With reference to FIGS. 32A and 32B, anvil rod 616 is specifically adapted for non-invasive transport through the restricted esophageal passageway. More particularly, anvil rod 616 is substantially reduced in length and in cross-sectional dimension as compared to conventional anvil rods used with circular anastomosis instruments. The length "l" of anvil rod 616 ranges from about 1.50 inches to about 1.90 inches, and the maximum diameter "d" ranges from about 0.17 inches to about 0.21 inches. In the preferred embodiment, the length "l" is about 1.79 inches and the maximum diameter "d" is about 0.19 inches. This represents a reduction in length and diameter relative to a conventional anvil rod of about 45%, and about 57%, respectively.

Figure 33A:
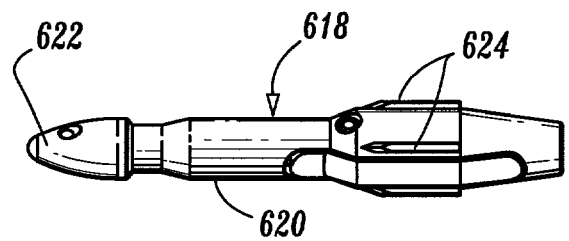
FIGS. 33A–33B are cross-sectional and side plan views of the anvil adapter.
Figure 33B:
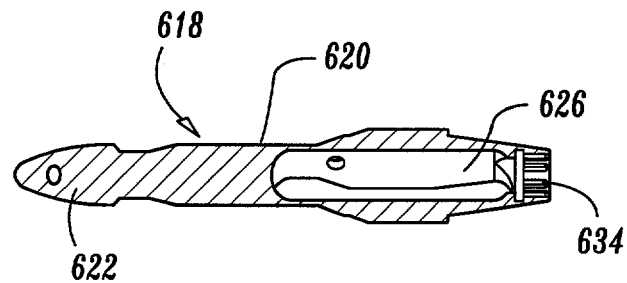
Figure 34:
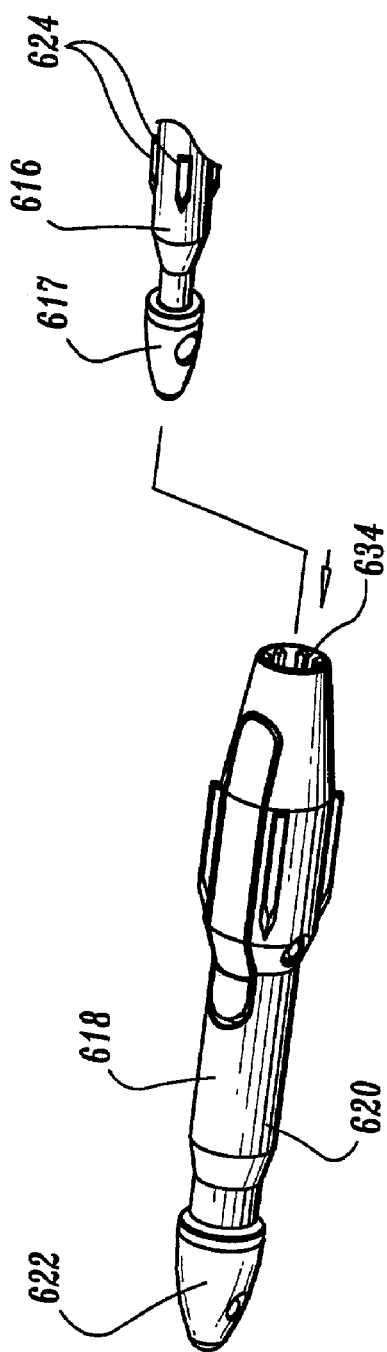
FIG. 34 is a perspective view illustrating mounting of the anvil rod to the anvil adapter.
Figure 35:
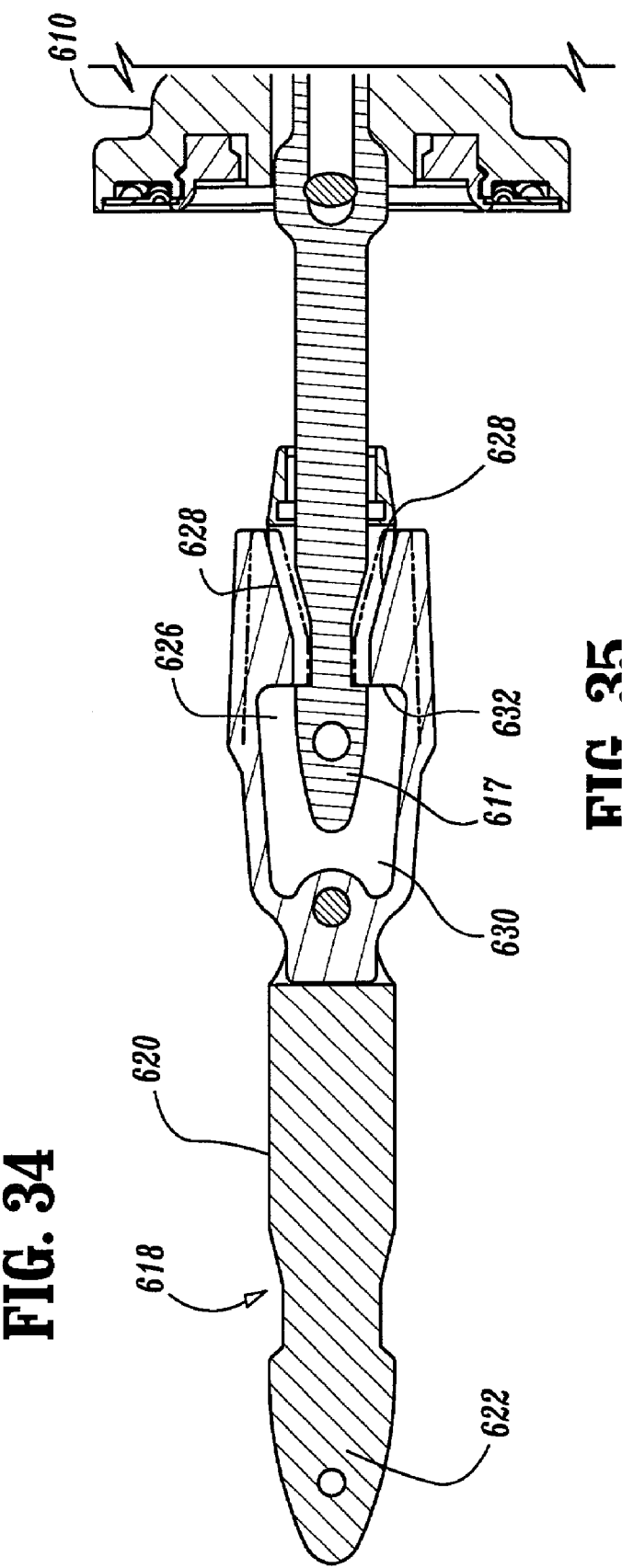
FIG. 35 is a cross-sectional view of the anvil assembly and mounted anvil adapter.

Anvil component 604 is coupled to the circular anastomosis instrument through anvil adapter 618. With reference to FIGS. 33–35, anvil adapter 618 includes adapter rod 620 having tapered mounting portion 622 at one end for connection to the circular anastomosis instrument and external splines 624 to engage corresponding internal splines/grooves of the circular anastomosis instrument 100. The connection of anvil adapter 618 is similar to the connection of the anvil to the USSC PREMIUM CEEA™ instrument as disclosed in U.S. Pat. Nos. 5,119,983 or 5,718,360. As best depicted in FIGS. 33–34, an axial opening 626 adjacent the second end of adapter rod 620 extends to an intermediate portion of the rod 620. The axial opening 626 is defined by inwardly tapered walls 628 which extend into an enlarged inner cavity 630 of the opening. The juncture of the tapered walls 628 and inner cavity 630 defines an abutment surface 632. A plurality of internal splines 634 are disposed adjacent the second end of anvil rod 616 and extend in a general longitudinal direction. Upon assembly of anvil rod 616 and adapter 620, the tapered portion 617 of anvil rod is inserted within axial opening 626 of the adapter 618. As the rod 616 is advanced in the adapter 618 and passed through the narrowed opening defined by inner tapered walls 628, the tapered walls 628 are biased outwardly in a spring-like manner to permit passage of the tapered mounting portion 617 therethrough whereby upon clearance, the anvil rod 616 is locked within the adapter 618 by engagement of the tapered mounting portion 617 of the anvil rod with abutment surface 632 of adapter 618. During insertion, the external splines 624 of anvil rod are preferably aligned with the internal splines 634 of adapter 618 so as to received in interdigitating relation, thereby also rotationally fixing the anvil rod with respect to the adapter. As discussed hereinabove, the anvil adapter 618 permits the use of the reduced dimensioned anvil rod 616.

With reference again to FIG. 29, catheter guide 606 of apparatus 600 includes flexible outer member 636 which is preferably fabricated from a suitable polymeric material and defines a longitudinal bore 638 (shown in phantom) extending therethrough. Outer member 636 ranges in length from about 36 inches to about 60 inches to at least extend from the resected upper stomach section through the esophagus and out the mouth for engagement by the user. The distal end of outer member 636 is preformed to define an arched or curved section 640. Such configuration facilitates manipulation and passage of catheter guide 606 through the esophagus and into the resected upper stomach portion. An atraumatic tip 642 is mounted to the distal end of outer member 636 and a coupler member 644 is attached to the proximal end of the outer member. As depicted in FIG. 31, the coupler member 644 includes an internal thread 646 at its proximal end which receives the externally threaded collar 622 of suture unit 608 to operatively connect the delivery apparatus 602 and the catheter guide 606. Coupler member 644 is preferably rotationally mounted about outer member 636 to facilitate threaded engagement of the coupler and collar members 644, 622. Catheter guide 606 may further include a guide wire which is receivable within the longitudinal opening of the outer member 636. Preferably, the guide wire is sufficient in length to extend from the distal end portion of the outer guide to the proximal end for engagement by the user. However, it is to be appreciated that the use of a guide wire is optional.

Figure 36:
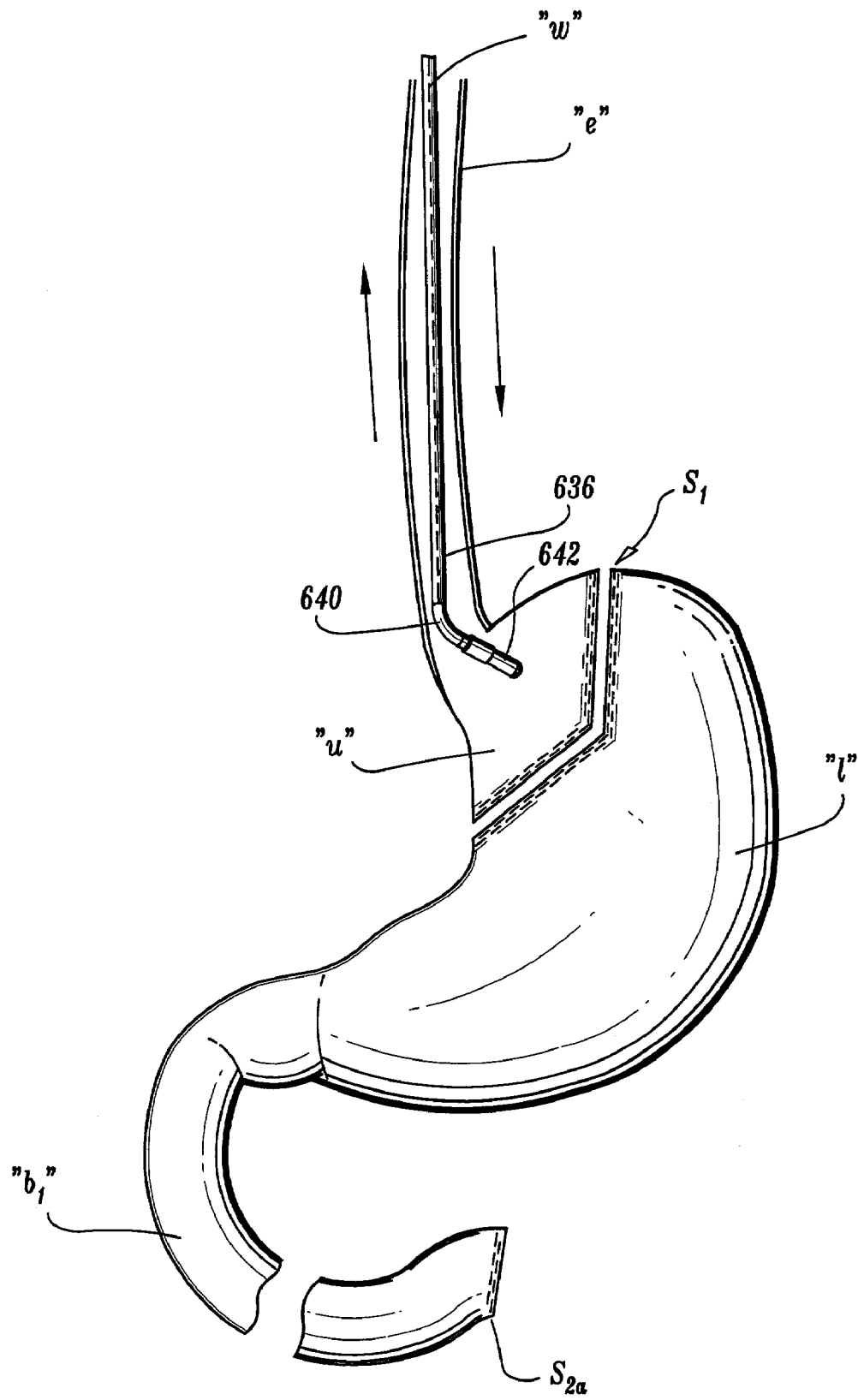
FIGS. 36–39 are views illustrating the sequence of steps in performing the laparoscopic gastric bypass procedure with the instruments of FIG. 29.

The use of the apparatus 600 will now be discussed. The upper stomach section "u" and the bowel "$b_2$" are resected in the manner discussed hereinabove in connection with FIGS. 7 and 8. With reference now to FIG. 36, initially, the catheter guide 606 and inserted guide wire "w", if used, is introduced within the oral cavity and passed through the esophageal passage "e" to be advanced within the upper stomach portion "u". It is noted that the curved distal portion 640 of the outer member 636 facilitates passage of the catheter guide 606 through manual manipulation and rotation of the outer member 636. Once the distal end of the outer member 636 accesses the upper stomach portion "u", the guide wire "w" is removed by retracting the guide wire in a proximal direction through the oral cavity. The delivery instrument 602 is then connected to the proximal end of the catheter guide 606 which extends from the mouth through the threaded interconnection of collar 622 of anvil component 604 and the coupler 644 of outer member 636 as discussed above.

Figure 37:
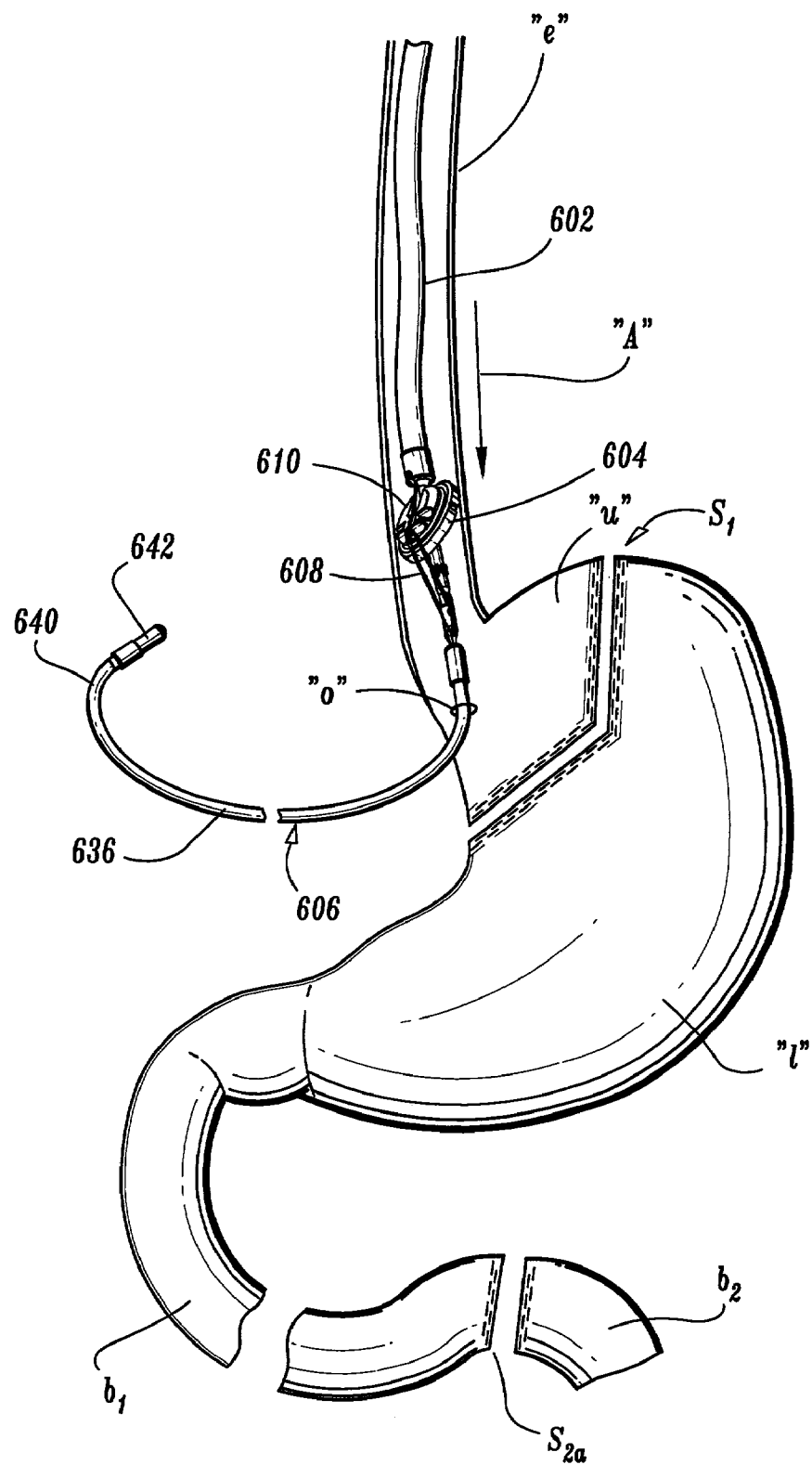

With reference to FIG. 37, the surgeon then accesses the distal end of outer member 636 through an incision "o" or trocar accessing the upper stomach portion "u" and pulls the entire system 600 through the esophagus "e" in the direction of directional arrow "A". Accordingly, the anvil component 604 and attached delivery instrument 602 are passed through the esophageal tract "e". It is noted that the anvil head 610 is in its pivoted non-operative position to facilitate passage through the tract. The surgeon continues to advance the components until anvil component 604 is within the upper stomach section "u" and visible to the surgeon. Thereafter, the suture unit 608 attached to anvil component 604 is severed and removed from the anvil component 604, which thereby disconnects catheter guide 606 from the anvil component 604. The catheter guide 606 is discarded.

Figure 38:
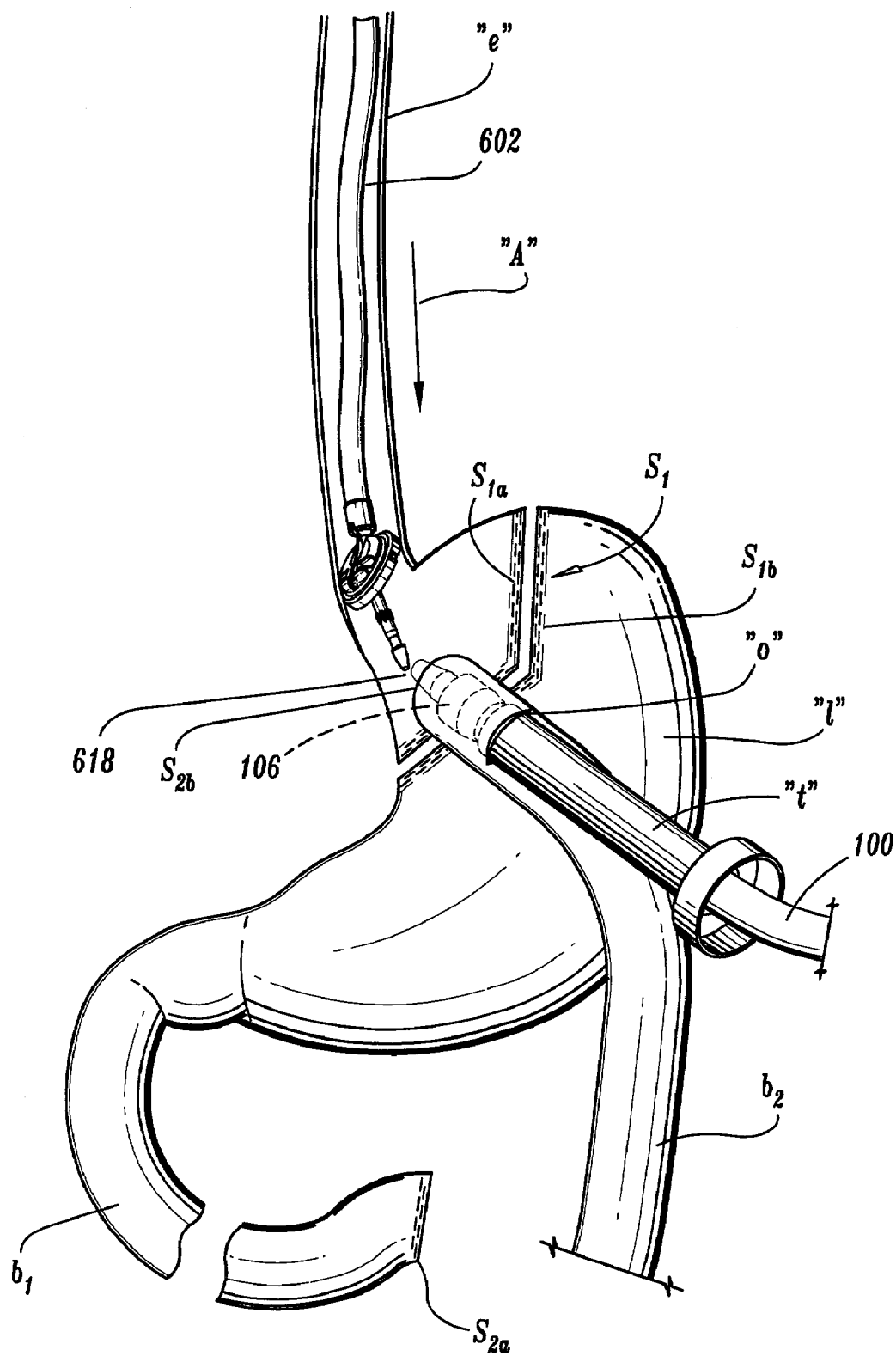

With reference to FIG. 38, bowel section "$b_2$" is positioned adjacent upper stomach section "u". A trocar "t" is introduced within an opening "o" in the bowel section "$b_2$". The circular anastomosis instrument 100 with attached adapter 618 is inserted in the trocar "t" and through an opening in the upper stomach portion "u".

Anvil adapter 618 is then mounted to anvil rod 616 of the anvil component 608. Delivery instrument 602 which extends through the esophagus such that its proximal end is exposed from the mouth is then actuated in the manner described in connection with the embodiment of FIGS. 23–28 to pivot the anvil head 610 to the operative position. The circular anastomosis instrument 100 and anvil head 610 are approximated and the instrument 100 fired to join the tissue portions in a manner previously described.

Figure 39:
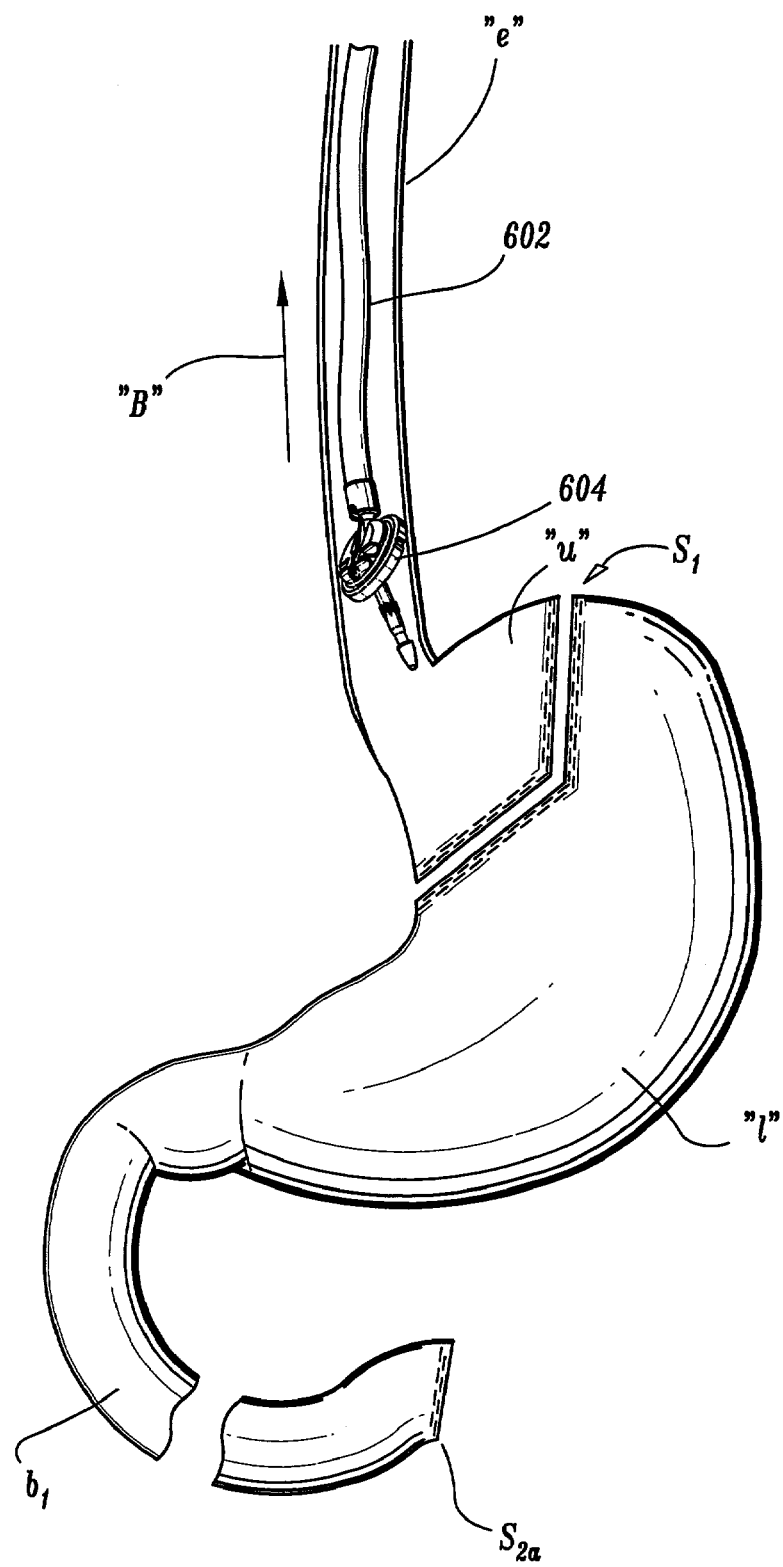

With reference to FIG. 39, anvil component 604 is released from anvil adapter 618. Delivery instrument 602 is actuated to return the anvil head to the pivoted non-operative position. Thereafter, delivery instrument 602 with attached anvil component 604 is removed back through the esophagus and mouth in the direction B of FIG. 39.

Figure 40:
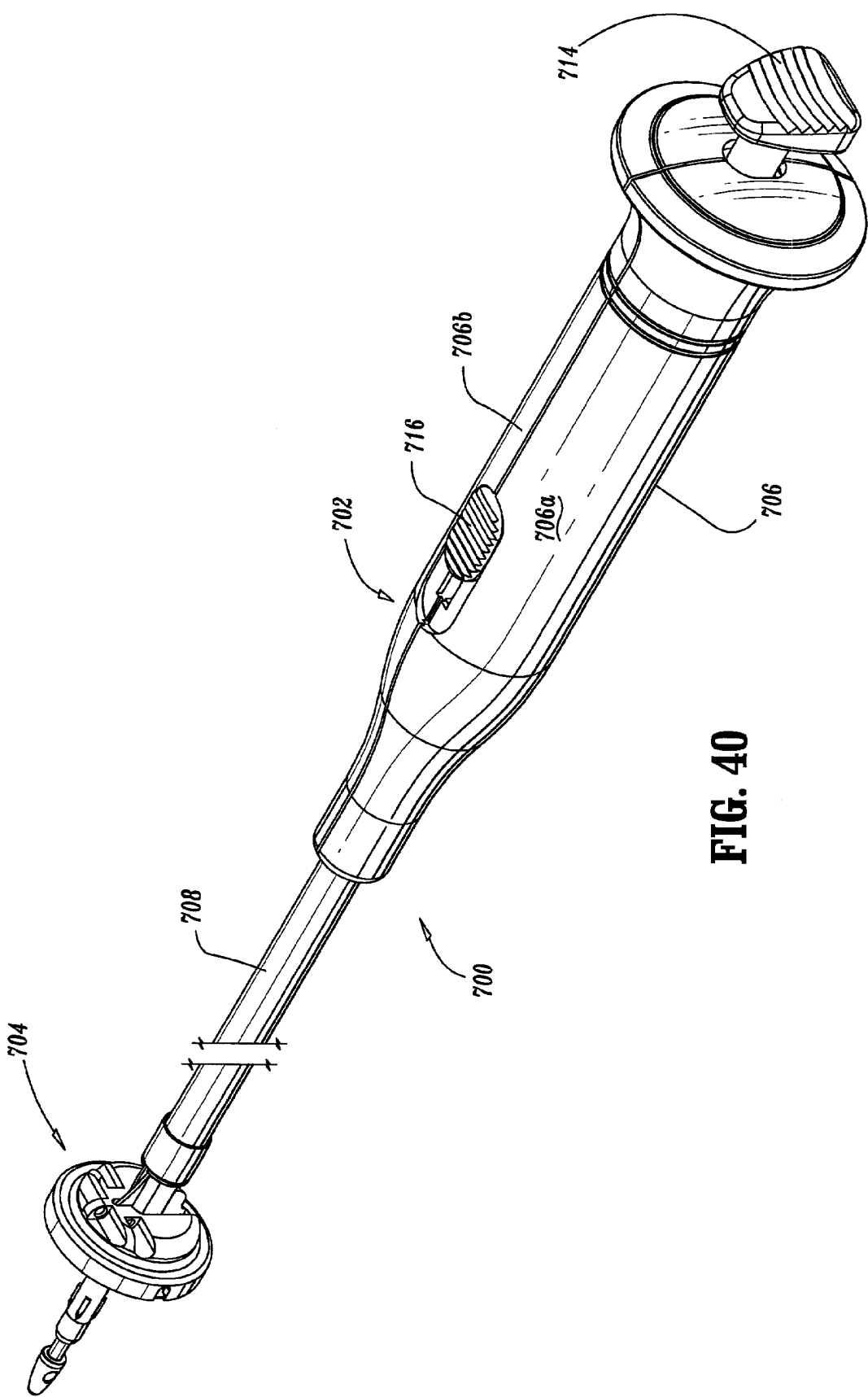
FIG. 40 is a perspective view of another alternate embodiment of the present disclosure illustrating the delivery apparatus and mounted anvil assembly.
Figure 41:
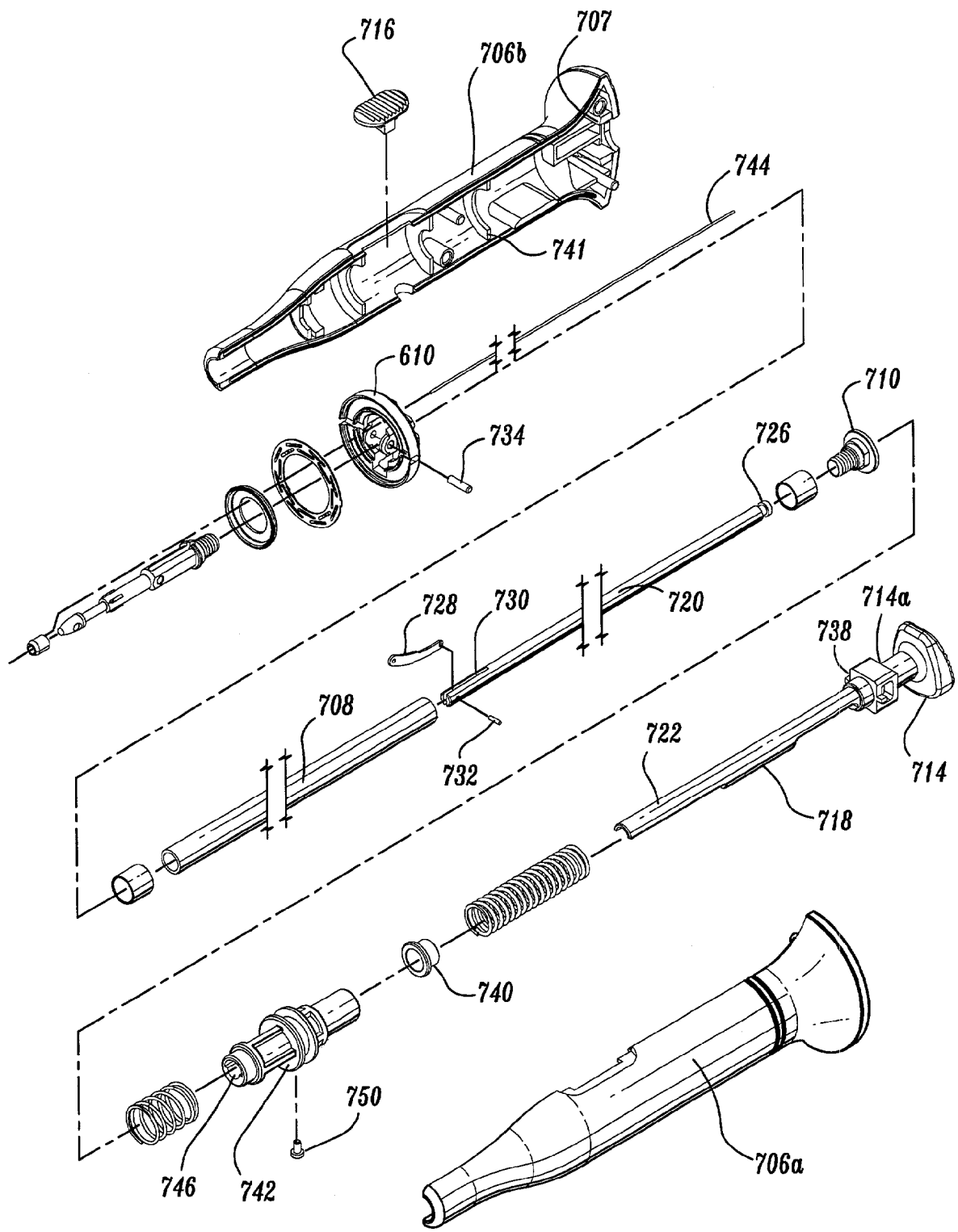
FIG. 41 is a perspective view with parts separated of the apparatus of FIG. 40.

Referring now to FIGS. 40–42, there is illustrated another alternate embodiment of the present disclosure. System 700 includes delivery instrument 702 and anvil assembly 704 releasably mounted to the delivery instrument 702. Anvil assembly 704 is substantially similar to the anvil assembly 604 described in connection with the embodiment of FIGS. 23–30, and reference is made thereto for particulars of the anvil assembly. Delivery instrument 702 includes handle 706 having handle half sections 706a, attached to each other through adhesive screws, or the like, and elongated sleeve 708 connected to the handle 706 and extending distally therefrom. In a preferred embodiment, handle 706 includes externally threaded collar 710 mounted within tile interior of the handle 706, which threadably engages corresponding internal threaded portion 710 of the elongated sleeve 708 to connect the two components. Other means for connecting are envisioned, including bayonet coupling, adhesives, etc. Handle 706 further possesses proximally positioned button 714 which functions to actuate a pivot mechanism for pivoting the anvil assembly 704, and manually engageable release button 716 which actuates a release mechanism for releasing anvil assembly 704 from the anastomosis instrument. The pivot and release mechanisms will be discussed in greater detail hereinbelow.

With reference now to FIGS. 41–43, the pivot mechanism is substantially similar to the pivot mechanism of the embodiment of FIG. 29 and includes pivot element 718 extending from button 714, and pivot rod 720 which is connected to the pivot element 718. Button 714 and pivot element 718 may be monolithically formed as a single unit as shown in the Figures. Pivot element 718 defines a semicircular open section 722 at its distal end to receive the proximal end of pivot rod 720. An internal circumferential rib 724 is integrally formed within the semicircular section 722 and is snap-fit into a circumferential groove 726 of pivot rod 720 to connect the two components.

The pivot mechanism further includes pivot link 728 which is received in a groove 730 defined at the distal end of pivot rod 720. Pivot link 728 is pivotally connected to pivot rod 720 through pin 732 and is further connected to anvil head 610 of anvil assembly through pin 734. The pivot mechanism moves in a longitudinal direction to cause corresponding pivotal movement of anvil head 610 between an operative position (FIG. 42) and a pivoted position (FIG. 43). The pivot mechanism is spring biased in the proximal direction corresponding to the operative position (FIG. 42) of the anvil assembly by coil spring 736. Coil spring 736 is coaxially arranged about pivot element 718 and engages, at its proximal end, abutment surface 738 of the pivot element 718 and, at its distal end, collar 740. Collar 740 is fixedly connected to the interior of handle portions 706a, b adjacent interior wall 741 of the handle 706. With this arrangement, coil spring 736 normally biases pivot element 718 and pivot button 714 in the proximal direction. The pivot mechanism may be releasably locked in the non-operative position by applying a radial directed force "r" to pivot button 714 to radially displace the button to the position depicted in FIG. 43. In this position, a locking shelf 714a of pivot button 714 engages a corresponding locking wall 707 of handle 706. Release of the pivot button 714 may be accomplished by radially displacing the pivot button 714 to its normal aligned position of FIG. 42.

With continued reference to FIGS. 40–43, the release mechanism for releasing anvil assembly 709 from its mounting to the end-to-end anastomosis instrument will be discussed. The release mechanism includes the aforementioned release button 716, release collar 742 disposed within handle 706 and flexible release link 744 connected to the release collar 742 and extending distally to the anvil assembly 704. Release collar 742 defines an internal longitudinal bore 746 dimensioned to receive pivot element 718 of the pivot mechanism and permit reciprocal slidable longitudinal movement of the pivot element therewithin. Release collar 742 is fixed to release button 714 through corresponding mounting structure of the two components, e.g., tongue and groove arrangement, identified generally by reference numeral 748 in FIGS. 42–43. Release link 744, in turn, is operatively connected to release collar 742 through set screw 750 which is positioned to securely engage the proximal end of the release link 744. Set screw 750 also permits the operator to adjust the positioning of the release link 744 relative to the release button 716 to account for manufacturing tolerances, etc.

Figure 44:
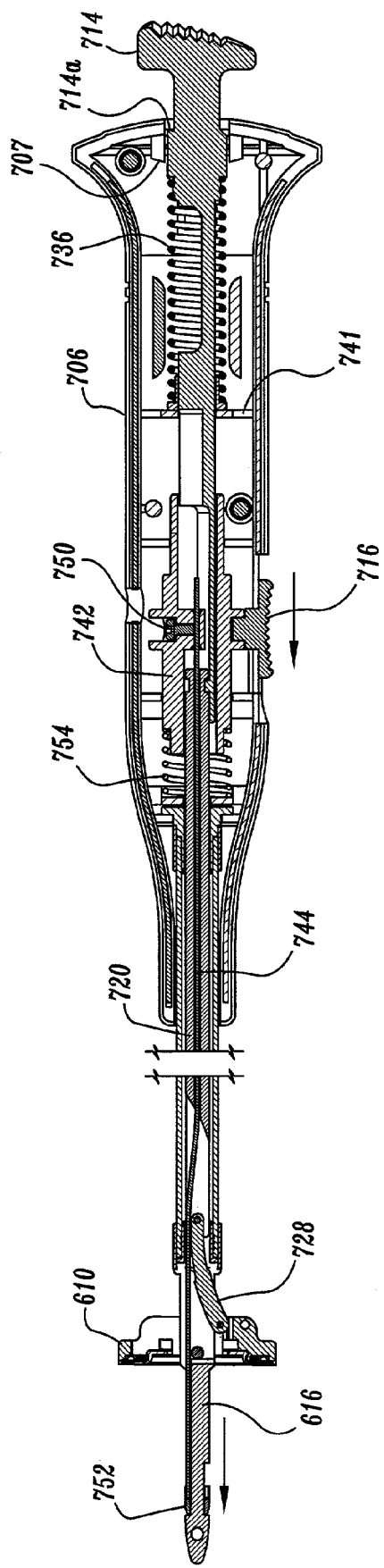
FIG. 44 is a view similar to the view of FIG. 42 illustrating the release mechanism actuated to release the anvil from the anastomosis instrument.
Figure 45:
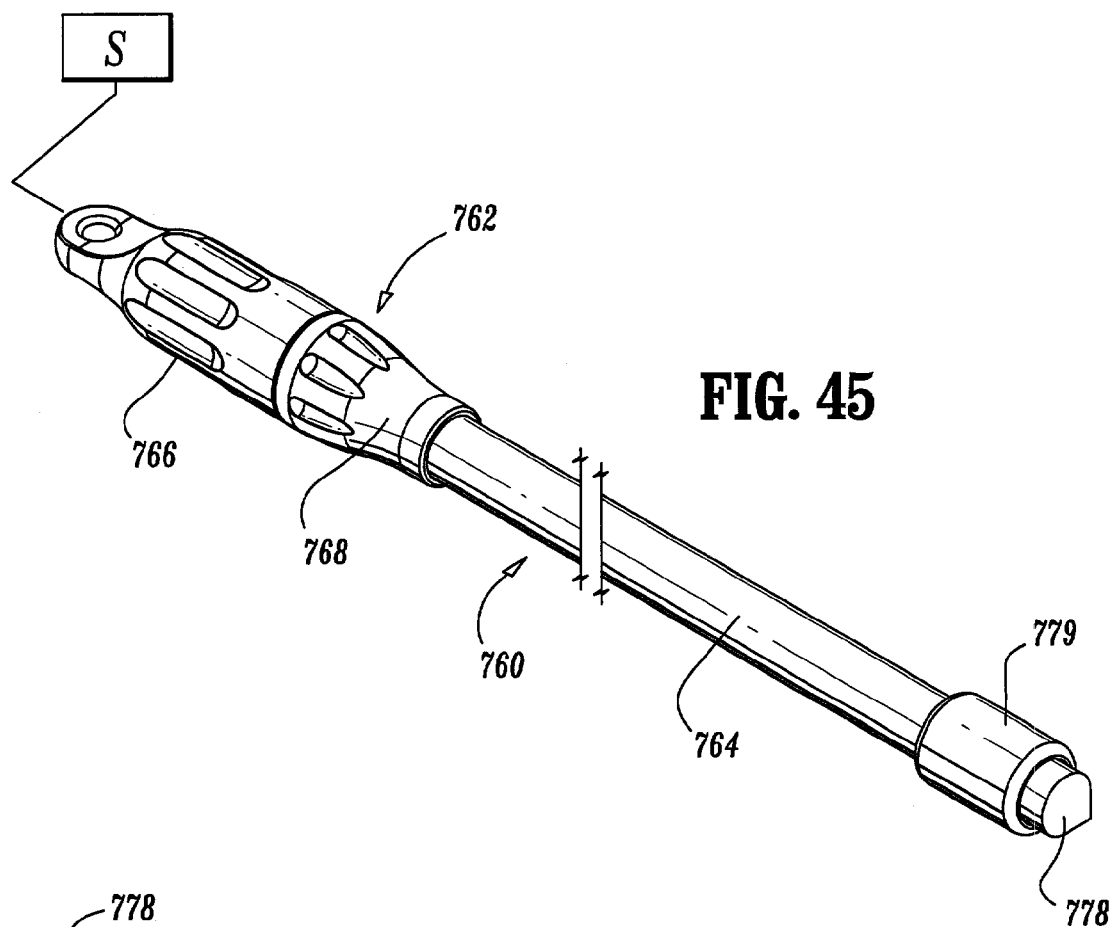
FIGS. 45–46 are perspective views of the light guide which is attachable to the anvil assembly.
Figure 46:
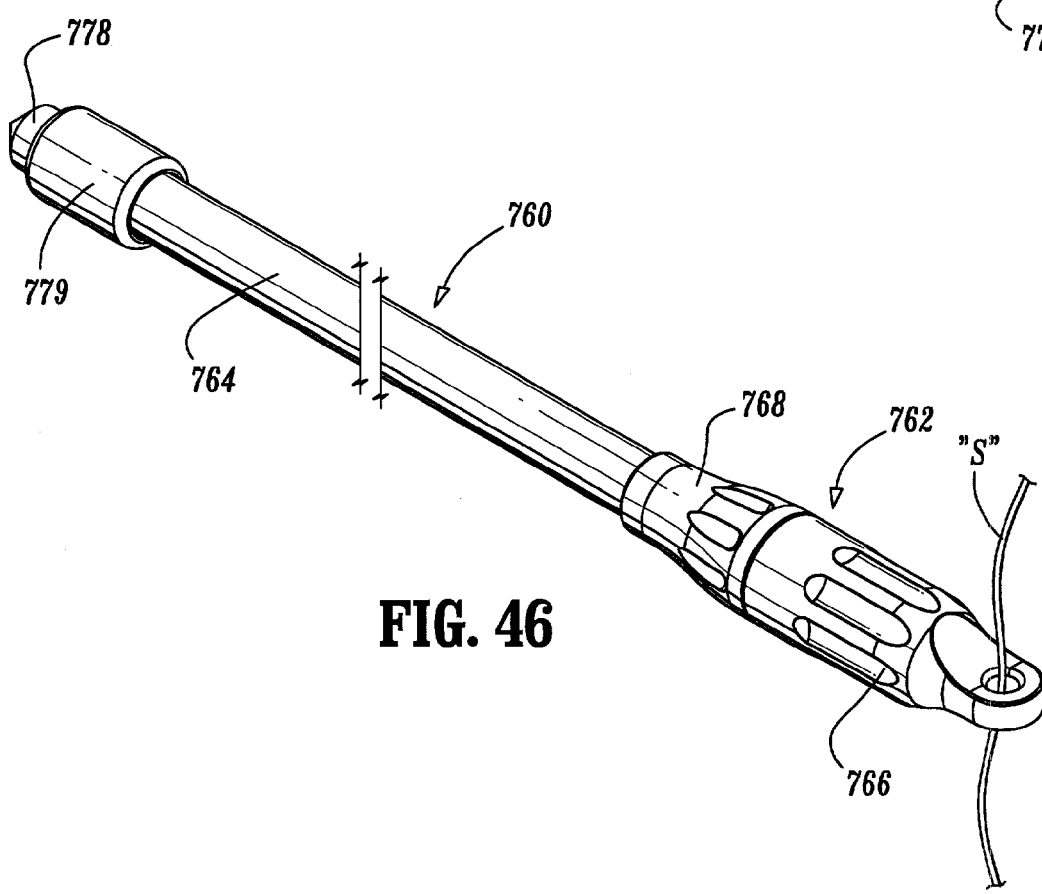

As best depicted in FIGS. 42–43, release link 744 is connected at its distal end to anvil release collar 752 which is coaxially positioned about the anvil rod 616 of anvil assembly 704. Such connection may be accomplished via conventional means, including adhesives or the like. Anvil release collar 752 moves relative to the anvil rod 616 upon corresponding longitudinal movement of release link 744 to thereby cause release of the anvil rod 616 relative to the anastomosis instrument, as will be discussed. The release mechanism is biased in a proximal direction by coil spring 754. Coil spring 754 engages, at its distal end, abutment wall 756 of handle 706 and engages, at its proximal end, abutment surface 758 of release collar 742 to normally bias the release collar 742 to the unactuated position depicted in FIG. 42. As shown in FIG. 44, the release mechanism is activated by advancing release button 716 distally against the influence of spring 754 which causes corresponding distal movement of release collar 742, release link 744 and anvil release collar 752. The relationship of anvil release collar 752 and anvil assembly 704 will be discussed hereinbelow.

Referring now to FIGS. 45–48, system 700 further includes light guide 760. Light guide or cable 760 is initially introduced through the esophagus to illuminate and/or visually inspect the operative site. Light guide 760 includes handle 762 and fibre cable 764 which extends distally from the handle 762. Handle 762 includes two distinct members, namely, proximal cap 766 and distal collar 768. Distal collar 768 defines a longitudinal bore 770 for reception of the proximal end of fiber cable 764 and is fixed to the fiber cable 764 by conventional means, including adhesives, crimping, etc. Distal collar 768 further includes an external threaded portion 772. Proximal cap 766 defines a longitudinal opening 774 and an internal threaded portion 776 which threadably engages the external threaded portion 772 of the distal collar 768 to connect the components.

Fiber cable 764 may be a single optical fiber as shown, or a plurality or bundle of fibers as appreciated by one skilled in the art. The optical fiber may be comprised of optical glass or polymeric matter. Fiber cable 764 extends to distal independent lens 778 which serves to focus the light emitted by the fiber cable 764. A collar 779 disposed adjacent the distal end of the fiber cable 764 mechanically couples the optical fiber and lens 778. Fiber cable 764 is connectable to a conventional light source "s" depicted in FIG. 45. Preferably, distal collar or adapter 768 is coupled to the light source in a conventional manner. Proximal cap 766 is attachable to the anvil assembly 704 through suture "s" (FIG. 46) as will be discussed.

Figure 49:
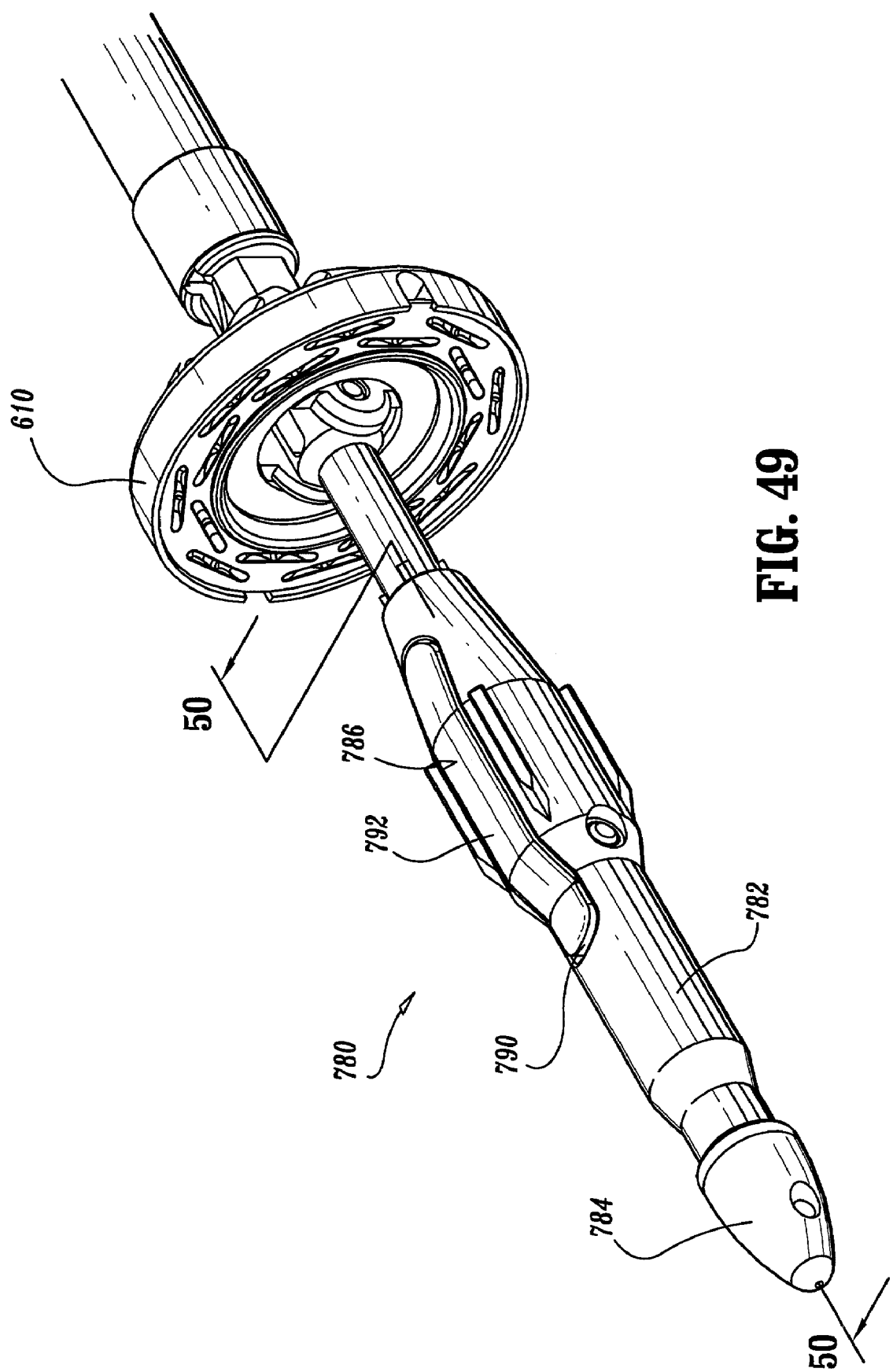
FIG. 49 is a perspective view of an anvil adapter depicted mounted to an anvil assembly.
Figure 50:
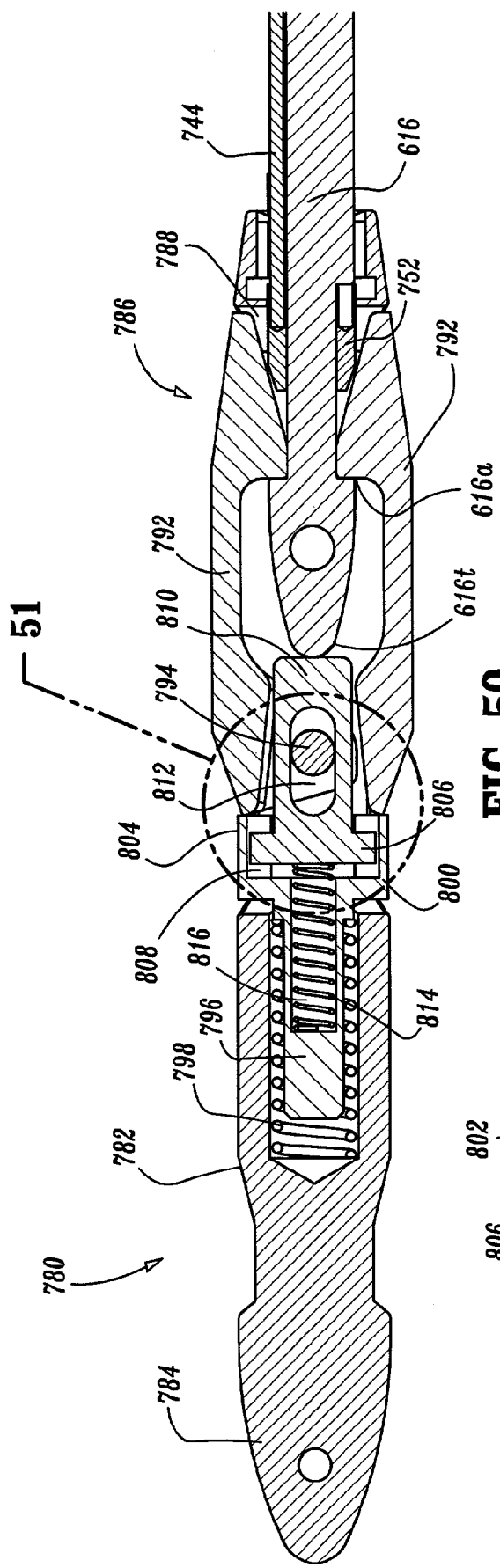
FIG. 50 is a cross-sectional view of the anvil adapter taken along the lines 50—50 of FIG. 49.
Figure 51:
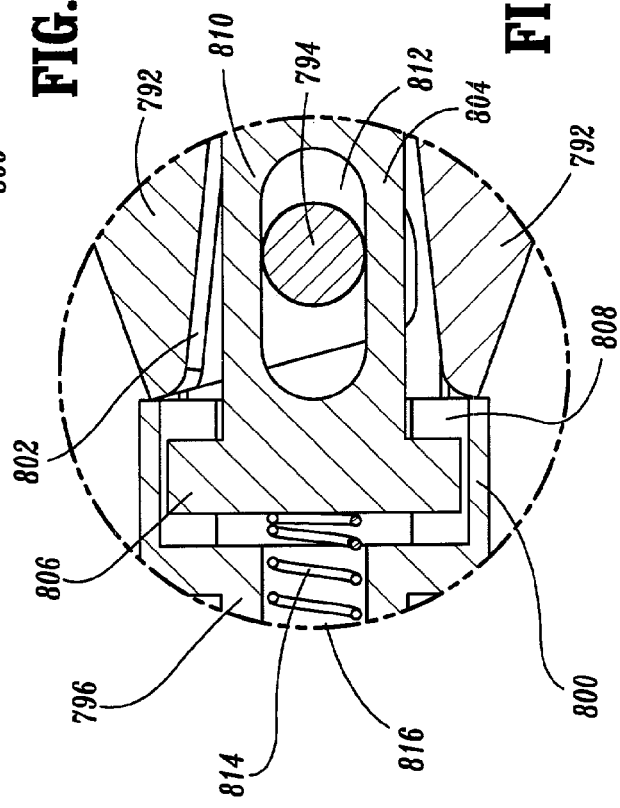
FIG. 51 is an enlarged isolated view depicting the relationship of the plunger and jaw mechanism of the anvil adapter.

With reference now to FIGS. 49–51, there is illustrated an embodiment of an anvil adapter 780 which is to be utilized with the system 700 of the present invention. Anvil adapter 780 couples anvil assembly 704 to the circular anastomosis instrument (FIG. 5) utilized in accordance with the preferred surgical procedure. The anvil adapter 780 permits the use of an anvil rod which is significantly reduced in diameter and length as discussed in connection with the embodiment of FIG. 29 to facilitate passage of the anvil assembly through the esophagus. Anvil adapter 780 includes adapter rod 782 having tapered mounting portion 784 for connection to the anastomosis instrument. The end of adapter rod 782 opposite the mounting portion 784 includes a jaw mechanism 786 which couples with anvil rod 616 of the anvil assembly 704 to connect the anvil adapter 780 and the anvil assembly 704. Adapter rod 782 defines a central longitudinal bore 788 which extends to form slots 790 in opposed wall portions of the rod 782 as shown in FIG. 49. The jaw mechanism includes first and second opposed jaws 792 pivotally mounted within longitudinal bore 788 of adapter rod 782 through pivot pin 794 and extending through the slots 790 of the adapter rod 782. Jaws 792 move between an engaged position with respect to anvil rod 616 (FIG. 50) to engage the anvil rod 616 and a release position to release the anvil rod 616 as will be discussed.

Anvil adapter 780 further includes plunger 796 which is mounted within longitudinal bore 788. Plunger 796 is normally biased toward opposed jaws 792 by coil spring 798 which is coaxially mounted about one end portion of the plunger 796. The other end portion of plunger 796 defines an enlarged cylindrical head 800. Head 800 of plunger 796 normally engages under the influence of coil spring 798, inclined camming surfaces 802 of jaws 792 to bias the jaws 792 to the closed position depicted in FIGS. 50 and 51.

Anvil adapter 780 further includes ejector plate 804 disposed within the central longitudinal bore 788 adjacent plunger 796. Ejector plate 804 has an enlarged head 806 which is received within cylindrical opening 808 of plunger head 800, and an elongated portion 810 depending from the head 806. Elongated portion 810 has a longitudinal bore 812 which accommodates pivot pin 794 of the jaw mechanism. Ejector plate 804 is normally biased toward jaws 792 by coil spring 814 which is disposed in a longitudinal opening 816 of plunger 796. When anvil 616 is secured within anvil adapter 780, coil spring 814 is compressed through engagement of the distal tip 616t of anvil rod 616 and elongated portion 810 of ejector plate 804. Ejector plate 804 is adapted for limited longitudinal movement relative to adapter rod 782 to release the anvil adapter 780 from the anvil. In particular, anvil adapter 780 is released from anvil rod 616 of anvil assembly 704 by advancing release button 716 to the distal position of FIG. 44 which advances release collar 742, release link 744 and anvil release collar 752. With reference to FIGS. 52–53, as anvil release collar 752 advances, camming surfaces 752a of release collar 752 engage inner inclined surfaces 792a of jaws 792 to radially displace the jaws to the position depicted in FIG. 53. Once the jaws 792 clear the vertical surface 616a of anvil rod 616 adjacent the tapered mounting portion, the anvil rod 616 may be disengaged.

Disengagement is facilitated through interaction of coil spring 814 and ejector plate 804 which moves proximally under influence of the compressed coil spring 814 to expel the anvil rod 616 in a proximal direction and released from the jaws 792 as detailed in FIG. 53. Thus, as appreciated, the releasing mechanism provides a positive expulsion force to eject anvil rod 616 from the anvil adapter 780 thereby obviating the need of the surgeon to forcibly separate the two components.

Figure 47:
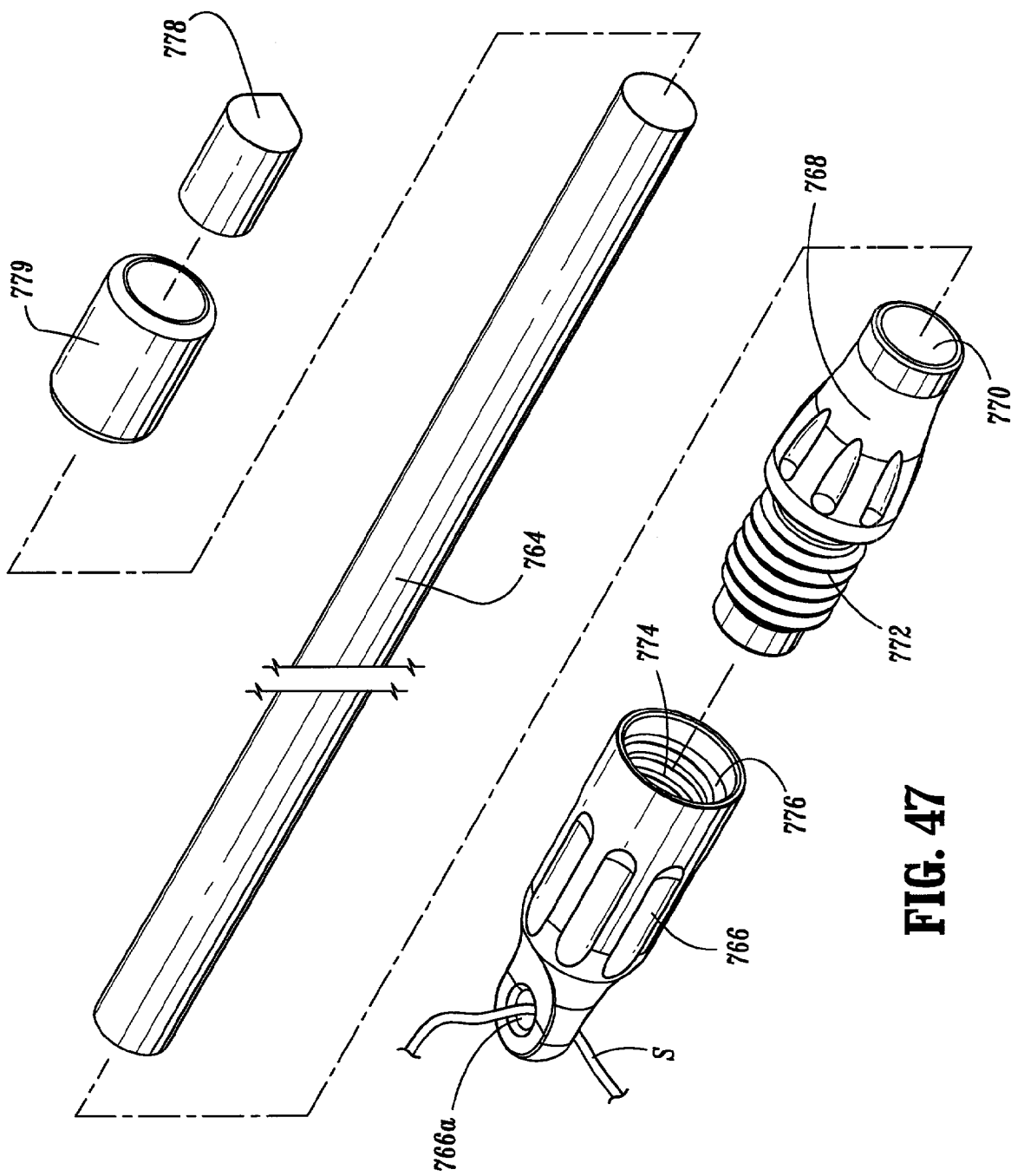
FIG. 47 is a perspective view with parts separated of the light guide.
Figure 48:
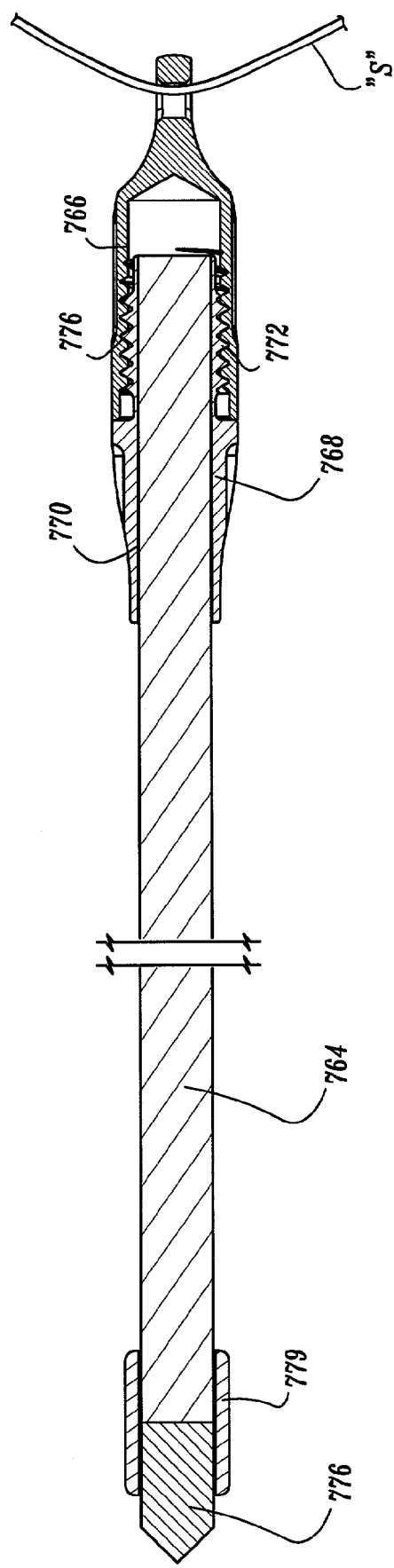
FIG. 48 is a side cross-sectional view of the light guide.

The use of system 700 will now be discussed. The upper stomach section "u" and the bowel "$b_2$" are resected in the manner discussed hereinabove in connection with FIGS. 7 and 8. Light guide 760 is then advanced through a gastric tube (not shown) positioned in the esophagus to be advanced within the upper stomach section "u" in a similar manner to that described in connection with insertion of the guide wire "w" of FIG. 36. The light guide 760 is then energized whereby light emitted by the guide 760 is focused on the interior wall of the upper stomach section "u". The focused light provides a visual indicator to the surgeon as to location of the light guide 760 so as to guide the surgeon in forming the incision in the wall of the upper stomach section "u". The incision is preferably formed adjacent the lit area of the stomach wall such that subsequent to creating the incision, the surgeon can grasp the distal end of the light guide 760. The light guide is disconnected from the light source. The delivery instrument 702 with mounted anvil assembly 704 is connected to the proximal end of the light guide. With reference to FIG. 47, in accordance with the preferred procedure, proximal cap 766 of light guide 760 is connected to anvil assembly 704 with a suture "s" which is looped through the eye loop 766a of the cap 766 and passed through the aperture "a" of anvil rod 616 in a similar manner to that shown and described in connection with FIGS. 29 and 30. It is noted that in accordance with this embodiment, the suture "s" is not required to be looped through the anvil head 610 of the anvil as shown in FIG. 29 in that the anvil head 610 is releasably locked in the pivoted position as discussed hereinabove. With the anvil assembly 704 connected to the proximal end of the light guide 760, the light guide 760, anvil assembly 704 and mounted delivery instrument 702 is pulled through the esophagus in a similar manner to that described in connection with FIG. 37.

The surgeon continues to advance the components until anvil component 700 is within the upper stomach section "u" and visible to the surgeon. Thereafter, the suture attached to anvil assembly 704 is severed and removed, thereby detaching light guide 760 which is then removed.

Figure 54:
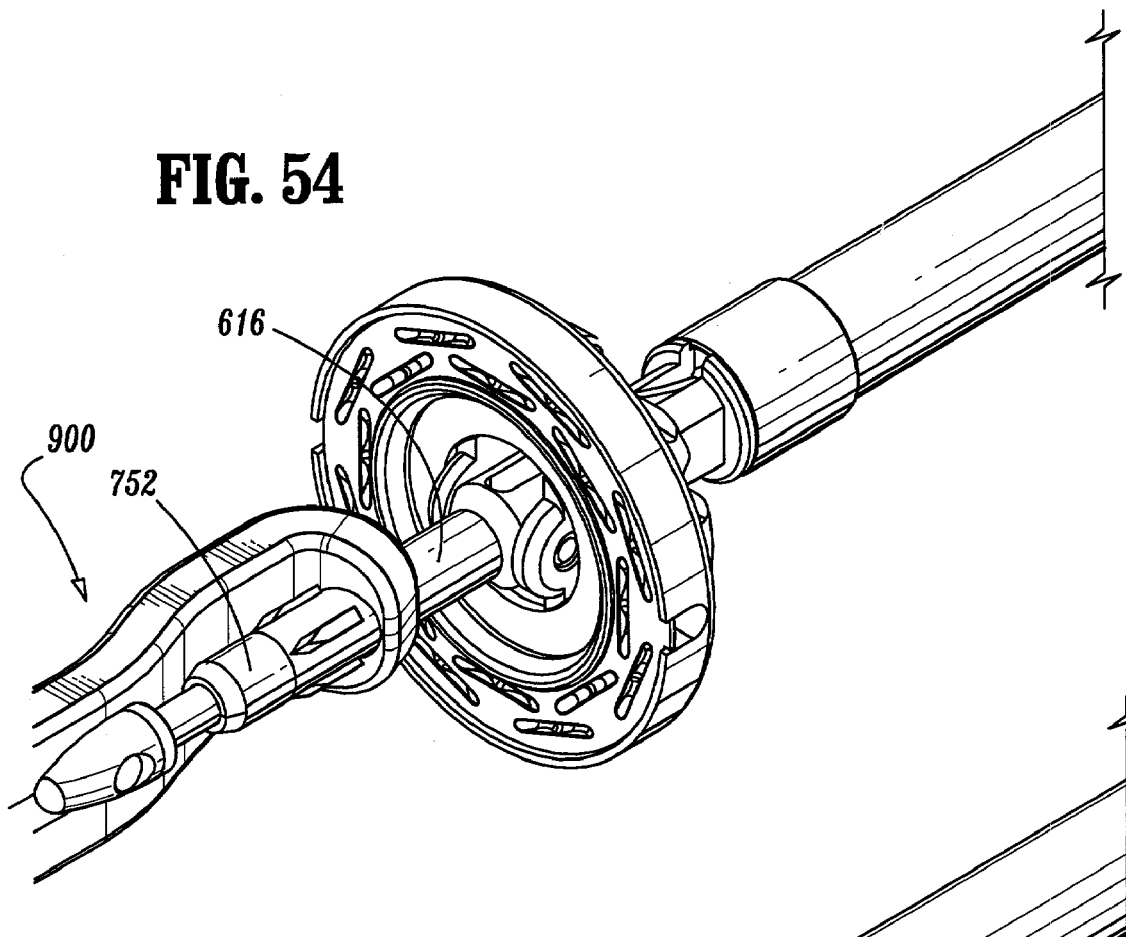
FIGS. 54–55 are enlarged perspective views of the jaw assembly of a grasping instrument suitable for grasping the anvil rod.
Figure 55:
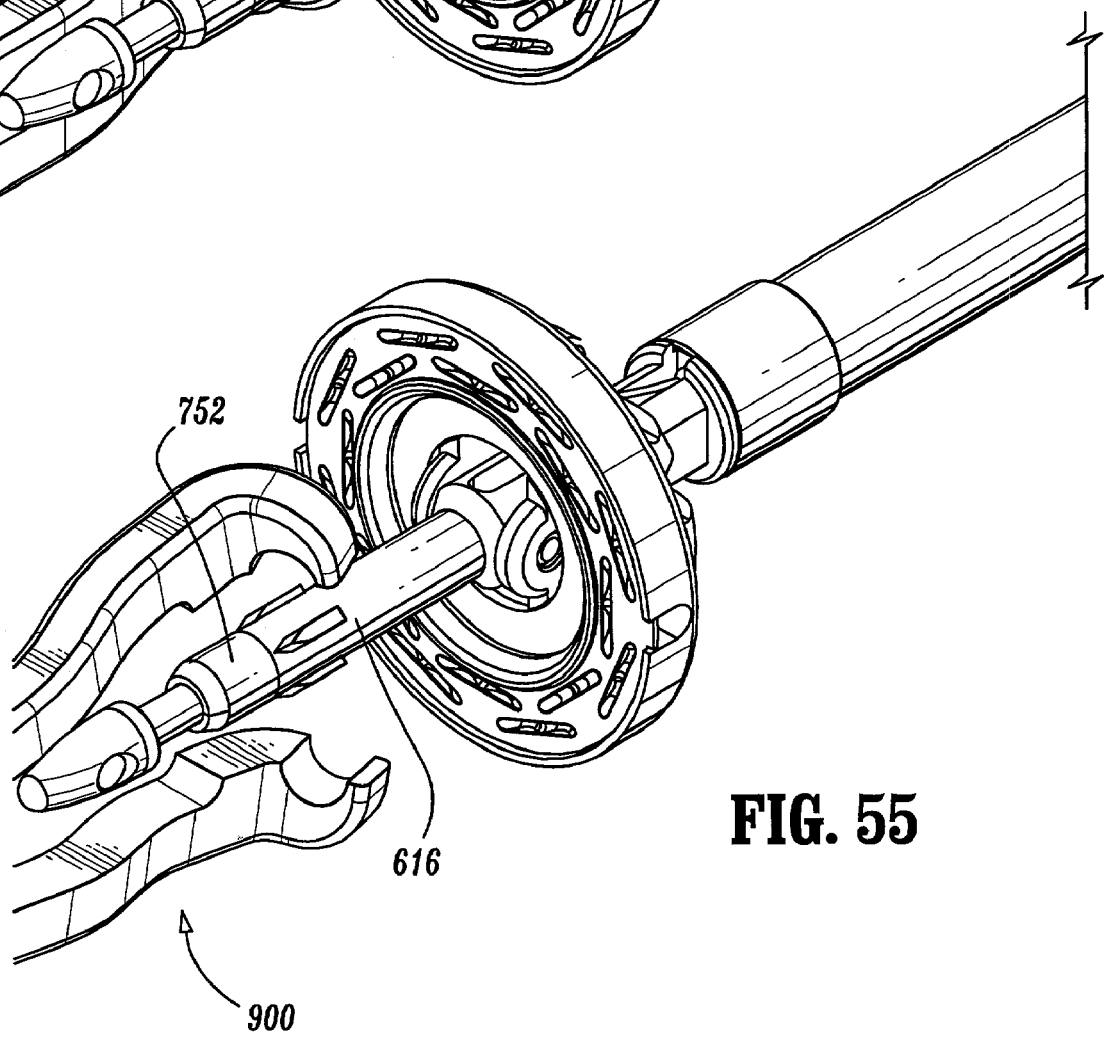

The bowel section "$b_2$" is positioned with respect to the upper stomach section "u", and the circular anastomosis instrument with attached adapter 780 is inserted through the trocar in the same manner detailed in connection with the discussion of FIG. 38. The anvil rod 616 of the anvil assembly 704 is grasped with a grasping instrument. For example, FIGS. 54–55 illustrate a novel grasping forceps which can facilitate gripping engagement of the anvil rod 616. This forceps is disclosed in commonly assigned provisional application entitled SURGICAL JAWS, mailed Mar. 5, 2001 under Express Mail Certificate No. EL 765221053 US, the contents of which is incorporated herein by reference. The forceps jaws 900 permit grasping of the anvil rod 616 from a substantially aligned direct near zero degree approach.

The anvil rod 616 is then mounted within anvil adapter 780 by advancing anvil rod 616 between jaws 792 of the anvil adapter 780 whereby upon insertion the jaws 792 are displaced outwardly. Once the mounting portion of anvil rod 616 clears the jaws 792, the jaws 792 return to their normal position under the influence of coil spring 798 and plunger 796 whereby the jaws 792 engage the vertical surface 616a of the anvil rod 616 to effectuate mounting of the anvil rod 616 to the anvil adapter 780 (FIG. 50).

Delivery instrument 702 may then be activated by releasing button 714 to permit the button 714 to return under the influence of coil spring 736 to its normal position of FIG. 42 thereby causing corresponding proximal movement of pivot rod 720 and pivot link 728 which pivots anvil head 610 to the operative position. The circular anastomosis instrument and anvil assembly are thereafter approximated and the instrument is fired to join the tissue portions.

The release mechanism is thereafter actuated to release anvil rod 616 from anvil adapter 780 in the manner discussed above. Delivery instrument is activated to return anvil head 610 to the pivoted non-operative position. The delivery instrument 702 and anvil assembly 704 are removed through the esophagus "e".

While the above description contains many specifics, these specifics should not be construed as limitations on the scope of the disclosure, but merely as exemplifications of preferred embodiments thereof. Those skilled in the art will envision other modifications within the scope and spirit of the claims appended hereto.

What is claimed is:

1. An apparatus for facilitating performance of a gastroplasty procedure, which comprises:
   an outer guide member dimensioned for insertion and passage through an esophagus of a patient, the outer guide member having a trailing proximal end and a leading distal end, and defining an opening therein extending at least along a portion of the length of the outer guide member;
   an elongate anvil delivery member at least partially disposed within the opening of the outer guide member, the delivery member adapted for relative distal longitudinal movement within the outer guide member from an initial position to an actuated position; and
   an anvil operatively engageable with the delivery member, the anvil including an anvil rod defining a longitudinal axis and an anvil head connected to the anvil rod, the anvil head being at least partially disposed within the opening of the outer guide member and being arranged proximal of the anvil rod when in the initial position of the delivery member and being fully exposed from the distal end of the outer guide member upon movement of the delivery member to the actuated position.

2. The apparatus according to claim 1 wherein the outer guide member includes an internal annular groove, the annular groove dimensioned to accommodate peripheral portions of the anvil head to facilitate retention of the anvil within the guide member.

3. The apparatus according to claim 1 wherein the insertion member comprises a flexible material.

4. The apparatus according to claim 3 wherein the cross-sectional dimension of the anvil head is greater than the internal dimension of the distal end of the outer guide, the outer guide member adapted to deform to permit passage of the anvil head through the opening to permit the anvil to be expelled from the insertion member.

5. An apparatus for facilitating performance of a gastroplasty procedure, which comprises:
   an outer guide member dimensioned for insertion and passage through an esophagus of a patient, the outer guide member having a proximal and distal ends, and defining an opening therein extending at least along a portion of the length of the outer guide member;
   an elongate anvil delivery member at least partially disposed within the opening of the outer guide member, the delivery member adapted for longitudinal movement within the outer guide member between an initial position and an actuated position; and
   an anvil operatively engageable with the delivery member, the anvil including an anvil rod defining a longitudinal axis and an anvil head connected to the anvil rod, the anvil head being at least partially disposed within the opening of the outer guide member when in the initial position of the delivery member and being fully exposed from the distal end of the outer guide member upon movement of the delivery member to the actuated position, the anvil head being pivotally mounted to the anvil rod, the anvil head pivotally movable between a non-operative position and an operative position.

6. The apparatus according to claim 5 further including a pivot member at least partially disposed within the outer guide member and operatively connected to the anvil head, the pivot member movable between first and second positions thereof to cause corresponding movement of the anvil head between the respective non-operative and operative positions.

7. The apparatus according to claim 6 wherein the pivot member is normally biased to the second position thereof.

8. The apparatus according to claim 7 including means for releasably locking the pivot member in the first position.

9. The apparatus according to claim 7 wherein the pivot member is releasably locked in the first position.

10. The apparatus according to claim 9 wherein the pivot member includes a locking surface engageable with a corresponding locking surface of one of the delivery member and outer guide member, the locking surfaces cooperating to releasably lock the pivot member in the first operative position.

11. The apparatus according to claim 10 wherein the pivot member includes a manually operable handle, the handle defining the locking surface of the pivot element.

12. The apparatus according to claim 6 wherein the pivot member is dimensioned to extend proximally beyond the insertion member to be grasped by the surgeon.

13. The apparatus according to claim 5 wherein the anvil is pivotally mounted to the delivery member.

14. The apparatus according to claim 13 further including an elongate pivot member at least partially disposed within the outer guide member, the pivot member operatively connected to the anvil and being movable to cause corresponding pivotal movement of the anvil through a pivotal range of motion.

15. A method for performing a bypass procedure in a digestive system, comprising the steps of:
introducing an anvil including an anvil head and an anvil rod extending from the anvil head through an esophagus of a patient and into a first digestive tissue portion;
inserting an anastomosis instrument into a second digestive tissue portion displaced from the first digestive tissue portion;
manipulating the anvil from a proximal location to position the anvil at a desired orientation with respect to the anastomosis instrument;
engaging the anvil rod of the anvil with the anastomosis instrument; and
firing the anastomosis instrument to connect the first and second digestive tissue portions.

16. The method according to claim 15 wherein the anvil is at least partially disposed within an outer guide and wherein the step of introducing includes advancing the outer guide and anvil through the esophagus.

17. The method according to claim 16 further including the step of moving the anvil relative to the outer guide to fully expose the anvil from the outer guide.

18. The method according to claim 17 including a delivery member at least partially disposed within the outer guide and operatively engageable with the anvil and wherein the step of moving includes advancing the delivery member to expel the anvil from the outer guide.

19. The method according to 15 further including the step of positioning a linear stapler instrument adjacent the first digestive tissue portion, and further including the step of firing the linear stapler instrument to form a staple line adjacent the first digestive tissue portion.

20. The method according to claim 19 further including the step of positioning a linear stapler instrument adjacent the second digestive tissue portion, and further including the step of firing the linear stapler instrument to form a staple line adjacent the second digestive tissue portion.

21. The method according to claim 20 wherein the linear stapler instruments each include a cutting member associated therewith, and wherein the steps of firing include actuating the cutting member to server tissue adjacent the staple lines to thereby resect the section digestive tissue between the staple lines.

22. The method according to claim 20 further including the step of forming access openings in each of the first and second digestive tissue portions and further including the step of passing the anvil rod of the anvil through the access opening of the first digestive tissue portion and through the access opening of the second digestive tissue portion to connect to the anastomosis instrument.

23. The method according to claim 22 wherein each of the steps of positioning is performed laparoscopically through a trocar.

24. The method according to claim 15, further including the step of disconnecting the anvil from the anastomosis instrument and withdrawing the anvil through the esophagus.

25. The method according to claim 15 wherein the step of introducing includes advancing the anvil with the anvil rod leading through the esophagus and the anvil head trailing.

26. A method for performing a bypass procedure in a digestive system, comprising the steps of:

introducing an anvil including an anvil rod and an anvil head pivotally mounted to the anvil rod through an esophagus of a patient and into a first digestive tissue portion;
inserting an anastomosis instrument into a second digestive tissue portion displaced from the first digestive tissue portion;
manipulating the anvil from a proximal location to position the anvil at a desired orientation with respect to the anastomosis instrument;
connecting the anvil to the anastomosis instrument;
pivoting the anvil head from a non-operative position to an operative position; and
firing the anastomosis instrument to connect the first and second digestive tissue portions.

27. The method according to claim 26 further including a pivot member disposed with the outer guide and operatively engageable with the anvil head and wherein the step of pivoting includes moving the pivot member to cause the anvil head to pivot to the operative position.

28. A method for performing a bypass procedure in a digestive system, comprising the steps of:
introducing an anvil through an esophagus of a patient and into a first digestive tissue portion, the anvil being pivotally mounted to a support member;
inserting an anastomosis instrument into a second digestive tissue portion displaced from the first digestive tissue portion;
manipulating the anvil from a proximal location by pivoting the anvil relative to the support member to orient the anvil to a desired position with respect to the anastomosis instrument;
connecting the anvil to the anastomosis instrument; and
firing the anastomosis instrument to connect the first and second digestive tissue portions.

29. The method according to claim 28 wherein the anvil is operatively connected to a movable pivot member and wherein the step of manipulating includes moving the pivot member thereby causing pivotal movement of the anvil relative to the support member.

30. A method for performing a bypass procedure in a digestive system, comprising the steps of:
introducing an anvil through an esophagus of a patient and into a first digestive tissue portion;
inserting an anastomosis instrument through a trocar into a second digestive tissue portion displaced from the first digestive tissue portion;
manipulating the anvil from a proximal location to position the anvil at a desired orientation with respect to the anastomosis instrument;
connecting the anvil to the anastomosis instrument; and
firing the anastomosis instrument to connect the first and second digestive tissue portions.

31. A method for performing a bypass procedure in a digestive system, comprising the steps of:
introducing an anvil through an esophagus of a patient and at least partially positioning the anvil into a stomach tissue portion;
at least partially positioning an anastomosis instrument into an intestinal tissue portion
manipulating the anvil from a proximal location to position the anvil at a desired orientation with respect to the anastomosis instrument;
connecting the anvil to the anastomosis instrument; and
firing the anastomosis instrument to connect the stomach tissue portion and the intestinal tissue portion.

32. The method according to claim 31 including the step of isolating an upper stomach portion, the upper stomach portion being connected to the esophagus.

33. The method according to claim 32 further including the step of resecting the bowel to define a first bowel portion connected to the stomach and a second bowel portion separated from the first bowel portion.

34. The method according to claim 33 further including the steps of approximating and connecting the second bowl portion and the upper stomach portion.

35. A method for performing a bypass procedure in a digestive system, comprising the steps of:
    introducing an anvil through an esophagus of a patient and at least partially positioning the anvil into an esophageal tissue portion;
    at least partially positioning an anastomosis instrument into one of a stomach tissue portion and an intestinal tissue portion
    manipulating the anvil from a proximal location to position the anvil at a desired orientation with respect to the anastomosis instrument;
    connecting the anvil to the anastomosis instrument; and
    firing the anastomosis instrument to connect the esophageal tissue portion to the one of the stomach portion and the intestinal tissue portion.

36. A method for performing a bypass procedure in a digestive system, comprising the steps of:
    introducing an anvil through an esophagus of a patient and at least partially positioning the anvil into a first stomach tissue portion,
    at least partially positioning an anastomosis instrument into a second stomach tissue portion
    manipulating the anvil from a proximal location to position the anvil at a desired orientation with respect to the anastomosis instrument;
    connecting the anvil to the anastomosis instrument; and
    firing the anastomosis instrument to connect the first stomach tissue portion and the second stomach tissue portion.

37. An anvil delivery instrument which comprises:
    an elongated outer member defining a general longitudinal axis and having proximal and distal ends, and defining a longitudinal bore;
    a pivot member at least partially disposed within the longitudinal bore of the outer member, the pivot member adapted for longitudinal movement within the outer member; and
    an anvil mounted to the outer member and operatively connected to the pivot member, the anvil including an anvil rod and an anvil head pivotally mounted to the anvil rod, the anvil head pivotally movable from a non-operative position to an operative position upon longitudinal movement of the pivot member, the anvil rod being mountable with respect to an end to end anastomosis instrument.

38. The instrument according to claim 37 wherein the pivot member is normally biased to a first position corresponding to the operative position of the anvil head.

39. The instrument according to claim 38 wherein the pivot member is releasably locked in a second position corresponding to the non-operative position of the anvil head.

40. The instrument according to claim 39 including a manually operable handle connected to the pivot member, the handle being manipulable to release the pivot member to permit longitudinal movement of the pivot member to the first position.

41. The instrument according to claim 37 further including an elongated catheter guide operatively connectable to the distal end of the outer member, the catheter guide dimensioned for passage through a restricted passage.

42. The instrument according to claim 41 wherein the catheter guide is connected to the anvil.

43. The instrument according to claim 42 wherein the anvil includes a suture assembly mounted thereto, the suture assembly including a length of suture looped through an opening in the anvil.

44. The instrument according to claim 43 wherein the suture assembly includes a coupler connected to the length of suture and wherein the catheter guide includes a corresponding couplers being engageable to connect the catheter guide and the anvil.

45. A method for performing a bypass procedure in a digestive system, comprising the steps of:
    providing an outer guide including an anvil movably and at least partially disposed therein;
    concurrently advancing the outer guide and the anvil through an esophagus of a patient and into a first digestive tissue portion;
    inserting an anastomosis instrument into a second digestive tissue portion displaced from the first digestive tissue portion;
    manipulating the anvil from a proximal location to position the anvil at a desired orientation with respect to the anastomosis instrument;
    connecting the anvil to the anastomosis instrument; and
    firing the anastomosis instrument to connect the first and second digestive tissue portions.

* * * * *